US012778703B2

(12) United States Patent
Baldwin et al.

(10) Patent No.: US 12,778,703 B2
(45) Date of Patent: Nov. 3, 2026

(54) MECHANISM FOR MANUALLY ACTIVATED TOOL ADJUSTMENT

(71) Applicant: Intuitive Surgical Operations, Inc., Sunnyvale, CA (US)

(72) Inventors: Michael Baldwin, Los Gatos, CA (US); William A. Burbank, Sandy Hook, CT (US); Wesley Chung Joe, Fremont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 89 days.

(21) Appl. No.: 18/695,736

(22) PCT Filed: Sep. 26, 2022

(86) PCT No.: PCT/US2022/044704

§ 371 (c)(1),
(2) Date: Mar. 26, 2024

(87) PCT Pub. No.: WO2023/055684

PCT Pub. Date: Apr. 6, 2023

(65) Prior Publication Data

US 2025/0000598 A1 Jan. 2, 2025

Related U.S. Application Data

(60) Provisional application No. 63/251,416, filed on Oct. 1, 2021.

(51) Int. Cl.

| | |
|---|---|
| ***A61B 34/00*** | (2016.01) |
| ***A61B 17/29*** | (2006.01) |
| *A61B 17/00* | (2006.01) |

(52) U.S. Cl.

CPC .............. *A61B 34/74* (2016.02); *A61B 17/29* (2013.01); *A61B 2017/00398* (2013.01)

(58) Field of Classification Search

CPC ......... A61B 34/74; A61B 34/71; A61B 17/29; A61B 2017/00398; A61B 2090/033;
(Continued)

(56) References Cited

U.S. PATENT DOCUMENTS 2,091,317 A 8/1937 Hill
2,906,143 A 9/1959 Musser
(Continued)

FOREIGN PATENT DOCUMENTS

AU 2014208189 A1 4/2015
CN 1939228 A 4/2007
(Continued)

OTHER PUBLICATIONS

Office Action for EP Application No. EP22793287.8, mailed Apr. 9, 2025, 12 pages.
(Continued)

*Primary Examiner* — Brooke Labranche

(57) ABSTRACT

A medical device includes a manual drive structure having a manual drive input member and a manual drive coupling member. The medical device also includes a first tool drive member including a first motor drive input member and a second tool drive member including a second motor drive input member. The first tool drive member is coupled to and driven by the manual drive input member via the manual drive coupling member and the second tool drive member is coupled to and driven by the manual drive input member via the manual drive coupling member.

20 Claims, 40 Drawing Sheets

(58) Field of Classification Search
CPC ........ A61B 2090/0818; A61B 2090/03; A61B 2090/031; A61B 2034/715
See application file for complete search history.

(56) References Cited

U.S. PATENT DOCUMENTS

| | | | |
|---|---|---|---|
| 3,312,496 | A | 4/1967 | Albert et al. |
| 4,084,594 | A | 4/1978 | Mosior |
| 4,139,104 | A | 2/1979 | Mink |
| 5,099,705 | A | 3/1992 | Dravnieks |
| 5,207,691 | A | 5/1993 | Nardella |
| 5,352,235 | A | 10/1994 | Koros et al. |
| 5,792,135 | A | 8/1998 | Madhani et al. |
| 5,807,377 | A | 9/1998 | Madhani et al. |
| 5,817,128 | A | 10/1998 | Storz |
| 5,855,583 | A | 1/1999 | Wang et al. |
| 5,876,325 | A | 3/1999 | Mizuno et al. |
| 6,007,550 | A | 12/1999 | Wang et al. |
| 6,318,199 | B1 | 11/2001 | Buck |
| 6,817,974 | B2 | 11/2004 | Cooper et al. |
| 6,994,708 | B2 | 2/2006 | Manzo |
| 7,083,571 | B2 | 8/2006 | Wang et al. |
| 7,090,683 | B2 | 8/2006 | Brock et al. |
| 7,169,141 | B2 | 1/2007 | Brock et al. |
| 7,214,230 | B2 | 5/2007 | Brock et al. |
| 7,331,967 | B2 | 2/2008 | Lee et al. |
| 7,371,210 | B2 | 5/2008 | Brock et al. |
| 7,666,191 | B2 | 2/2010 | Orban, III et al. |
| 7,935,130 | B2 | 5/2011 | Williams |
| 7,963,913 | B2 | 6/2011 | Devengenzo et al. |
| 8,142,447 | B2 | 3/2012 | Cooper et al. |
| 8,224,484 | B2 | 7/2012 | Swarup et al. |
| 8,241,271 | B2 | 8/2012 | Millman et al. |
| 8,444,631 | B2 | 5/2013 | Yeung et al. |
| 8,479,969 | B2 | 7/2013 | Shelton, IV |
| 8,506,555 | B2 | 8/2013 | Ruiz Morales |
| 8,551,115 | B2 | 10/2013 | Steger et al. |
| 8,573,465 | B2 | 11/2013 | Shelton, IV |
| 8,602,031 | B2 | 12/2013 | Reis et al. |
| 8,771,270 | B2 | 7/2014 | Burbank |
| 8,800,838 | B2 | 8/2014 | Shelton, IV |
| 8,992,565 | B2 | 3/2015 | Brisson et al. |
| 9,002,518 | B2 | 4/2015 | Manzo et al. |
| 9,028,494 | B2 | 5/2015 | Shelton, IV et al. |
| 9,078,684 | B2 | 7/2015 | Williams |
| 9,121,494 | B2 | 9/2015 | Buchleitner et al. |
| 9,204,923 | B2 | 12/2015 | Manzo et al. |
| 9,232,979 | B2 | 1/2016 | Parihar et al. |
| 9,259,274 | B2 | 2/2016 | Prisco |
| 9,524,022 | B2 | 12/2016 | Nakayama |
| 9,572,616 | B2 | 2/2017 | Vaughn |
| 9,737,373 | B2 | 8/2017 | Schuh |
| 9,750,578 | B2 | 9/2017 | Alden et al. |
| 9,839,439 | B2 | 12/2017 | Cooper et al. |
| 9,913,694 | B2 | 3/2018 | Brisson |
| 9,931,106 | B2 | 4/2018 | Au et al. |
| 9,993,313 | B2 | 6/2018 | Schuh et al. |
| 10,076,348 | B2 | 9/2018 | Anderson et al. |
| 10,201,365 | B2 | 2/2019 | Boudreaux et al. |
| 10,288,837 | B2 | 5/2019 | Miyatani et al. |
| 10,314,583 | B2 | 6/2019 | Smith et al. |
| 10,357,321 | B2 | 7/2019 | Donlon et al. |
| 10,470,830 | B2 | 11/2019 | Hill et al. |
| 10,478,256 | B2 | 11/2019 | Shelton, IV et al. |
| 10,543,051 | B2 | 1/2020 | Schena et al. |
| 10,624,709 | B2 | 4/2020 | Remm |
| 10,772,690 | B2 | 9/2020 | Prisco |
| 10,779,898 | B2 | 9/2020 | Hill et al. |
| 10,806,530 | B2 | 10/2020 | Liao et al. |
| 10,881,280 | B2 | 1/2021 | Baez, Jr. |
| 10,932,868 | B2 | 3/2021 | Solomon et al. |
| 11,020,112 | B2 | 6/2021 | Shelton, IV et al. |
| 11,045,270 | B2 | 6/2021 | Shelton, IV et al. |
| 11,076,926 | B2 | 8/2021 | Ragosta et al. |
| 11,118,661 | B2 | 9/2021 | Abbott |
| 11,304,770 | B2 | 4/2022 | Crews et al. |
| 2002/0111635 | A1 | 8/2002 | Jensen et al. |
| 2003/0068607 | A1 | 4/2003 | Gregorio et al. |
| 2005/0119527 | A1 | 6/2005 | Banik et al. |
| 2006/0190034 | A1 | 8/2006 | Nishizawa et al. |
| 2006/0217742 | A1 | 9/2006 | Messerly et al. |
| 2006/0276775 | A1 | 12/2006 | Rosenberg et al. |
| 2007/0043338 | A1 | 2/2007 | Moll et al. |
| 2007/0137371 | A1 | 6/2007 | Devengenzo et al. |
| 2007/0208375 | A1 | 9/2007 | Nishizawa et al. |
| 2007/0232858 | A1 | 10/2007 | Macnamara et al. |
| 2008/0009838 | A1 | 1/2008 | Schena et al. |
| 2008/0015566 | A1 | 1/2008 | Livneh |
| 2008/0046122 | A1 | 2/2008 | Manzo et al. |
| 2008/0087871 | A1 | 4/2008 | Schena et al. |
| 2008/0103491 | A1 | 5/2008 | Omori et al. |
| 2008/0196533 | A1 | 8/2008 | Bergamasco et al. |
| 2009/0088774 | A1 | 4/2009 | Swarup et al. |
| 2009/0112230 | A1 | 4/2009 | Jinno |
| 2009/0198272 | A1 | 8/2009 | Kerver et al. |
| 2009/0222022 | A1 | 9/2009 | Laporte et al. |
| 2010/0011900 | A1 | 1/2010 | Burbank et al. |
| 2010/0318101 | A1 | 12/2010 | Choi et al. |
| 2011/0015650 | A1 | 1/2011 | Choi et al. |
| 2011/0065992 | A1 | 3/2011 | Bissinger |
| 2011/0071543 | A1 | 3/2011 | Prisco et al. |
| 2011/0118754 | A1 | 5/2011 | Dachs, II et al. |
| 2011/0277775 | A1 | 11/2011 | Holop et al. |
| 2011/0295269 | A1 | 12/2011 | Swensgard et al. |
| 2011/0295270 | A1 | 12/2011 | Giordano et al. |
| 2011/0313405 | A1 | 12/2011 | Anderson et al. |
| 2012/0046522 | A1 | 2/2012 | Naito |
| 2012/0109186 | A1 | 5/2012 | Parrott et al. |
| 2012/0123441 | A1 | 5/2012 | Au et al. |
| 2012/0184955 | A1 | 7/2012 | Pivotto et al. |
| 2012/0239060 | A1 | 9/2012 | Orban, III et al. |
| 2012/0289974 | A1 | 11/2012 | Rogers et al. |
| 2013/0046318 | A1 | 2/2013 | Radgowski et al. |
| 2014/0005662 | A1 | 1/2014 | Shelton, IV |
| 2014/0005678 | A1 | 1/2014 | Shelton, IV et al. |
| 2014/0005708 | A1 | 1/2014 | Shelton, IV |
| 2014/0018821 | A1 | 1/2014 | Yeung et al. |
| 2014/0100558 | A1 | 4/2014 | Schmitz et al. |
| 2014/0107665 | A1 | 4/2014 | Shellenberger et al. |
| 2014/0257333 | A1 | 9/2014 | Blumenkranz |
| 2014/0276723 | A1 | 9/2014 | Parihar et al. |
| 2014/0309625 | A1 | 10/2014 | Okamoto et al. |
| 2015/0005786 | A1 | 1/2015 | Burbank |
| 2015/0051034 | A1 | 2/2015 | Cooper et al. |
| 2015/0150636 | A1 | 6/2015 | Hagn et al. |
| 2015/0157355 | A1 | 6/2015 | Price et al. |
| 2016/0045770 | A1 | 2/2016 | Yamada |
| 2016/0058443 | A1 | 3/2016 | Yates et al. |
| 2016/0151115 | A1 | 6/2016 | Karguth et al. |
| 2016/0157926 | A1 | 6/2016 | Boudreaux |
| 2016/0166342 | A1 | 6/2016 | Prisco et al. |
| 2016/0296219 | A1 | 10/2016 | Srivastava et al. |
| 2016/0338762 | A1 | 11/2016 | Krastins et al. |
| 2016/0361049 | A1 | 12/2016 | Dachs, II et al. |
| 2016/0361107 | A1 | 12/2016 | Zergiebel et al. |
| 2017/0022754 | A1 | 1/2017 | Nien et al. |
| 2017/0165017 | A1 | 6/2017 | Chaplin et al. |
| 2017/0172672 | A1 | 6/2017 | Bailey et al. |
| 2017/0207467 | A1 | 7/2017 | Shelton, IV et al. |
| 2017/0248194 | A1 | 8/2017 | Bae et al. |
| 2017/0265865 | A1 | 9/2017 | Burbank |
| 2018/0055583 | A1 | 3/2018 | Schuh et al. |
| 2018/0080533 | A1 | 3/2018 | Awtar |
| 2018/0214223 | A1 | 8/2018 | Turner |
| 2018/0229021 | A1 | 8/2018 | Donlon et al. |
| 2018/0271608 | A1* | 9/2018 | Ragosta .................. F16H 55/17 |
| 2019/0038282 | A1 | 2/2019 | Shelton, IV et al. |
| 2019/0099227 | A1 | 4/2019 | Rockrohr |
| 2019/0117325 | A1 | 4/2019 | Kishi |
| 2019/0125468 | A1 | 5/2019 | Adams |
| 2019/0159846 | A1 | 5/2019 | Yates et al. |
| 2019/0201022 | A1 | 7/2019 | Schoettgen et al. |
| 2019/0223960 | A1 | 7/2019 | Chaplin et al. |
| 2019/0231451 | A1 | 8/2019 | Lambrecht et al. |

(56) References Cited

U.S. PATENT DOCUMENTS

| | | | |
|---|---|---|---|
| 2019/0231464 | A1 | 8/2019 | Wixey et al. |
| 2019/0239965 | A1 | 8/2019 | Abbott |
| 2019/0298323 | A1 | 10/2019 | Lambrecht et al. |
| 2019/0328467 | A1 | 10/2019 | Waterbury et al. |
| 2020/0008828 | A1 | 1/2020 | Overmyer |
| 2020/0093554 | A1 | 3/2020 | Schuh et al. |
| 2020/0138473 | A1 | 5/2020 | Shelton, IV et al. |
| 2021/0093408 | A1 | 4/2021 | Carey et al. |
| 2021/0169591 | A1 | 6/2021 | Kapadia |
| 2021/0196408 | A1 | 7/2021 | Hoffman et al. |
| 2021/0196413 | A1 | 7/2021 | Inoue |
| 2021/0220001 | A1 | 7/2021 | Heiliger |
| 2021/0372508 | A1 | 12/2021 | Abbott |
| 2021/0401523 | A1 | 12/2021 | Suresh |
| 2021/0401524 | A1 | 12/2021 | Suresh et al. |
| 2022/0000572 | A1 | 1/2022 | Ragosta et al. |
| 2022/0015847 | A1 | 1/2022 | Kadokura |
| 2022/0039895 | A1 | 2/2022 | Adams et al. |
| 2022/0096067 | A1 | 3/2022 | Beckman et al. |
| 2022/0096082 | A1 | 3/2022 | Beckman et al. |
| 2022/0128133 | A1 | 4/2022 | Cooper et al. |
| 2022/0249182 | A1 | 8/2022 | Definis et al. |
| 2023/0045998 | A1 * | 2/2023 | Shelton, IV ..... A61B 17/07207 |
| 2023/0172680 | A1 | 6/2023 | Reid et al. |
| 2024/0197423 | A1 | 6/2024 | Ragosta et al. |
| 2024/0315792 | A1 | 9/2024 | Lambrecht et al. |
| 2024/0366329 | A1 | 11/2024 | Kadokura |
| 2025/0186147 | A1 | 6/2025 | Times et al. |

FOREIGN PATENT DOCUMENTS

| | | | |
|---|---|---|---|
| CN | 109069138 | A | 12/2018 |
| CN | 110269686 | A | 9/2019 |
| CN | 110584787 | A | 12/2019 |
| EP | 3476321 | A1 | 5/2019 |
| FR | 3014678 | A1 | 6/2015 |
| JP | H06114000 | A | 4/1994 |
| JP | H10249777 | A | 9/1998 |
| JP | 2005288590 | A | 10/2005 |
| WO | WO-9729690 | A1 | 8/1997 |
| WO | WO-2009039506 | A1 | 3/2009 |
| WO | WO-2012068156 | A2 | 5/2012 |
| WO | WO-2016073637 | A1 | 5/2016 |
| WO | WO-2016172299 | A1 | 10/2016 |
| WO | WO-2016189284 | A1 | 12/2016 |
| WO | WO-2017188851 | A1 | 11/2017 |
| WO | WO-2018013313 | A1 | 1/2018 |
| WO | WO-2018094191 | A1 | 5/2018 |
| WO | WO-2021041395 | A1 | 3/2021 |
| WO | WO-2021155707 | A1 | 8/2021 |
| WO | WO-2021192255 | A1 | 9/2021 |
| WO | WO-2023055684 | A2 | 4/2023 |

OTHER PUBLICATIONS

International Search Report and Written Opinion for Application No. PCT/US2022/044704, mailed Mar. 24, 2023, 16 pages.

Invitation to Pay Additional Fees and Partial International Search Report for PCT/US2022/044704, mailed Feb. 3, 2023, 10 pages.

Litvin F.L., et al., “Face Gear Drive with Helical Involute Pinion: Geometry, Generation by a Shaper and a Worm, Avoidance of Singularities and Stress Analysis,” NASA/CR—2005-213443, ARL-CR-557, Feb. 2005, 62 pages.

Litvin F.L., et al., “Handbook on Face Gear Drives with a Spur Involute Pinion,” NASA/CR-2000-209909, ARL-CR-447, Mar. 2000, 106 pages.

Smith L.J., “The Involute Helicoid and the Universal Gear,” Gear Technology, November/Dec. 1990, pp. 18-27.

Vertut, J., and Coiffet, P., “Robot Technology: Teleoperation and Robotics Evolution and Development,” English translation, Prentice-Hall, Inc., Inglewood Cliffs, NJ, USA 1986, vol. 3A, 332 pages.

* cited by examiner

MECHANISM FOR MANUALLY ACTIVATED TOOL ADJUSTMENT

CROSS-REFERENCE TO RELATED APPLICATIONS

This application is a U.S. national stage filing under 35 U.S.C. § 371 of International Application No. PCT/US2022/044704, entitled "Mechanism for Manually Activated Tool Adjustment." filed Sep. 26, 2022, which claims benefit of priority to U.S. Provisional Application Ser. No. 63/251,416, entitled "Mechanism for Manually Activated Tool Adjustment," filed Oct. 1, 2021, each of which is incorporated herein by reference in its entirety.

BACKGROUND

The embodiments described herein relate to medical devices, and more specifically to endoscopic tools. More particularly, the embodiments described herein relate to medical devices that include a manual drive that drives a tool drive member.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of a shaft. During an MIS procedure, the end effector, wrist mechanism, and the distal end of the shaft are inserted into a small incision or a natural orifice of a patient to position the end effector at a work site within the patient's body.

To enable the desired movement of the distal wrist mechanism and end effector, known instruments include motors, capstans, and cables. The cables extend through the shaft that connects the wrist mechanism to a mechanical structure. For teleoperated systems, the mechanical structure is typically motor driven and is operably coupled to a computer processing system to provide a user interface for a clinical user (e.g., a surgeon) to control the instrument as a whole, as well as the instrument's components and functions. Some teleoperated systems include a manual control separate from the motor driven aspects allowing a user some level of manual interaction with the medical device. Some known manual controls allow the user to override the motor driven control to manually open the jaws of an instrument (e.g., when a system fault occurs or during a power outage).

Patients benefit from continual efforts to improve the effectiveness of MIS methods and devices and in particular the manual interactions with the medical device. For example, making the manual controls easy to operate (e.g., without tools) allows for a surgeon to have more limited knowledge and parts (e.g., tools) for the manipulation of the device simplifying the surgical environment. In particular, placing the manual control on a surgical instrument in a way that the manual control can be operated while the instrument is mounted on an associated teleoperated manipulator without the need for using a separate tool decreases unnecessary steps and simplifies the operation of the manual control. For example, some known manual controls require the usage of Allen wrenches and multiple different steps. Thus, actuation of the manual control can be time consuming and complex. In another example, some known manual control systems include an exterior component that moves (e.g., rotates) during normal teleoperation of the instrument, which can cause unwanted distractions to the user due to movement of the exterior components. It can also be beneficial to reduce the size and the operating footprint of the mechanical structure of the medical device to allow for smaller MIS instruments overall and reduced occupancy of the operating space by the medical device giving surgeons a less cluttered environment. But producing small medical devices that implement the clinically desired functions for minimally invasive procedures can be challenging. In another example, reducing the cost and complexity of manufacturing the medical device allows greater accessibility to these medical devices. Reducing the cost allows for more reasonable disposability of the medical device after procedures. Reducing the complexity of the manufacturing further reduces the costs but also makes the medical device easier and faster to assemble. These design constraints together, as well as other medical device design requirements, provide a multi-faceted challenge.

Thus, a need exists for improved medical devices, including improved proximal mechanical structures that allow for simplified user manual control, limited exterior movement, and reduced size, cost, and complexity.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, a medical device includes a manual drive structure having a manual drive input member and a manual drive coupling member, a first tool drive member having a first motor drive input member, and a second tool drive member having a second motor drive input member. The first tool drive member is coupled to and driven by the manual drive input member via the manual drive coupling member. The second tool drive member is coupled to and driven by the manual drive input member via the manual drive coupling member.

In some embodiments, the medical device further includes a tool member, a first tension member, and a second tension member. The first tension member extends between the tool member and the first tool drive member whereby the first tool drive member articulates the first tool member via the first tension member. The second tension member extends between the first tool member and the second tool drive member whereby the second tool drive member articulates the tool member via the second tension member.

In some embodiments, the manual drive input member is coupled to and driven in a first direction by a drive force from the first tool drive member via the manual drive coupling member. On the condition that manual drive coupling member is driven in the first direction, the manual drive coupling member limits the drive force from driving the second tool drive member via the manual drive coupling member.

In some embodiments, the coupling between the first tool drive member and the manual drive input member via the manual drive coupling member allows torque transfer from the manual drive input member to the first tool drive member without allowing torque transfer from the first tool drive member to the manual drive input member.

In some embodiments, the manual drive coupling member is selectively adjustable between a first state and a second state. The first state is substantially free of engagement between the manual drive input member and the first tool drive member. In the second state the manual drive input member and the first tool drive member are engaged, whereby input into the manual drive input member produces movement in the first tool drive member in the second state.

In some embodiments, the manual drive coupling member includes a tool drive side coupling engagement member and a manual drive side coupling engagement member. In the second state the tool drive side coupling engagement member is engaged with the manual drive side coupling engagement member. In the first state the tool drive side coupling engagement member is dis-engaged with the manual drive side coupling engagement member. The manual drive side coupling engagement member includes an engagement portion and a non-engagement portion. The tool drive side coupling engagement member is engaged with the engagement portion in the first state and positioned adjacent to the non-engagement portion in the second state. In some embodiments, the tool drive side coupling engagement member is a first gear member, and the manual drive side coupling engagement member is a second gear member with the first gear member having the engagement portion and the non-engagement portion, whereby rotation of the manual drive input member rotates the second gear. The second gear member includes teeth along the engagement portion and no teeth along the non-engagement portion. The first gear member includes teeth, with the first gear member being positioned relative to the second gear member such that the teeth of the second gear member engage with the teeth of the first gear member in response to being in the second state and the teeth of the first gear member are adjacent to the non-engagement portion in response to being in the first state. The second gear member is biased to return to the first state on condition that a user is not applying a manual force to the manual drive input member.

In some embodiments, the medical device further includes a chassis and a housing. The manual drive input member, manual drive coupling member, the first tool drive member, the second tool drive member, and the housing are supported by the chassis. The manual drive input member extends external to the housing such that the manual drive input member provides a manual interface allowing a user to actuate the first tool drive member and the second tool drive member.

In some embodiments, a medical device includes a manual drive structure and a tool drive member. The manual drive structure includes a manual drive input member, and a manual drive coupling member. The tool drive member includes a first motor drive input member. The tool drive member is coupled to and driven by the manual drive input member via the manual drive coupling member. The coupling between the tool drive member and the manual drive input member via the manual drive coupling member allows torque transfer from the manual drive input member to the tool drive member without allowing torque transfer from the tool drive member to the manual drive input member.

In some embodiments, the manual drive input member is rotatable between a first state and a second state. In some embodiments, the manual drive coupling member includes a tool drive side coupling engagement member and a manual drive side coupling engagement member. The manual drive coupling member includes a tension member that extends between the tool drive side coupling engagement member and the manual drive side coupling engagement member. The tension member is wrapped around at least a portion of the tool drive side coupling engagement member. In the first state the tool drive side coupling engagement member is rotatable causing slack to form in the tension member engaged with the manual drive side coupling engagement member. As the manual drive input member is rotated from the first state to the second state the tension member is placed in tension thereby applying a torque to the tool drive side coupling engagement member causing the tool drive member to rotate. The manual drive input member is biased to return to the first state on condition that a user is not applying a manual force to the manual drive input member.

In some embodiments, a medical device includes a manual drive structure and a tool drive member. The manual drive structure includes a manual drive input member and a manual drive coupling member. The tool drive member includes a motor drive input member. The tool drive member is coupled to and driven by the manual drive input member via the manual drive coupling member. The manual drive coupling member is selectively adjustable between a first state and a second state. The first state is substantially free of engagement between the manual drive input member and the tool drive member. In the second state, the manual drive input member and the tool drive member are engaged, whereby input into the manual drive input member produces movement in the first tool drive member in the second state.

In some embodiments, the manual drive input member is rotatably movable with the movement resulting in adjustment between the first state and the second state. In some embodiments, the manual drive coupling member includes a tool drive side coupling engagement member and a manual drive side coupling engagement member. In the second state the tool drive side coupling engagement member is engaged with the manual drive side coupling engagement member. In the first state the tool drive side coupling engagement member is dis-engaged with the manual drive side coupling engagement member. The manual drive side coupling engagement member includes an engagement portion and a non-engagement portion. The tool drive side coupling engagement member is engaged with the engagement portion in the second state and positioned adjacent to the non-engagement portion in the first state. In some embodiments, the tool drive side coupling engagement member is a first gear member. The manual drive side coupling engagement member is a second gear member with the first gear member having the engagement portion and the non-engagement portion, whereby rotation of the manual drive input member rotates the second gear. The second gear member includes teeth along the engagement portion and no teeth along the non-engagement portion. The first gear member includes teeth and is positioned relative to the second gear member such that the teeth of the second gear member engage with the teeth of the first gear member in response to being in the second state. The teeth of the first gear member are adjacent to the non-engagement portion in response to being in the first state. In some embodiments, the second gear member is biased to return to the first state on condition that a user is not applying a manual force to the manual drive input member.

In some embodiments, the manual drive input member is movable in at least two degrees of freedom. The at least two degrees of freedom include rotation and slidability along a longitudinal axis with movement along the longitudinal axis transitioning the manual drive coupling member between the first state and the second state, the longitudinal axis being defined by an axis around which the manual drive input member is rotatable.

In some embodiments, the manual drive coupling member includes a tool drive side coupling engagement member and a manual drive side coupling engagement member. In the second state the tool drive side coupling engagement member is engaged with the manual drive side coupling engagement member. In the first state the tool drive side coupling engagement member is dis-engaged with the manual drive side coupling engagement member.

In some embodiments, the tool drive side coupling engagement member is a first gear member. The manual drive side coupling engagement member is a second gear member, whereby rotation of the manual drive input member rotates the second gear. The tool drive side coupling engagement member is a first mating surface. The manual drive side coupling engagement member is a second mating surface. In the first state the first mating surface and the second mating surface are separated and in the second state the first mating surface and the second mating surface are in contact, whereby rotation of the manual drive input member rotates the second mating surface via the first mating surface.

In some embodiments, a medical device includes a manual drive structure and a first tool drive member. The manual drive structure includes a manual drive input member, a manual drive coupling member, and a mechanical motor disconnect. The first tool drive member includes a first motor drive input member. The first tool drive member is coupled to and driven by the manual drive input member via the manual drive coupling member. On condition that the first tool drive member is driven by the manual drive input member, the mechanical motor disconnect separates the first motor drive input member from engagement with the first tool drive member.

Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIGS. 7B-7G show a portion of a mechanical structure of the medical device in a first operation state (FIG. 7B), a second operation state (FIG. 7C), a third operation state (FIG. 7D), a fourth operation state (FIG. 7E), a fifth operation state (FIG. 7F), and a sixth operation state (FIG. 7G).

DETAILED DESCRIPTION

Figure 1:
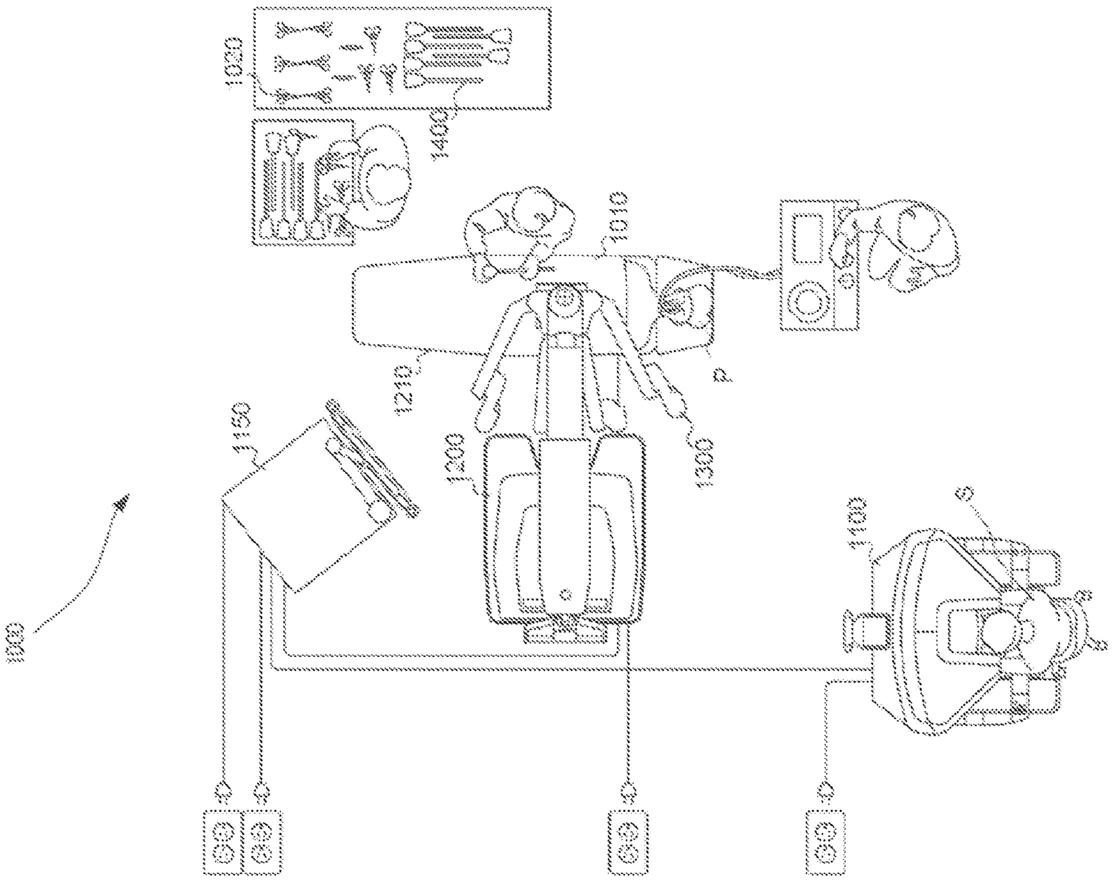
FIG. 1 is a plan view of a minimally invasive teleoperated medical system according to an embodiment being used to perform a medical procedure such as surgery.

The embodiments described herein can advantageously be used in a wide variety of grasping, cutting, and manipulating operations associated with minimally invasive surgery. In some embodiments, an end effector of the medical device can move with reference to the main body of the instrument in three mechanical DOFs, e.g., pitch, yaw, and roll (shaft roll). There may also be one or more mechanical DOFs in the end effector itself, e.g., two jaws, each rotating with reference to a clevis (2 DOFs) and a distal clevis that rotates with reference to a proximal clevis (one DOF).

The medical devices of the present application enable motion in three degrees of freedom (e.g., about a pitch axis, a yaw axis, and a grip axis) using multiple cables. In some embodiments, four cables are used, thereby reducing the total number of cables required, reducing the space required within the shaft and wrist, reducing overall cost, and enables further miniaturization of the wrist and shaft assemblies to promote MIS procedures. In some embodiments, six cables are used. It is appreciated that the various embodiments provided herein are adaptable to other systems with more or fewer cables based on the disclosure provided herein. Moreover, the instruments described herein include a manual drive structure that provide a manual input into the medical device such that the end effector and tools thereof can be actuated via the manual input. The various manual drive structures provided herein can allow for selective engagement, limiting the back drive between components, or driving two capstans from a single manual input. It should also be appreciated that some of the embodiments provided herein are adaptable to driving one capstan. In some embodiments the embodiments provided herein are adaptable to driving more than two capstans. These various functionalities apply to one or more of the embodiments described herein allow the medical device to be mounted on an associated teleoperated manipulator without the need for using a separate tool, instead being accessible and engaged by the hands of the user. Having the manual interface engage when desired removes undesirable distractions due to movement of the exterior features of the medical device thereby improving the usability of the medical device in a clinical setting.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

As used in this specification and the appended claims, the word "distal" refers to direction towards a work site, and the word "proximal" refers to a direction away from the work site. Thus, for example, the end of a medical device that is closest to the target tissue would be the distal end of the medical device, and the end opposite the distal end (i.e., the end manipulated by the user or coupled to the actuation shaft) would be the proximal end of the medical device.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below: A device may be otherwise oriented (e.g., rotated 90 degrees or at other orientations) and the spatially relative descriptors used herein interpreted accordingly. Likewise, descriptions of movement along (translation) and around (rotation) various axes includes various spatial positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

As used in this specification and the appended claims, the word "member" refers to a constituent portion of a larger structure or mechanism. A "member" can refer to an individual contiguous structure or multiple connected structures such as a mechanism.

Unless indicated otherwise, the terms apparatus, medical device, medical instrument, and variants thereof, can be interchangeably used.

Aspects of the invention are described primarily in terms of an implementation using a da Vinci® surgical system, commercialized by Intuitive Surgical, Inc. of Sunnyvale, California. Examples of such surgical systems are the da Vinci Xi® surgical system (Model IS4000), da Vinci X® Surgical System (Model IS4200), and the da Vinci Si® surgical system (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® surgical systems (e.g., the Model IS4000, the Model IS3000, the Model IS2000, the Model IS1200, the Model SP1099) are merely presented as examples, and they are not to be considered as limiting the scope of the inventive aspects disclosed herein. As applicable, inventive aspects may be embodied and implemented in both relatively smaller, hand-held, hand-operated devices that are not mechanically grounded in a world reference frame and relatively larger systems that have additional mechanical support that is grounded in a world reference frame.

FIG. 1 is a plan view illustration of a teleoperated surgical system 1000 that operates with at least partial computer assistance (a "telesurgical system"). Both telesurgical system 1000 and its components are considered medical devices. Telesurgical system 1000 is a Minimally Invasive Robotic Surgical (MIRS) system used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot) and an optional auxiliary equipment unit 1150. The manipulator unit 1200 can include an arm assembly 1300 and a surgical instrument tool assembly removably coupled to the arm assembly. The manipulator unit 1200 can manipulate at least one removably coupled instrument 1400 through a minimally invasive incision in the body or natural orifice of the patient P while the surgeon S views the surgical site and controls movement of the instrument 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of instruments 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
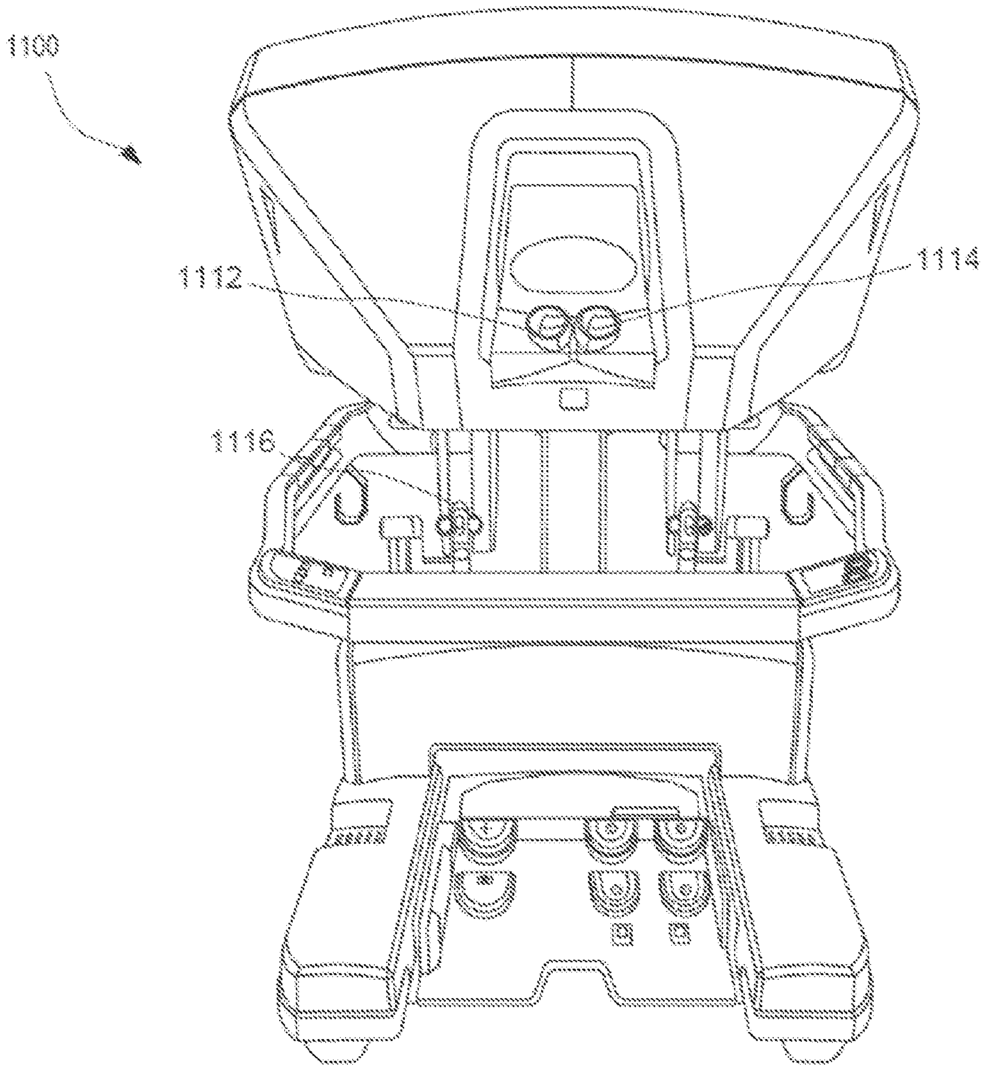
FIG. 2 is a perspective view of an optional auxiliary unit of the minimally invasive teleoperated surgery system shown in FIG. 1.

FIG. 2 is a perspective view of the control unit 1100. The user control unit 1100 includes a left eye display 1112 and a right eye display 1114 for presenting the surgeon S with a coordinated stereoscopic view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, strain, or tactile feedback sensors (not shown) or any combination of such sensations, from the instruments 1400 back to the surgeon's hand or hands through the one or more input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments, however, the user control unit 1100 and the surgeon S can be in a different room, a completely different building, or other location remote from the patient, allowing for remote surgical procedures.

Figure 3:
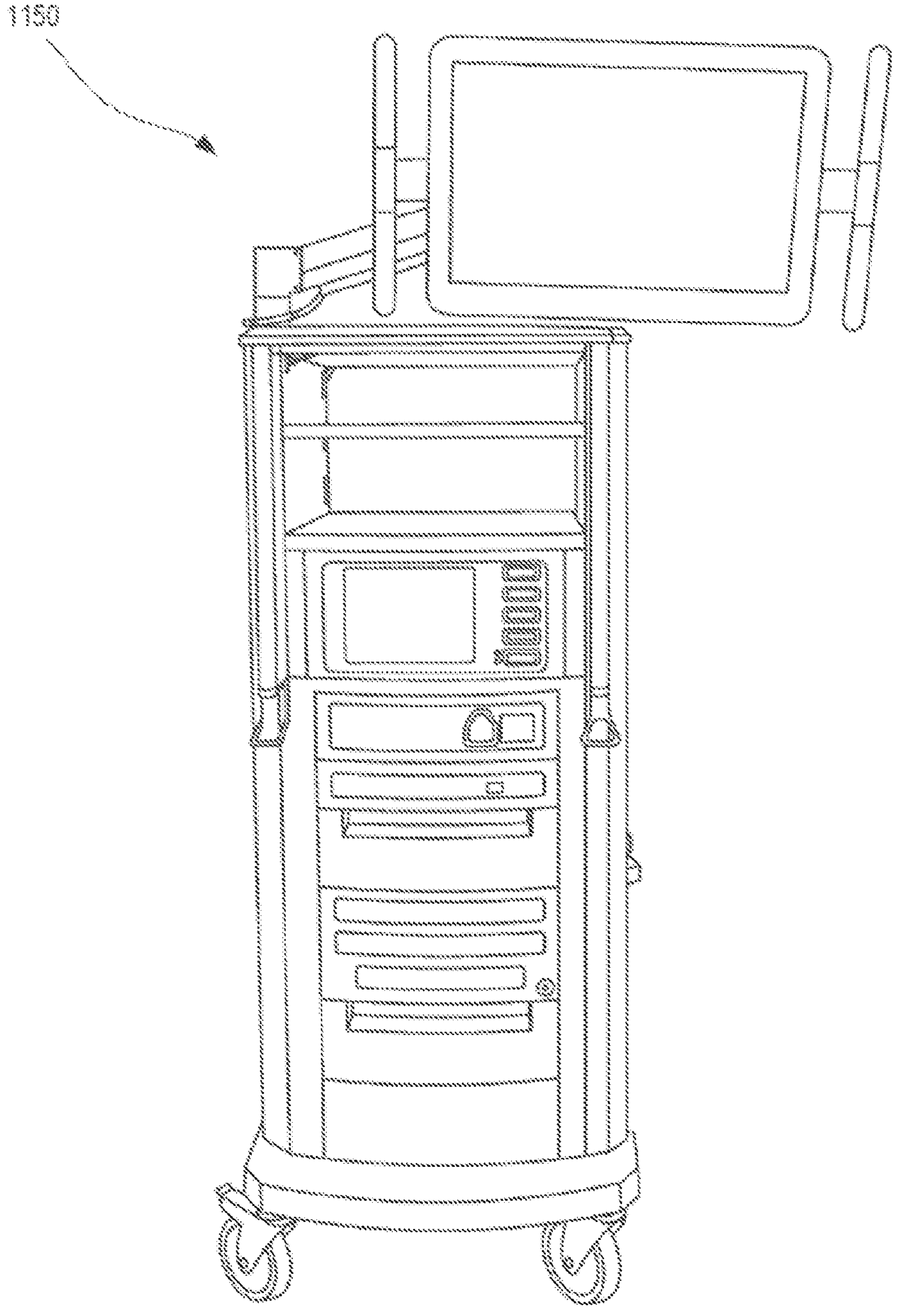
FIG. 3 is a perspective view of a user control console of the minimally invasive teleoperated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally (e.g., on the unit 1150 itself as shown, on a wall-mounted display) and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
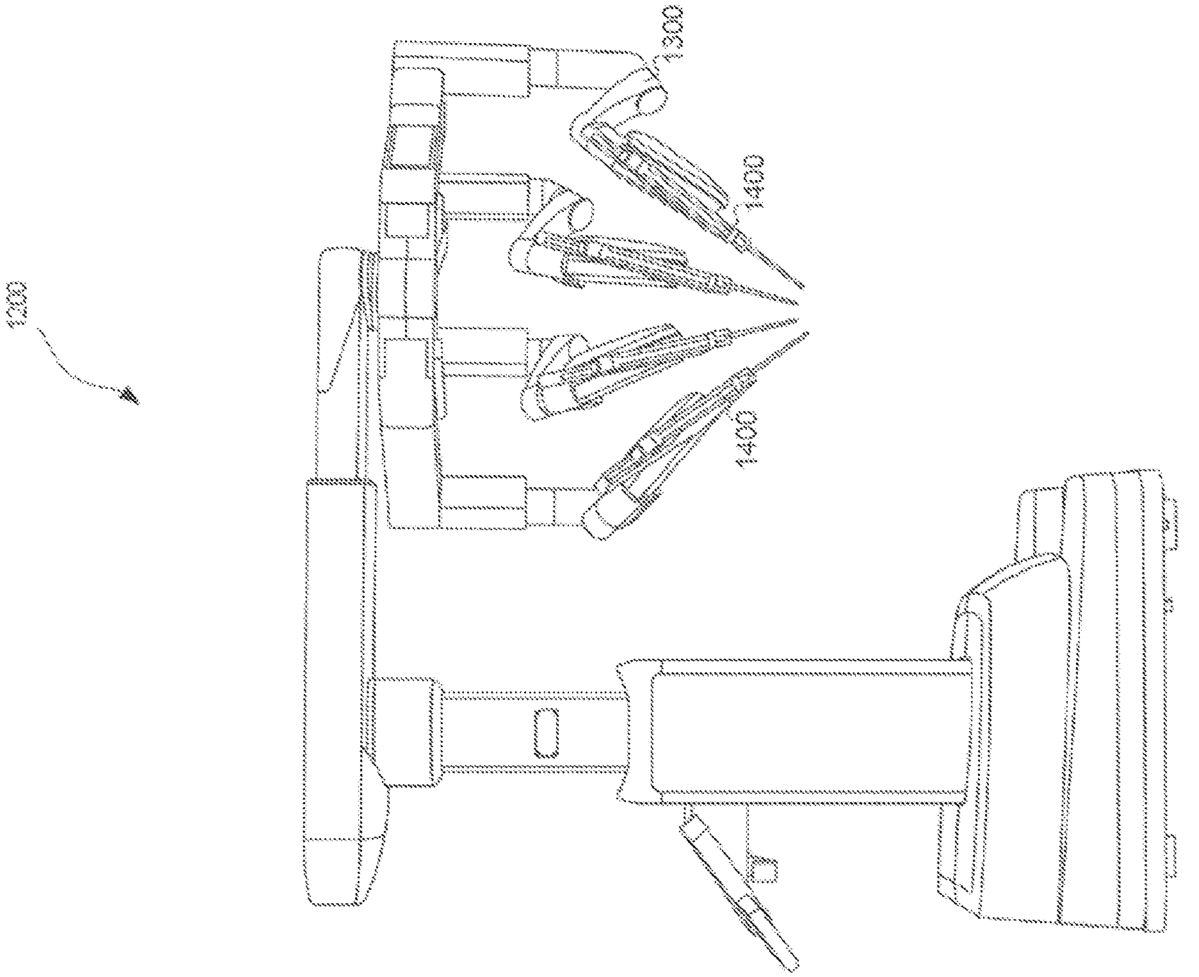
FIG. 4 is a front view of a manipulator unit, including a plurality of instruments, of the minimally invasive teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having one or more mechanical joints. Moreover, the instruments 1400 and the imaging device are positioned and manipulated through incisions or natural orifices in the patient P in a manner such that a center of motion remote from the manipulator and typically located at a position along the instrument shaft is maintained at the incision or orifice by either kinematic mechanical or software constraints. In this manner, the incision size can be minimized.

Figure 5:
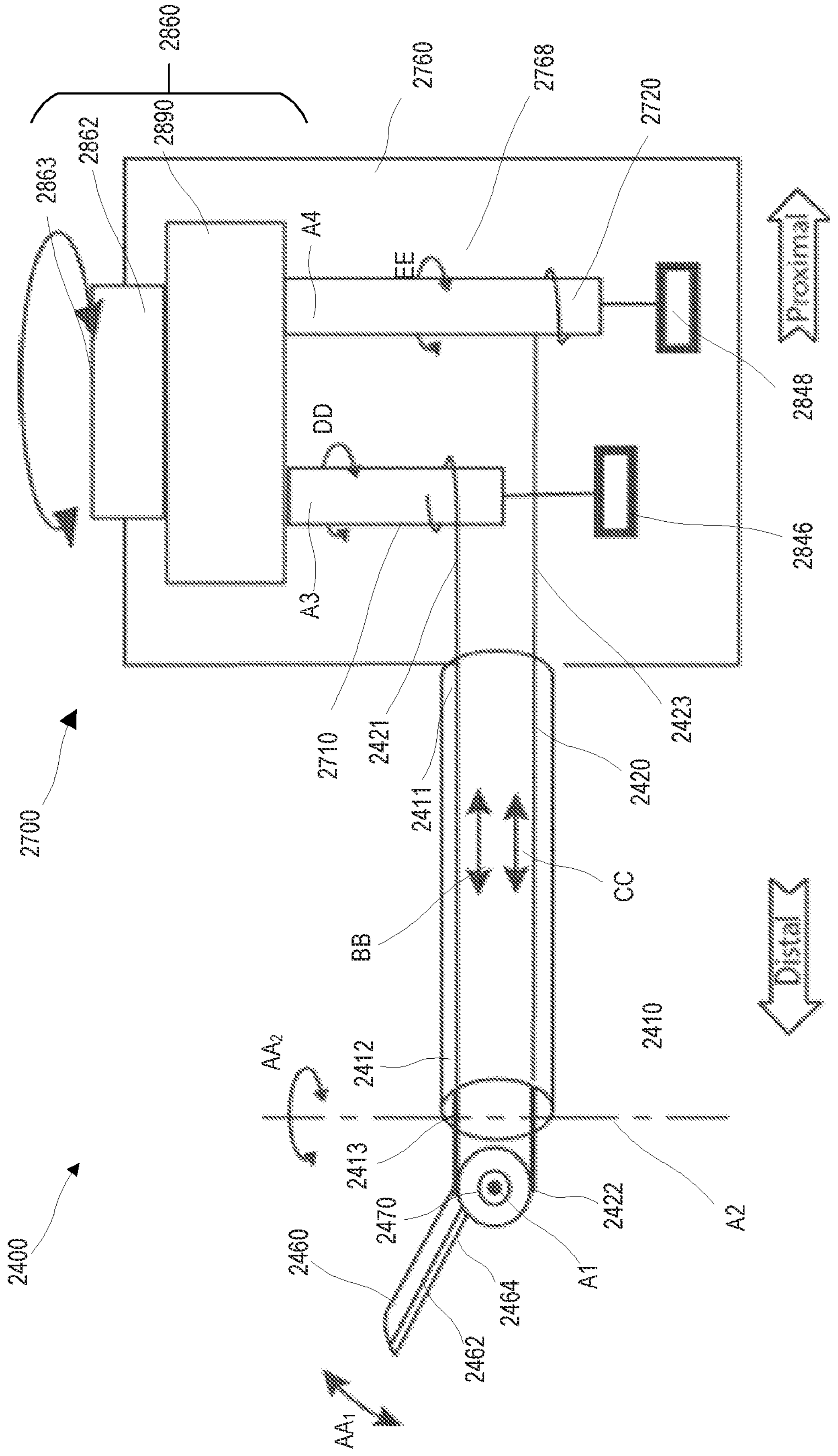
FIG. 5 is a diagrammatic illustration of a portion of a medical device for manual tool adjustment according to an embodiment.

FIG. 5 is a schematic illustration of a portion of a medical device 2400 according to an embodiment. The medical device 2400 includes a shaft 2410, a tension member 2420, an end effector 2460, and a mechanical structure 2700. The mechanical structure 2700 functions to receive one or more motor or manual input forces or torques and mechanically transmit the received forces or torques to move the end effector 2460. For example, one or more electric motors in a manipulator unit (e.g., the manipulator unit 1200) can provide an input to the mechanical structure 2700, which in turn transmits the input via the tension member 2420 to control the end effector 2460. Specifically, the mechanical structure includes a chassis 2768, a first tool drive member 2710, a second tool drive member 2720, and a manual drive structure 2860. The chassis 2768 provides the structural support for mounting or supporting and aligning the components of the mechanical structure 2700. For example, openings, protrusions, mounting brackets and the like can be defined in or on chassis 2768. In some embodiments, the chassis 2768 can include multiple portions, such as an upper chassis and a lower chassis. In some embodiments, a housing 2760 can optionally enclose at least a portion of the chassis 2768.

The first tool drive member 2710 is mounted to the mechanical structure 2700 (e.g., within the housing 2760) via a first tool drive member support member (not shown). For example, the first tool drive member support member can be a mount, shaft, or any other suitable support structure to secure the first tool drive member 2710 to the mechanical structure 2700. The first tool drive member 2710 includes a first motor drive input member 2846. The first motor drive input member 2846 can be connected to and receive mechanical input from an electric motor. The second tool drive member 2720 is mounted to the mechanical structure 2700 (e.g., within the housing 2760) via a second tool drive member support member (not shown). For example, the second tool drive member support member can be a mount, shaft, or any other suitable support structure to secure the second tool drive member 2720 to the mechanical structure 2700. The second tool drive member 2720 includes a second motor drive input member 2848. The first tool drive member 2710 can be operable to be rotated about an axis A3 in a direction DD, as shown in FIG. 5. The second tool drive member 2720 can be operable to be rotated about an axis A4. In some embodiments, the axis A4 is parallel to the axis A3.

The manual drive structure 2860 is connected to and drives the first tool drive member 2710 and the second tool drive member 2720. Thus, the first tool drive member 2710 can be driven by each of the manual drive structure 2860 and the first motor drive input member 2846. Similarly, the second tool drive member 2720 can be driven by each of the manual drive structure 2860 and the second motor drive input member 2848. Similarly stated, each tool drive member 2710, 2720 can be driven by a motor and a manual drive structure 2860. In this embodiment, the manual drive structure 2860 drives both the first tool drive member 2710 and the second tool drive member 2720. As discussed in more detail below, the tool drive members 2710, 2720 are connected to and manipulate an end effector 2460. Thus, the end effector 2460 can be manipulated by either a drive motor forming a part of the manipulator unit or the manual drive structure 2860.

The manual drive structure 2860 includes manual interface 2863, a manual drive input member 2862 and a manual drive coupling member 2890. The manual drive input member 2862 is mechanically connected to the manual interface 2863. The manual interface 2863 includes a portion that is exposed to the exterior of the medical device 2400. The user can engage the manual interface 2863 and manipulate the manual drive structure 2860 thereby manipulating the end effector 2460. The exposed portion manual interface 2863 can include any suitable structure for receiving the user's input force. For example, the manual interface 2863 can include a rotatable wheel, a rotatable knob, a push button, a slide, or other suitable mechanical structures that receive the user's input force and allows the manual drive structure 2860 to translate the user's input motion to an input on the tool drive members 2710, 2720 and thereby manipulate the end effector 2460.

The manual drive coupling member 2890 is connected to the manual drive input member 2862. The manual drive coupling member 2890 transmits the user's force from the manual drive input member 2862 to both the first tool drive member 2710 and the second tool drive member 2720. Because the first tool drive member 2710 and the second tool drive member 2720 can operate independently of one another (e.g., they can rotate independently, sometimes in the same direction, sometimes in opposite directions of one another, and sometimes one can be stationary while the other rotates), the manual drive coupling member 2890 also limits interference between one or more of the combinations of the first tool drive member 2710, the second tool drive member 2720, and the manual drive input member 2862. For example, the manual drive coupling member 2890 includes selectable engage-ability between the manual drive input member 2862 and one or both of the first tool drive member 2710 and the second tool drive member 2720. Such selectable engage-ability allows input forces to be transmitted between the manual drive input member 2862 and the first tool drive member 2710 and the second tool drive member 2720 in response to the manual drive coupling being in a first state but limiting or preventing forces to be transmitted between the manual drive input member 2862 and the first tool drive member 2710 and the second tool drive member 2720 in response to the manual drive coupling being in a second state.

In another example, the manual drive coupling member 2890 allows the input force to be transmitted from the manual drive input member 2862 toward the first tool drive member 2710 and the second tool drive member 2720, but not from the first tool drive member 2710 and the second tool drive member 2720 toward the manual drive input member 2862. Said another way, in some embodiments, the manual drive coupling member 2890 does not allow movement of either of the first tool drive member 2710 or the second tool drive member 2720 to cause movement of the manual drive input member 2862.

In another example, the manual drive coupling member 2890 allows input forces to be transmitted from the manual drive input member 2862 to the first tool drive member 2710 and the second tool drive member 2720. Additionally, the manual drive coupling member 2890 allows input forces to be transmitted from the first tool drive member 2710 and the second tool drive member 2720 to the manual drive input member 2862. The manual drive coupling member 2890, however, limits input forces at the first tool drive member 2710 from being transmitted to the second tool drive member 2720 through the manual drive coupling member 2890. The manual drive coupling member 2890 also limits input forces at the second tool drive member 2720 from being transmitted to the first tool drive member 2710 through the manual drive coupling member 2890.

The manual drive coupling member 2890 can include any suitable structure or components to perform the functions described herein. For example, in some embodiments, the manual drive coupling member 2890 can include a gear member or set of gears that can be engaged and disengaged from either (or both) of the first tool drive member 2710 and the second tool drive member 2720. In other embodiments clutches, tension members, hydraulics, slidable linkages, or any other suitable mechanism for transmitting force from the user to the tool drive members some of which are discussed herein and others that a person of ordinary skill in the art would apply based on the disclosure provided herein.

The tension member 2420 includes a first proximal portion 2421, a second proximal portion 2423 and a distal portion 2422. The first proximal portion 2421 and the second proximal portion 2423 are each coupled to the mechanical structure 2700, and the distal portion 2422 is coupled to the end effector 2460. The shaft 2410 includes a proximal end portion 2411 and a distal end portion 2412 and defines a passageway 2413 that extends lengthwise through the shaft between the proximal and distal end portions. In accordance with various embodiments, the tension member includes any member suitable for transmitting force between the tool drive members 2710, 2720 and the end effector. For example, the tension member can include one or more of a cable, band, strap, string, wire, tube, rod, etc. The tool drive members 2710, 2720 include one or more of capstans, winches, spools, or other suitable devices for containing, controlling, taking up, and dispensing the tension member 2420).

The end effector 2460 is rotatably coupled to the distal end portion 2412 of the shaft 2410 and includes at least one tool member 2462. The medical device 2400 is configured such that movement of the first proximal portion 2421 and the second proximal portion 2423 of the tension member 2420 produces movement of the tool member 2462 about a first axis of rotation A1 (which functions as the yaw axis: the term yaw is arbitrary), in a direction of arrows $AA_1$. In some embodiments, the medical device 2400 can include a wrist assembly including one or more links (not shown in FIGS. 5A-6B) that couples the end effector 2460 to the distal end portion 2412 of the shaft 2410. In such an embodiment, movement of the first proximal portion 2421 and the second proximal portion 2423 of the tension member 2420 can also produce movement of the wrist assembly about a second axis of rotation (not shown in FIG. 5, but which functions as the pitch axis: the term pitch is arbitrary) or both movement of the wrist assembly and the end effector 2460. See for example, U.S. provisional application No. 63/233,904 entitled "SURGICAL INSTRUMENT CABLE CONTROL AND ROUTING STRUCTURES" filed on Aug. 17, 2021, which is incorporated herein by reference in its entirety.

The tool member 2462 includes a contact portion 2464, and a drive pulley 2470. The contact portion 2464 is configured to engage or manipulate a target tissue during a surgical procedure. For example, in some embodiments, the contact portion 2464 can include an engagement surface that functions as a gripper, cutter, tissue manipulator, or the like. In this manner, the contact portion 2464 of the tool member 2462 can be actuated to engage or manipulate a target tissue during a surgical procedure. The tool member 2462 (or any of the tool members described herein) can be any suitable medical tool member. Moreover, although only one tool member 2462 is shown, in other embodiments, the medical device 2400 can include two or more moving tool members that cooperatively perform gripping or shearing functions.

The tension member 2420 is routed from the mechanical structure 2700 to the end effector 2460 and then back to mechanical structure 2700, and each individual end of the tension member 2420 is coupled to either the first tool drive member 2710 or the second tool drive member 2720 of the mechanical structure 2700. More specifically, the first proximal portion 2421 of the tension member 2420 is coupled to the first tool drive member 2710 of the mechanical structure 2700, the tension member 2420 extends from the first tool drive member 2710 along the shaft 2410, and the distal portion 2422 of the tension member 2410 is coupled to the end effector 2460. Although the tension member 2420 is shown extending within an interior passageway of the shaft 2410 in FIG. 5, in other embodiments, the tension member 2420 can be routed exterior to the shaft 2410. The tension member 2420 extends from the end effector 2460 along the shaft 2410 and the second proximal portion 2423 is coupled to the second tool drive member 2720 of the mechanical structure 2700. In other words, the two ends of a single tension member (e.g., 2420) are coupled to and actuated by two separate tool drive members of the mechanical structure 2700.

More specifically, the two ends of the tension member 2420 that are associated with opposing directions of a single degree of freedom are connected to two independent tool drive members 2710 and 2720. This arrangement, which is generally referred to as an antagonist drive system, allows for independent control of the movement of (e.g., pulling in or paying out) each of the ends of the tension member 2420. The mechanical structure 2700 produces movement of the tension member 2420, which operates to produce the desired articulation movements (pitch, yaw, or grip) at the end effector 2460. Accordingly, as described herein, the mechanical structure 2700 includes components and controls to move the first proximal portion 2421 of the tension member 2420 via the first tool drive member 2710 in a first direction (e.g., a proximal direction) and to move the second proximal portion 2423 of the tension member 2420) via the second tool drive member 2720 in a second opposite direction (e.g., a distal direction). The mechanical structure 2700 can also move both the first proximal portion of the tension member 2420) and the second proximal portion of the tension member 2420 in the same direction. In this manner, the mechanical structure 2700 can maintain the desired tension within the tension members to produce the desired movements at the end effector 2460).

In other embodiments, such as the one shown in FIG. 6 discussed in more detail below, any of the medical devices described herein can have the two ends of the tension member wrapped about a single tool drive member. This alternative arrangement, which is generally referred to as a self-antagonist drive system, operates the two ends of the tension member using a single drive motor.

In addition, in some alternative embodiments, the tension member 2420 includes two tension member segments, with each tension member segment having a distal end portion that is coupled to the end effector 2460 and a proximal end portion wrapped about a tool drive member—either separate tool drive members as in the antagonist drive arrangement or a single common tool drive member in the self-antagonist drive arrangement. Descriptions herein referring to the use of a single tension member 2420 incorporate the similar use of two separate tension member segments.

With the tension member 2420 coupled to the mechanical structure 2700) and to the end effector 2460, rotational movement produced by the first tool drive member 2710) causes the first proximal portion 2421 of the tension member 2420 to move in a direction BB (e.g., proximally or distally depending on the direction of rotation), as shown in FIG. 5. Similarly, rotational movement produced by the second tool drive member 2720 causes the second proximal portion 2423 of the tension member 2420 to move in the direction CC (e.g., proximally or distally depending on the direction of rotation), as shown in FIG. 5. In some embodiments, the first tool drive member 2710 can be operable to produce rotational movement about the axis A3, and the second tool drive member 2720 can similarly be operable to produce rotational movement about an axis A4 parallel to the axis A3. Thus, the first tool drive member 2710 can rotate in the direction of arrows DD and the second tool drive member 2720 can rotate in the direction of arrows EE in FIG. 5. When the first tool drive member 2710 rotates about the axis A3 in a first direction (clockwise or counter-clockwise), the second tool drive member 2720) can rotate independently about the axis A4 in either the same or the opposite direction (clockwise or counter-clockwise). In order to maintain tension in the tension member 2420, as one of the tool drive members 2710, 2720 pays out the tension member 2420, the other of the tool drive members 2710, 2720 pays in the tension member 2420. Depending on how the tension member s are routed to the various tool drive members, each of the individual tool drive members rotates such that the desired individual tension member pay-in or pay-out is performed to perform the desired end effector motion—grip, yaw, or pitch—either alone or in combination.

With each of the ends of the tension member 2420 coupled to a separate tool drive member, the movement of a first portion of the tension member 2420 can be directly controlled by one tool drive member (e.g., first tool drive member 2710) and movement of a second portion of the tension member 2420 can be directly controlled by the other tool drive member (e.g., second tool drive member 2720). Thus, the control of motion of the end effector 2460 in one direction is controlled by one tool drive member, and the control of motion of the end effector 2460 in the other direction is controlled by the other tool drive member. In this antagonist system, however, when the first tool drive member 2710 is controlling motion (i.e., applying tension to pull in the first proximal portion 2421 of the tension member 2420), the second proximal portion 2423 of the tension member is also under tension applied by the second tool drive member 2720. Maintaining tension applied by the non-driving tool drive member (i.e., the second tool drive member 2720) allows the non-driving tool drive member to immediately function as the driving tool drive member with no hysteresis in end effector control. The differing levels of tension applied by each tool drive member can also lead to improved control of the overall movement of the tension member. Thus, better control of the overall movement of the end effector 2460 can be achieved. For example, accurate rotation in yaw around axis A1 can be controlled. The first tool drive member 2710 can be actuated to produce a rotational movement about the axis A3 in the direction of the arrow DD such that the first proximal portion 2421 of the tension member is moved in a first direction along arrows BB. Simultaneously, the second tool drive member 2720 can be actuated to produce rotational movement about an axis parallel to the axis A3 in a direction relative to the first tool drive member 2710) such that the second proximal end portion 2423 of the tension member 2420 is moved in an opposite direction as the first proximal portion 2421 along arrows CC. Thus, the opposite movement of the first proximal portion 2421 and the second proximal portion 2423 causes the end effector 2460 to rotate (via the tension member 2420 connection to the end effector 2460) about the rotational axis A1 (e.g., yaw movement).

In a similar way, accurate rotation in pitch around a second axis A2 (e.g., pitch; orthogonal to the yaw axis A1 described above) can be controlled. As described above, the first tool drive member 2710 can be actuated to produce a rotational movement about the axis A3 in the direction of the arrow DD, while simultaneously the second tool drive member 2720 can be actuated to produce rotational movement about the axis A4 parallel to the axis A3 in the direction of the arrow EE such that the first proximal portion 2421 of the tension member and the second proximal portion 2423 of the tension member 2420 are moved together in the same direction (along arrows BB and CC, respectively). The movement of the first proximal portion 2421 and the second proximal portion 2423 in the same direction causes the end effector 2460 (or a wrist mechanism) to rotate (via the tension member 2420) connection to the end effector 2460) about a second rotation axis A2 in the direction of arrow $AA_2$ (e.g., pitch movement). Persons of skill in the art will understand that this action controls rotation around the second axis A2 in a first direction, and a similar action by an additional tension member (or tension member segments) (not shown) controls rotation around the second axis A2 in a second direction opposite the first direction. Thus an antagonistic control relationship between the tension member portions 2420 acting together and the additional tension member is used to accurately control end effector rotation in pitch. Alternatively, a resiliency such as a spring may be used to act against tension member portions 2420 to urge rotation around the second axis A2 in a direction opposite to the direction urged by tension member portions 2420. Thus, the combination of the first tool drive member 2710, the second tool drive member 2720, and the single tension member 2420 are operable to control the end effector 2460 of medical device 2400 in at least 2 DOFs (e.g., pitch and yaw).

While the independent operation of the first tool drive member 2710 and the second tool drive member 2720 allows for the complex manipulation of the end effector 2460 in the at least 2 DOFs discussed above, the manual drive structure 2860 allows for a limited manipulation of the end effector 2460 by the user without the use of the electronic motors. Like the manipulation of the tool member 2462 by the motors, the manual drive structure 2860 can cause rotation of the tool member 2462 in yaw around axis A1. The first tool drive member 2710 and the second tool drive member 2720 can be actuated by the manual drive structure 2860 instead of the motor to produce a rotational movement of the first tool drive member 2710 and the second tool drive member 2720. Specifically, this causes the first tool drive member 2710 to rotate about the axis A3 in the direction of the arrow DD such that the first proximal portion 2421 of the tension member is moved in a first direction along arrows BB. Simultaneously, the second tool drive member 2720 can be actuated to produce rotational movement about an axis parallel to the axis A3 in the same direction as the first tool drive member 2710) such that the second proximal end portion 2423 of the tension member 2420 is moved in an opposite direction as the first proximal portion 2423 along arrows CC. Thus, the opposite movement of the first proximal portion 2421 and the second proximal portion 2423 causes the end effector 2460) to rotate (via the tension member 2420 connection to the end effector 2460) about the rotational axis A1 (e.g., yaw movement). Thus, the manual drive structure 2860 allows for a single manual control to simultaneously actuate each of at least two inputs. This allows the inputs to manipulate one or more tools 2462. For example, the manual drive structure 2860 can open the jaws of a surgical instrument end effector for more effective jaw release such as in instances where the motor torque is insufficient.

This makes the manual control of the surgical device 2400 easy to operate with redundancy of tool opening operation. By providing the manual interface 2863 as described above, the manual drive structure can be controlled and operated while the instrument is mounted on an associated teleoperated manipulator without the need for using a separate tool, instead being accessible and engaged by the hands of the user. This limits the movement of and interaction with the manual control during normal teleoperation of the instrument thereby simplifying the work of the personnel by limiting undesirable distractions due to unnecessary or complicated engagement with the manual interface 2863 thereby improving the usability in a clinical setting.

Although the first proximal end 2421 and the second proximal end 2413 are shown as being portions of a single cable loop 2420 that is coupled to one tool member 2462, in other embodiments, any of the manual drive structures described herein can be used in connection with an end effector having two opposing tool members (e.g., jaws). In some such embodiments, a first tool drive member can be coupled to a first cable that drives a first jaw and a second tool drive member can be coupled to a second cable that drives a second jaw. In this manner, the manual drive structure can allow for a single manual input (e.g., via the manual interface 2863) to drive two tool drive members, each connected to a different jaw. Thus, the manual drive structure can drive both jaws, for example, to open both of the jaws in the event of a fault, loss of power, or other instance where manual control is desired.

Figure 6:
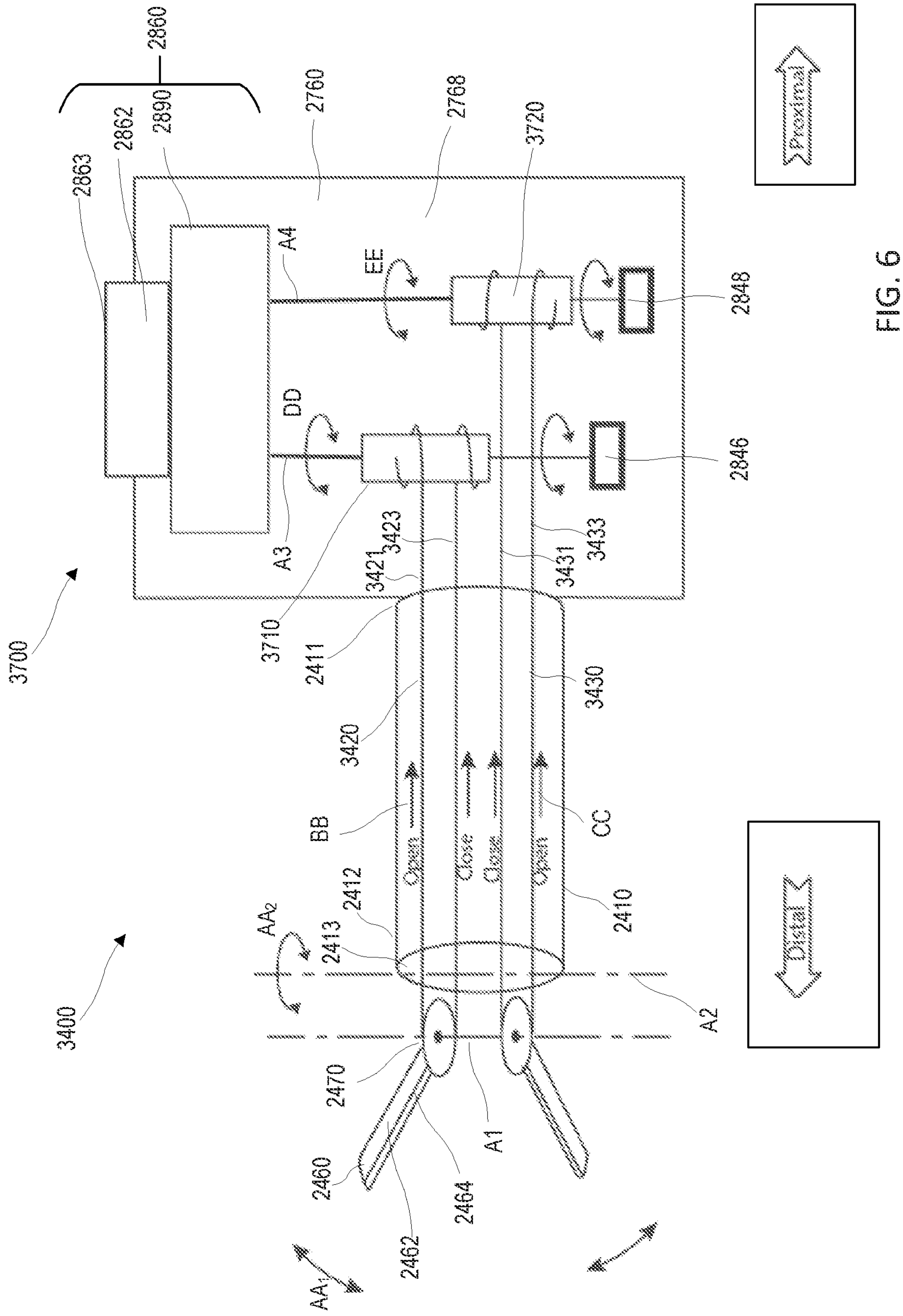
FIG. 6 is a diagrammatic illustration of a portion of a medical device for manual tool adjustment according to an embodiment.

FIG. 6 is a schematic illustration of a portion of a medical device 3400 with a self-antagonist drive system where the manual drive structure allows for manual control of two tool members. Like the medical device 2400 discussed above with regard to FIG. 5, medical device 3400 includes a shaft 2410, a first tension member 3420, a second tension member 3430, an end effector 2460, and a mechanical structure 3700. The mechanical structure 3700 functions to receive one or more motor or manual input forces or torques and mechanically transmit the received forces or torques to move the end effector 2460. The end effector 2460 and the shaft 2410 in medical device 3400 are similar to those disclosed above with respect to medical device 2400, and are therefore not described in detail below. The first tension member 3420, the second tension member 3430, and the mechanical structure 3700, however, differ in their respective structure and function in as much as medical device 2400 above is shown as an antagonist drive system and medical device 3400 is shown and disclosed as a self-antagonist drive system. For example, as shown in FIG. 6, the mechanical structure 3700 includes a chassis 2768, a first tool drive member 3710, a second tool drive member 3720, and a manual drive structure 2860. The first tool drive member 3710 and the second tool drive member 3720) are arranged relative to the mechanical drive structure 3700 and the medical device 3400 similar to the relationship between the first tool drive member 2710 and the second tool drive member 2720) and the mechanical structure 2700 and the medical device 2400 discussed above with respect to FIG. 5 with the exception that the first proximal end 3421 and the second proximal end 3423 of the first tension member 3420 are wrapped about a single tool drive member 3710 and the first proximal end 3431 and the second proximal end 3433 of the second tension member 3430) are wrapped around a second single tool drive member 3720.

The manual drive structures described herein can allow for selective transmission of the manual inputs and the forces applied by the motors or at the end effector of the device. For example, FIGS. 7A-7G are structural schematic illustrations of an embodiment of a medical device 4400 for manual tool adjustment. The medical device 4400 includes a shaft 4410, a tension member 4420, an end effector 4460, and a mechanical structure 4700. The mechanical structure 4700 functions to receive multiple motor and a manual input forces or torques and mechanically transmits the received forces or torques to move the end effector 4460. For example, the electric motors in a manipulator unit (e.g., the manipulator unit 1200) can provide an input to the mechanical structure 4700, which in turn transmits the input via the tension member 4420 to control the end effector 4460. Specifically, the mechanical structure includes a chassis 4768, a first tool drive member 4710, a second tool drive member 4720, and a manual drive structure 4860. The chassis 4768 provides the structural support for mounting or supporting and aligning the components of the mechanical structure 4700. For example, openings, protrusions, mounting brackets and the like can be defined in or on chassis 4768. In some embodiments, the chassis 4768 can include multiple portions, such as an upper chassis and a lower chassis. In some embodiments, a housing 4760) can optionally enclose at least a portion of the chassis 4768.

Figure 7A:
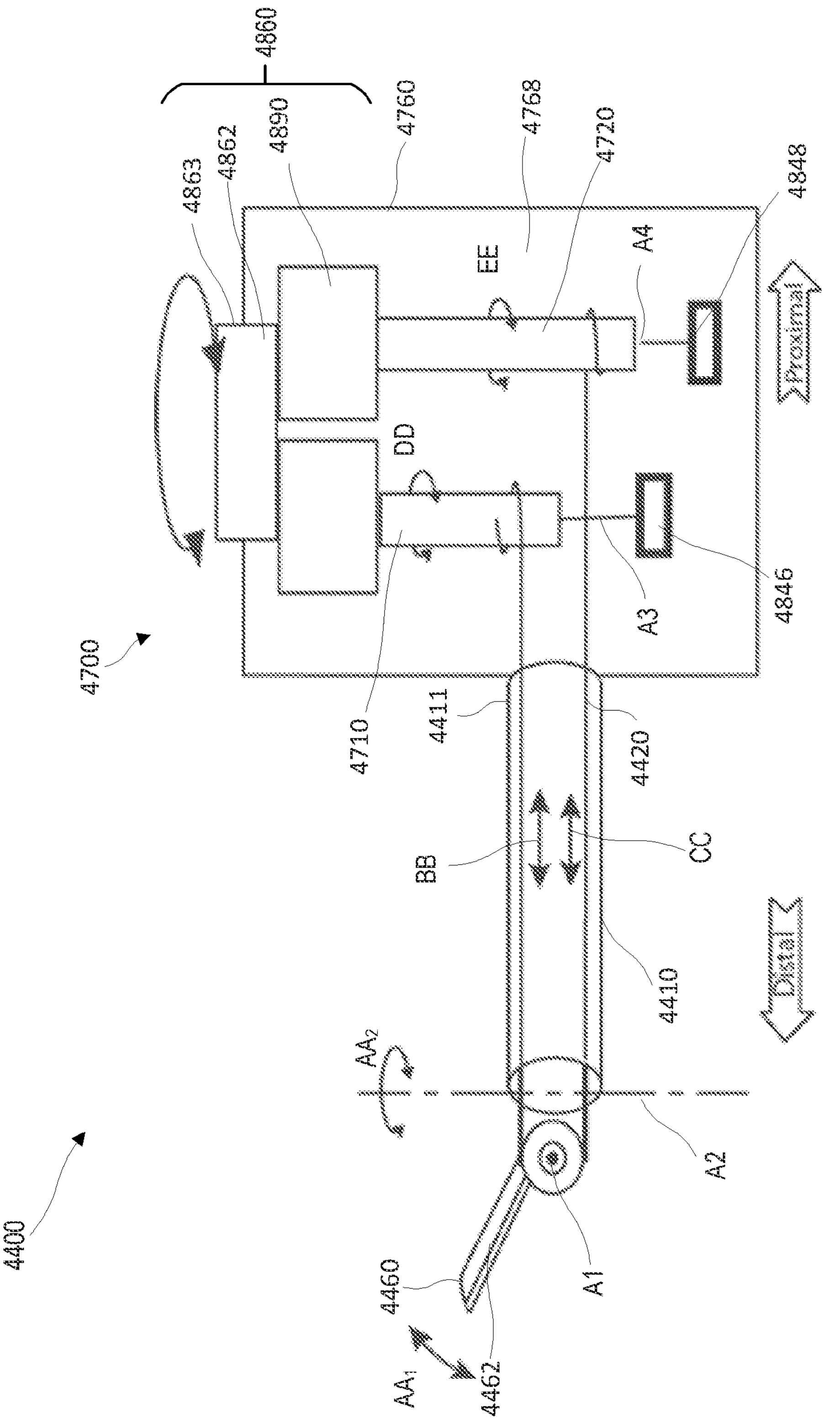
FIGS. 7A-G are a diagrammatic illustrations of a portion of a medical device for manual tool adjustment according to an embodiment, with FIG. 7A showing a portion of the medical device.

The first tool drive member 4710 is mounted to the mechanical structure 4700 (e.g., within the housing 4760) via a first tool drive member support member (not shown). For example, the first tool drive member support member can be a mount, shaft, or any other suitable support structure to secure the first tool drive member 4710 to the mechanical structure 4700. The first tool drive member 4710 includes a first motor drive input member 4846. The first motor drive input member 4846 can be connected to and receive mechanical input from an electric motor. The second tool drive member 4720 is mounted to the mechanical structure 4700 (e.g., within the housing 4760) via a second tool drive member support member (not shown). For example, the second tool drive member support member can be a mount, shaft, or any other suitable support structure to secure the second tool drive member 4720 to the mechanical structure 4700. The second tool drive member 4720) includes a second motor drive input member 4848. The first tool drive member 4710 can be operable to be rotated about an axis A3 in a direction DD, as shown in FIG. 7A. The second tool drive member 4720 can be operable to be rotated about an axis A4 in direction EE. In some embodiments, the axis A4 is parallel to the axis A3.

The manual drive structure 4860 is connected to and drives the first tool drive member 4710) and the second tool drive member 4720. Thus, the first tool drive member 4710) can be driven by each of the manual drive structure 4860 and the first motor drive input member 4846. Similarly, the second tool drive member 4720 can be driven by each of the manual drive structure 4860) and the second motor drive input member 4848. Similarly stated, each tool drive member 4710, 4720 can be driven by a motor and a manual drive structure 4860. In this embodiment, the manual drive structure 4860 drives both the first tool drive member 4710) and the second tool drive member 4720. As discussed in more detail below, the tool drive members 4710, 4720 are connected to and manipulate an end effector 4460. Thus, the end effector 4460 can be manipulated by either a drive motor forming a part of the manipulator unit or the manual drive structure 4860.

The manual drive structure 4860 includes manual interface 4863, a manual drive input member 4862 and a manual drive coupling member 4890. The manual drive input member 4862 is mechanically connected to the manual interface 4863. The manual interface 4863 includes a portion that is exposed to the exterior of the medical device 4400. The user can engage the manual interface 4863 and manipulate the manual drive structure 4860 thereby manipulating the end effector 4460. The exposed portion manual interface 4863 can include any suitable structure for receiving the user's input force. For example, the manual interface 4863 can include a rotatable wheel, a rotatable knob, a push button, a slide, or other suitable mechanical structures that receive the user's input force and allows the manual drive structure 4860 to translate the user's input motion to an input on the tool drive members 4710, 4720 and thereby manipulate the end effector 4460.

The manual drive coupling member 4890 is connected to the manual drive input member 4862. The manual drive coupling member 4890 transmits the user's force from the manual interface 4863 to both the first tool drive member 4710 and the second tool drive member 4720. Because the first tool drive member 4710 and the second tool drive member 4720 can operate independently of one another (e.g., they can rotate independently, sometimes in the same direction, sometimes in opposite directions of one another, and sometimes one can be stationary while the other rotates), the manual drive coupling member 4890 also limits interference between one or more of the combinations of the individual operations of the first tool drive member 4710, the second tool drive member 4720, and the manual drive input member 4862. For example, the manual drive coupling member 4890 allows input forces to be transmitted from the manual drive input member 4862 to the first tool drive member 4710 and the second tool drive member 4720. Additionally, the manual drive coupling member 4890 allows input forces to be transmitted from the first tool drive member 4710 and the second tool drive member 4720 to the manual drive input member 4862. The manual drive coupling member 4890, however, limits or isolates input forces at the first tool drive member 4710 from being transmitted to the second tool drive member 4720 through the manual drive coupling member 4890. The manual drive coupling member 4890 also limits or isolates input forces at the second tool drive member 4720 from being transmitted to the first tool drive member 4710) through the manual drive coupling member 4890.

In some embodiments, the manual drive coupling member 4890 is engaged between the manual drive input member 4862 and the first tool drive member 4710) and between the manual drive input member 4862 and the second tool drive member 4720 in a sufficiently direct linkage such that adjusting the manual drive input member 4862 results in direct engagement of the first tool drive member 4710 and the second tool drive member 4720. Stated another way, input into the manual drive input member 4862 in the drive direction results in direct movement of the first tool drive member 4710 and the second tool drive member 4720 without additional engagement, adjustment, or actuation of the manual drive coupling member 4890. This arrangement can also have the effect of back drive from the first tool drive member 4710 to the manual drive input member 4862 or from the second tool drive member 4720 to the manual drive input member 4862. The result would be, that automated motor usage during surgery could cause movement of the manual drive input member 4862 (which motion could be in the direction opposite of the actuation direction of the manual drive input member 4862).

Figure 7B:
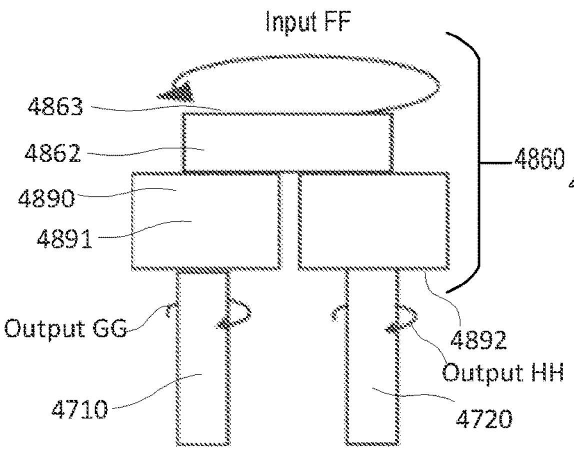
Figure 7C:
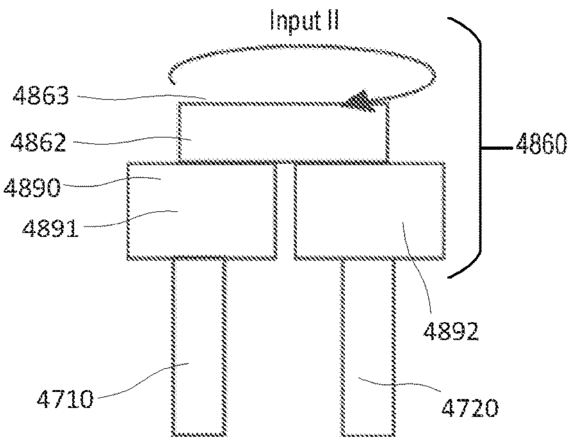

As shown in FIGS. 7B-7G, the manual drive coupling member 4890 includes a first manual tool drive coupler 4891 and a second manual tool drive coupler 4892. Each of the manual tool drive couplers 4891 and 4892 receives an input from the manual drive input member 4862. The first manual tool drive coupler 4891 transfers the input from the manual drive input member 4862 to the first tool drive member 4710 when the manual input member 4862 is moved in the actuation direction. The second manual tool drive coupler 4892 transfers the input from the manual drive input member 4862 to the second tool drive member 4720 when the manual input member 4862 is moved in the actuation direction. This operation is illustrated in FIG. 7B. Actuation input force (shown by the arrow FF) results in an output torque at the first tool drive member 4710 (shown by the arrow GG) and an output torque at the second tool drive member 4720 (shown by the arrow HH). Specifically, the manual tool drive coupler 4891 transfers at least a portion of the actuation input force from the manual input member 4862 to the first tool drive member 4710 and the manual tool drive coupler 4892 transfers at least a portion of the actuation input force from the manual input member 4862 to the second tool drive member 4720. Although the movement of the first tool drive member 4710 and the second tool drive member 4720 is shown as producing movement in one tool member 4462, in other embodiments, the manual drive structure 4860 can be used in connection with an end effector having two opposing tool members, and the movement of the first tool drive member 4710 can move a first jaw (e.g., tool member 4462) and the movement of the second tool drive member 4720 can move a second jaw (not shown). FIG. 7C shows the opposite operation. As shown, non-actuation input force (shown by the arrow II, which is in the opposite direction as the actuation input shown by the arrow FF, and which is not intended to produce movement of the end effector) has limited or no output to the tool drive members 4710, 4720. Specifically, the manual tool drive coupler 4891 substantially isolates the non-actuation input force applied to the manual input member 4862 from the first tool drive member 4710 and the manual tool drive coupler 4892 isolates the non-actuation input force applied to the manual input member 4862 from the second tool drive member 4720).

Figure 7D:
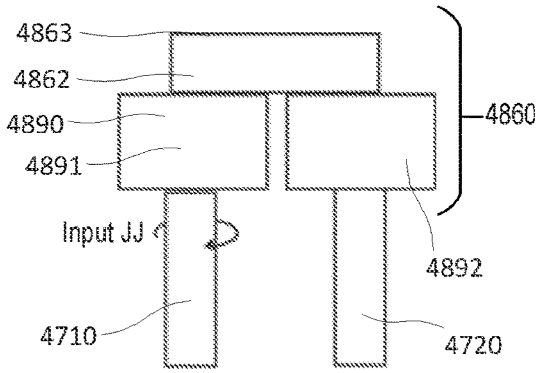
Figure 7E:
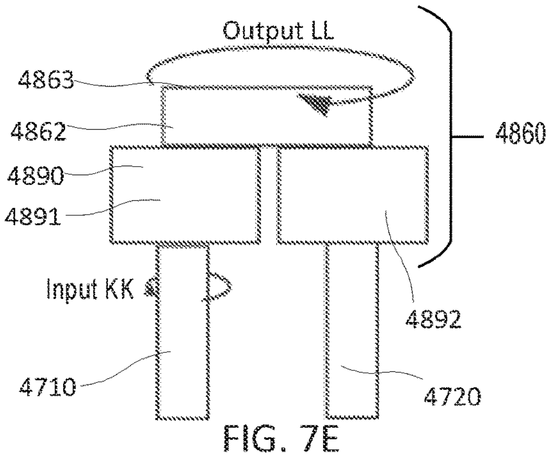
Figure 7F:
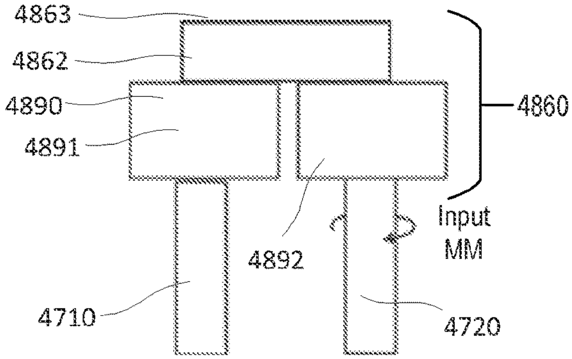
Figure 7G:
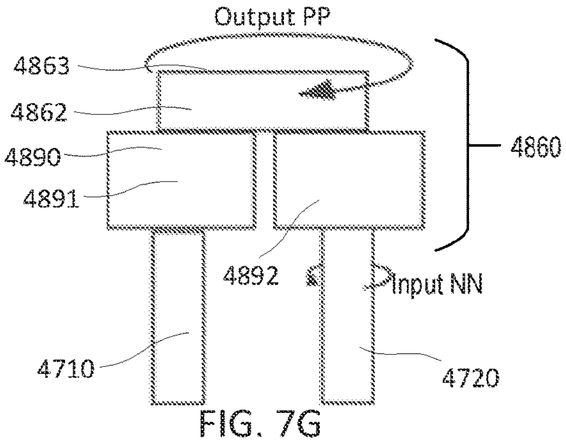

As shown in FIG. 7D, an input force (shown by the arrow JJ) at the first tool drive member 4710 (originating from a motor input) has limited or no output to the manual drive input member 4862 or the second tool drive member 4720. In this manner, motorized operation of the medical device 4400 (e.g., teleoperation) does not produce any movement of the manual drive input member 4862, thereby limiting any distraction to the user. As shown in FIG. 7E, an opposite input force (shown by the arrow KK in the opposite direction relative to the input force shown by JJ) at the first tool drive member 4710 (originating from a motor input) results in an output force, torque, or motion (shown by the arrow LL) in the manual drive input member 4862. However, because of the direction of the output force, torque, or motion (shown by the arrow LL), the result is similar to the result discussed above with regard to the non-actuation input force (shown by the arrow II), namely there is limited or no output to the second tool drive member 4720. Specifically, the manual tool drive coupler 4890 substantially isolates the input force applied to the first tool drive member 4710 from the second tool drive member 4720. As shown in FIG. 7F an input force (shown by the arrow MM) at the second tool drive member 4720) (originating from a motor input) has limited or no output to the manual drive input member 4862 or the first tool drive member 4710. As shown in FIG. 7G, an opposite input force (shown by the arrow NN in the opposite direction relative to the input force shown by MM) at the second tool drive member 4720 (originating from a motor input) results in an output force, torque, or motion (shown by the arrow LL) in the manual drive input member 4862. However, because of the direction of the output force, torque, or motion (shown by the arrow PP), the result is similar to the result discussed above with regard to the non-actuation input force (shown by the arrow II) namely there is limited or no output to the first tool drive member 4710. Specifically, the manual tool drive coupler 4890 substantially isolates the input force applied to the second tool drive member 4720 from the first tool drive member 4720.

The manual drive coupling member 4890 can include any suitable structure or components to perform the operations described herein. For example, the manual drive coupling member 4890 includes the first manual tool drive coupler 4891 and a second manual tool drive coupler 4892 that each include a one-way rotational engagement mechanism. Such engagement mechanisms can include one-way clutches (e.g., spring clutch, needle roller clutch, sprag clutch, etc.) ratchet and pawl mechanisms, or any other suitable device that transmits torque in one direction but rotates freely (i.e., without transmitting torque) in the opposite direction. In some examples, the first manual tool drive coupler 4891 and a second manual tool drive coupler 4892 can be engaged with the manual drive input member 4862 via any suitable power transmission mechanism, such as gears.

This arrangement makes the manual control of the surgical device 4400 easy to operate with redundancy of tool opening operation. By providing the manual interface 4863 as described above, the manual drive structure can be controlled and operated while the instrument is mounted on an associated teleoperated manipulator without the need for using a separate tool, instead being accessible and engaged by the hands of the user. This arrangement also limits the movement of and interaction with the manual control during normal teleoperation of the instrument thereby simplifying the work of the personnel by limiting unwanted distractions due to unnecessary or complicated engagement with the manual interface 4863 thereby improving the usability in a clinical setting.

Figure 8:
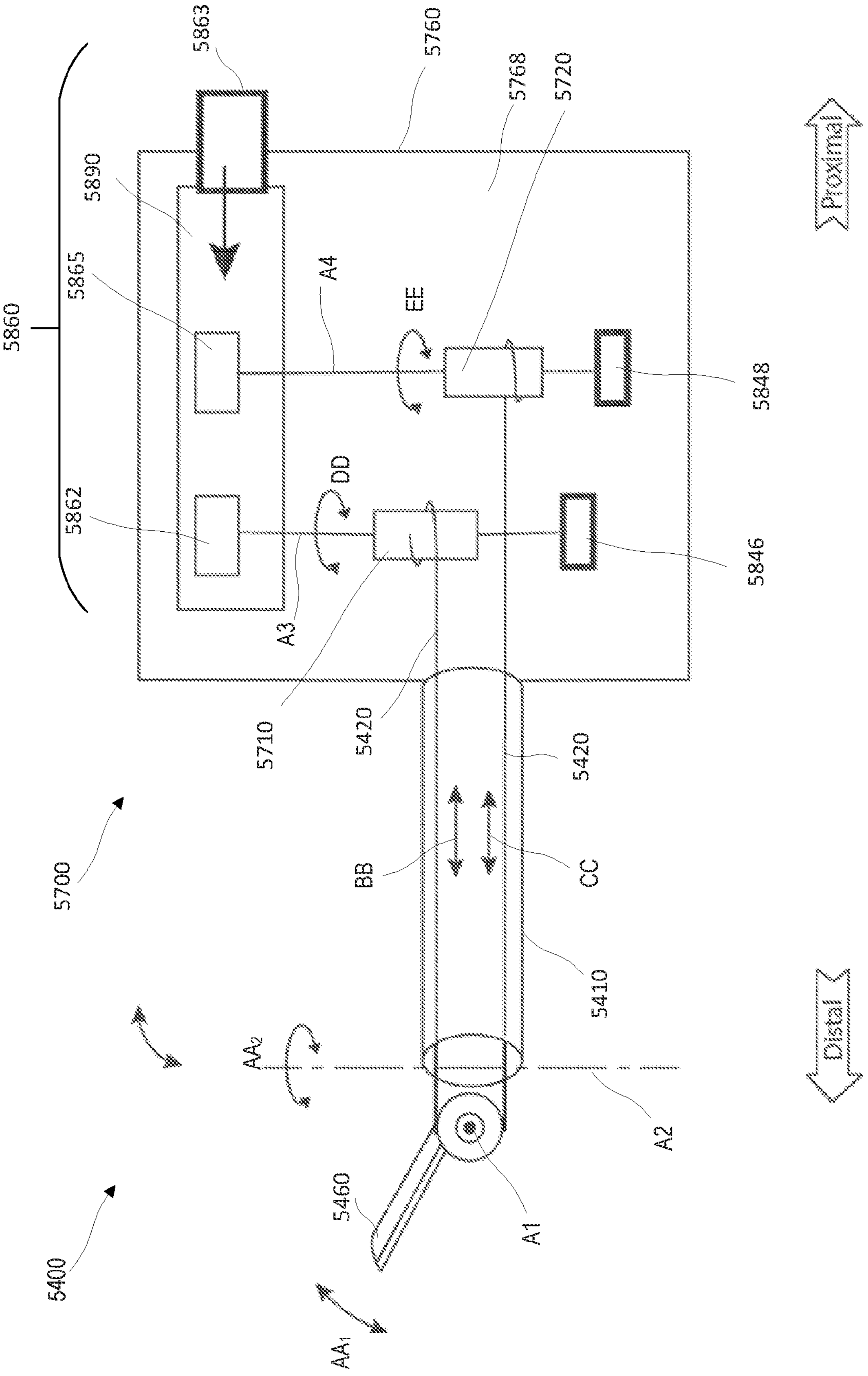
FIG. 8 is a diagrammatic illustration of a portion of a medical device for manual tool adjustment according to an embodiment.

FIG. 8 is a structural schematic illustration of an embodiment of a medical device 5400 for manual tool adjustment. The medical device 5400 includes a shaft 5410, a tension member 5420, an end effector 5460, and a mechanical structure 5700. The mechanical structure 5700 functions to receive multiple motor input forces or torques and a manual input force or torque and mechanically transmits the received forces or torque to move the end effector 5460. For example, the electric motors in a manipulator unit (e.g., the manipulator unit 1200) can provide an input to the mechanical structure 5700, which in turn transmits the input via the tension member 5420 to control the end effector 5460. Specifically, the mechanical structure includes a chassis 5768, a first tool drive member 5710, a second tool drive member 5720, and a manual drive structure 5860. The chassis 5768 provides the structural support for mounting or supporting and aligning the components of the mechanical structure 5700. For example, openings, protrusions, mounting brackets and the like can be defined in or on chassis 5768. In some embodiments, the chassis 5768 can include multiple portions, such as an upper chassis and a lower chassis. In some embodiments, a housing 5760) can optionally enclose at least a portion of the chassis 5768.

The first tool drive member 5710 is mounted to the mechanical structure 5700 (e.g., within the housing 5760) via a first tool drive member support member (not shown). For example, the first tool drive member support member can be a mount, shaft, or any other suitable support structure to secure the first tool drive member 5710 to the mechanical structure 5700. The first tool drive member 5710) includes a first motor drive input member 5846. The first motor drive input member 5846 can be connected to and receive mechanical input from an electric motor. The second tool drive member 5720 is mounted to the mechanical structure 5700 (e.g., within the housing 5760) via a second tool drive member support member (not shown). For example, the second tool drive member support member can be a mount, shaft, or any other suitable support structure to secure the second tool drive member 5720 to the mechanical structure 5700. The second tool drive member 5720) includes a second motor drive input member 5848. The first tool drive member 5710 can be operable to be rotated about an axis A3 in a direction DD, as shown in FIG. 8. The second tool drive member 5720 can be operable to be rotated about an axis A4.

The manual drive structure 5860 is connected to and drives one or more of the first tool drive member 5710) and the second tool drive member 5720. However, the manual drive structure 5860) is structured such that the first tool drive member 5710) and the second tool drive member 5720) are limited in their ability to drive the first manual drive input member 5862 or the second manual drive member 5865 regardless of the torque direction applied to the first tool drive member 5710) and the second tool drive member 5720. Thus, at least one (or both) of the first manual drive input member 5862 and second manual drive input member 5865 is isolated from the forces applied to the first tool drive member 5710 and the second tool drive member 5720) while the first tool drive member 5710) and the second tool drive member 5720) are subject to the forces applied to the first manual drive input member 5862 and the second manual drive input member 5865, as described herein. This allows the first tool drive member 5710 to be driven by each of the manual drive structure 5860 and the first motor drive input member 5846. Similarly or alternatively, the second tool drive member 5720 can be driven by each of the manual drive structure 5860) and the second motor drive input member 5848. As discussed in more detail below, the tool drive members 5710, 5720 are connected to and manipulate an end effector 5460. Thus, the end effector 5460) can be manipulated by either a drive motor forming a part of the manipulator unit or the manual drive structure 5860.

The manual drive structure 5860 includes manual interface 5863 and a manual drive coupling member 5890). The manual drive coupling member 5890 includes a first manual drive input member 5862 and a second manual drive input member 5865. The manual interface 5863 is the portion of the manual drive structure 5860 that extends out of the housing 5760) and provides tactile feature through which the user can apply an input force. The manual drive coupling 5890) is mechanically connected to the manual interface 5863 such that at least one (or both) of the first manual drive input member 5862 and the second manual drive input member 5865 receives the users applied force via the manual interface 5863. The user can engage the manual interface 5863 and manipulate the manual drive coupling member 5890 which in turn manipulates one or more of the tool drive members 5710, 5720 thereby manipulating the end effector 5460. The exposed portion manual interface 5863 can include any suitable structure for receiving the user's input force. For example, the manual interface 5863 can include a rotatable wheel, a rotatable knob, a push button, a slide, a lever or other suitable mechanical structures that receive the user's input force and allows the manual drive structure 5860 to translate the user's input motion to an input on the tool drive members 5710, 5720) and thereby manipulate the end effector 5460 in the absence of the automated motor discussed above.

In some embodiments, the manual drive coupling member 5890) transmits the user's input force to both the first tool drive member 5710 and the second tool drive member 5720.

The manual drive coupling member 5890 includes one or more manual drive input members 5862, 5865 corresponding to the number of tool drive members being driven. The manual drive input members 5862, 5865 are operable to transmit the input force (from the manual interface 5863) to respective tool drive members. For example, the first manual drive input member 5862 drives the first tool drive member 5710 and the second manual drive input member 5865 drives the second tool drive member 5720. In another example, a single manual drive input member (e.g., 5862) drives a single tool drive member 5710 (e.g., such an arrangement could be used in a self-antagonistic embodiments).

In embodiments, in which the manual drive coupling member 5890 transmits the user's force to both the first tool drive member 5710 and the second tool drive member 5720, the manual drive coupling member 5890 also isolates forces applied to the first tool drive member 5710 and the second tool drive member 5720 from driving forces through the manual drive coupling member 5890. This allows the first tool drive member 5710 and the second tool drive member 5720 to operate independently of one another (e.g., they can rotate independently, sometimes in the same direction, sometimes in opposite directions of one another, and sometimes one can be stationary while the other rotates) and independently of the movement of or force applied to the manual drive interface 5863. For example, in certain operating configurations, the manual drive coupling member 5890 directs the input force to be transmitted from the manual interface 5863 through the manual drive input member 5862 toward the first tool drive member 5710. However, forces from the first tool drive member 5710 toward the manual drive input member 5862 are limited by the manual drive coupling member 5890 structure. Said another way, in some embodiments, the manual drive coupling member 5890 limits torque from the tool drive members (e.g., 5710, 5720) to cause movement of the manual drive input member 5862 (referred to herein as "back drive").

The manual drive coupling member 5890 can include any suitable structure or components to limit back drive as described herein. For example, the manual drive coupling member 5890 can include gearing that provides a singular direction of force transfer, tension members that transfer force under tension but not compression, hydraulic systems that provide singular direction of force transfer, or any other suitable mechanism the limits back drive. One example of a back drive limiting system is further disclosed in the manual drive structure 11860 shown and described in FIGS. 33-35.

Limiting the back drive makes the manual control of the surgical device 5400 easy to operate while providing redundancy of tool opening operation. By providing the manual interface 5863 and limiting the back drive thereto as described above, the manual drive structure can be controlled and operated while the instrument is mounted on an associated teleoperated manipulator without the need for using a separate tool, instead being accessible and engaged by the hands of the user. Limiting the back drive limits undesirable distractions due to movement of the exterior features of the medical device 5400 e.g., the manual interface 5863 thereby improving the usability of the medical device 5400 in a clinical setting.

Figure 9:
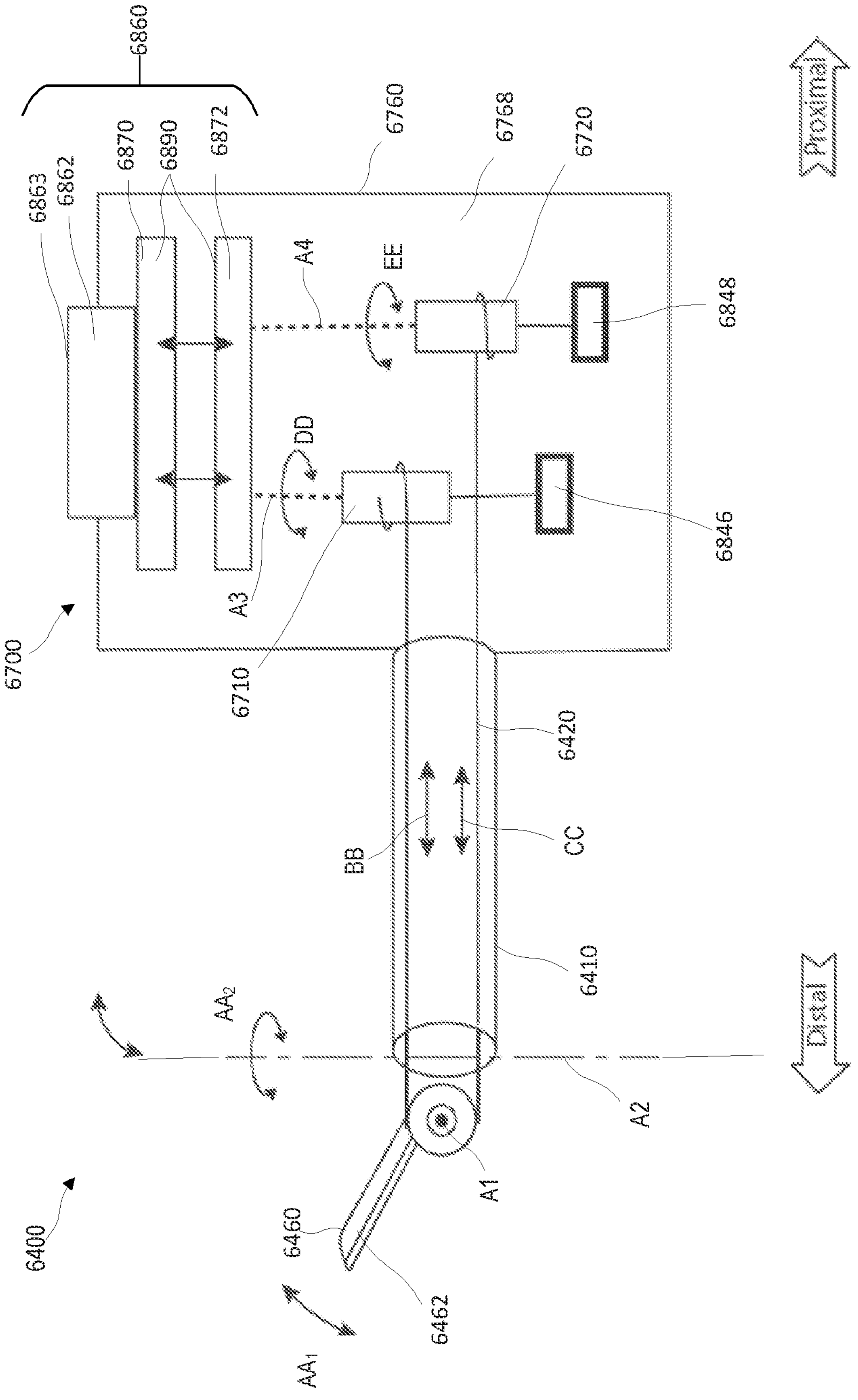
FIG. 9 is a diagrammatic illustration of a portion of a medical device for manual tool adjustment according to an embodiment.

FIG. 9 is a structural schematic illustration of an embodiment of a medical device 6400 for manual tool adjustment. The medical device 6400 includes a shaft 6410, a tension member 6420, an end effector 6460, and a mechanical structure 6700. The mechanical structure 6700 functions to receive multiple motor input forces or torques and a manual input force or torque and mechanically transmits the received forces or torque to move the end effector 6460. For example, the electric motors in a manipulator unit (e.g., the manipulator unit 1200) can provide an input to the mechanical structure 6700, which in turn transmits the input via the tension member 6420 to control the end effector 6460. Specifically, the mechanical structure includes a chassis 6768, a first tool drive member 6710, a second tool drive member 6720, and a manual drive structure 6860. The chassis 6768 provides the structural support for mounting or supporting and aligning the components of the mechanical structure 6700. For example, openings, protrusions, mounting brackets and the like can be defined in or on chassis 6768. In some embodiments, the chassis 6768 can include multiple portions, such as an upper chassis and a lower chassis. In some embodiments, a housing 6760 can optionally enclose at least a portion of the chassis 6768.

The first tool drive member 6710 is mounted to the mechanical structure 6700 (e.g., within the housing 6760) via a first tool drive member support member (not shown). For example, the first tool drive member support member can be a mount, shaft, or any other suitable support structure to secure the first tool drive member 6710 to the mechanical structure 6700. The first tool drive member 6710 includes a first motor drive input member 6846. The first motor drive input member 6846 can be connected to and receive mechanical input from an electric motor. The second tool drive member 6720 is mounted to the mechanical structure 6700 (e.g., within the housing 6760) via a second tool drive member support member (not shown). For example, the second tool drive member support member can be a mount, shaft, or any other suitable support structure to secure the second tool drive member 6720 to the mechanical structure 6700. The second tool drive member 6720 includes a second motor drive input member 6848. The first tool drive member 6710 can be operable to be rotated about an axis A3 in a direction DD, as shown in FIG. 9. The second tool drive member 6720 can be operable to be rotated about an axis A4.

The manual drive structure 6860 is connected to and drives one or more of the first tool drive member 6710 and the second tool drive member 6720. The manual drive structure 6860 provides a selectably engageable connection with one or more of the first tool drive member 6710) and the second tool drive member 6720) for force transfer. Thus, force transfer between the manual drive structure 6860 and the tool drive members is limited in response to the manual drive structure 6860 being in a disengaged state. Force transfer between the manual drive structure and the tool drive members occurs in response to the manual drive structure 6860 being in an engaged state.

The first tool drive member 6710 can be driven by each of the manual drive structure 6860 and the first motor drive input member 6846. Similarly or alternatively, the second tool drive member 6720 can be driven by each of the manual drive structure 6860 and the second motor drive input member 6848. As discussed in more detail below, the tool drive members 6710, 6720 are connected to and manipulate an end effector 6460. Thus, the end effector 6460 can be manipulated by either a drive motor forming a part of the manipulator unit or the manual drive structure 6860. Although the movement of the first tool drive member 6710 and the second tool drive member 6720 is shown as producing movement in one tool member 6462, in other embodiments, the manual drive structure 6860 can be used in connection with an end effector having two opposing tool members, and the movement of the first tool drive member

6710 can move a first jaw (e.g., tool member 6462) and the movement of the second tool drive member 6720 can move a second jaw (not shown).

The manual drive structure 6860 includes manual interface 6863 and a manual drive coupling member 6890. The manual drive coupling member 6890 includes a manual drive side coupler 6870 and a tool drive side coupler 6872. The manual drive side coupler 6870 is mechanically engaged with the manual interface 6863 allowing the manual interface 6863 to manipulate the manual drive side coupler 6870. The tool drive side coupler 6872 is mechanically engaged with one or more of the tool drive members (e.g., 6710, 6720).

The manual interface 6863 includes a portion that is exposed to the exterior of the medical device 6400. The user can engage the manual interface 6863 and manipulate the manual drive structure 6860 which can engage with and manipulate the tool drive members and thereby manipulate the end effector 6460. The exposed portion manual interface 6863 can include any suitable structure for receiving the user's input force. For example, the manual interface 6863 can include a rotatable wheel, a rotatable knob, a push button, a slide, or other suitable mechanical structures that receive the user's input force and allows the manual drive structure 6860 to translate the user's input motion at the manual interface 6863 to an input on the tool drive members 6710, 6720 and thereby manipulate the end effector 6460. The manual interface 6863 transmits the user's input force to one or more of the drive members, such that the end effector can be manipulated in the absence of the automated motor input.

The manual drive side coupler 6870 and the tool drive side coupler 6872 are movable between states such that in a first state they are disengaged limiting the transfer of the user's force between one another and therefor to the respective tool drive members. In a second state they are engaged allowing the transfer of the user's force between one another and therefor to one or more of the tool drive members. For example, in some configurations, the manual interface 6863 is engaged by the user causing the manual drive side coupler 6870 to engage with the tool drive side coupler 6872. Further manipulation of the manual interface 6863 causes a force that is transmitted across the manual drive side coupler 6870 and the tool drive side coupler 6872 thereby driving one or more of the tool drive members (e.g., 6710, 6720). Similarly stated, the user can manipulate the manual interface 6863 in a first operation or with a first input force that causes the manual drive side coupler 6870 to engage with the tool drive side coupler 6872. The user can then manipulate the manual interface 6863 in a second operation or with a second input force that is transmitted across the manual drive side coupler 6870 and the tool drive side coupler 6872 to drive one or more of the tool drive members.

In embodiments, in which the manual drive coupling member 6890 transmits the user's force from the manual interface 6863 to both the first tool drive member 6710 and the second tool drive member 6720, the selective engageability of the manual drive coupling member 6890 also limits interference between one or more of the combinations of the operations of the first tool drive member 6710, the second tool drive member 6720, and the manual drive input member 6862. This allows the first tool drive member 6710 and the second tool drive member 6720 to operate independently of one another (e.g., they can rotate independently, sometimes in the same direction, sometimes in opposite directions of one another, and sometimes one can be stationary while the other rotates).

The manual drive coupling member 6890 can include any suitable structure or components to perform the operations described herein. For example, selectively engageable mechanisms can include gear sets that can be moveably engaged and disengaged from either (or both) of the first tool drive member 6710 and the second tool drive member 6720, clutches, hydraulics, mechanisms with a free range of movement allowing for disengagement in the range and engagement when the range is overcome, and any other suitable mechanism. Examples of such mechanisms are further detailed with respect to the embodiments shown and described in FIGS. 10-21, 22-25, and 26-32 disclosed below.

Selective engageability of the manual control of the surgical device 6400 allows for simplicity in operation of the device while providing redundancy of tool opening operation. By providing the manual interface 6863 and selective engageability as described above, the manual drive structure can be controlled and operated while the instrument is mounted on an associated teleoperated manipulator without the need for using a separate tool, instead being accessible and engaged by the hands of the user. Having the manual interface engage when desired removes undesirable distractions due to movement of the exterior features of the medical device 6400, thereby improving the usability of the medical device 6400 in a clinical setting.

Figure 10:
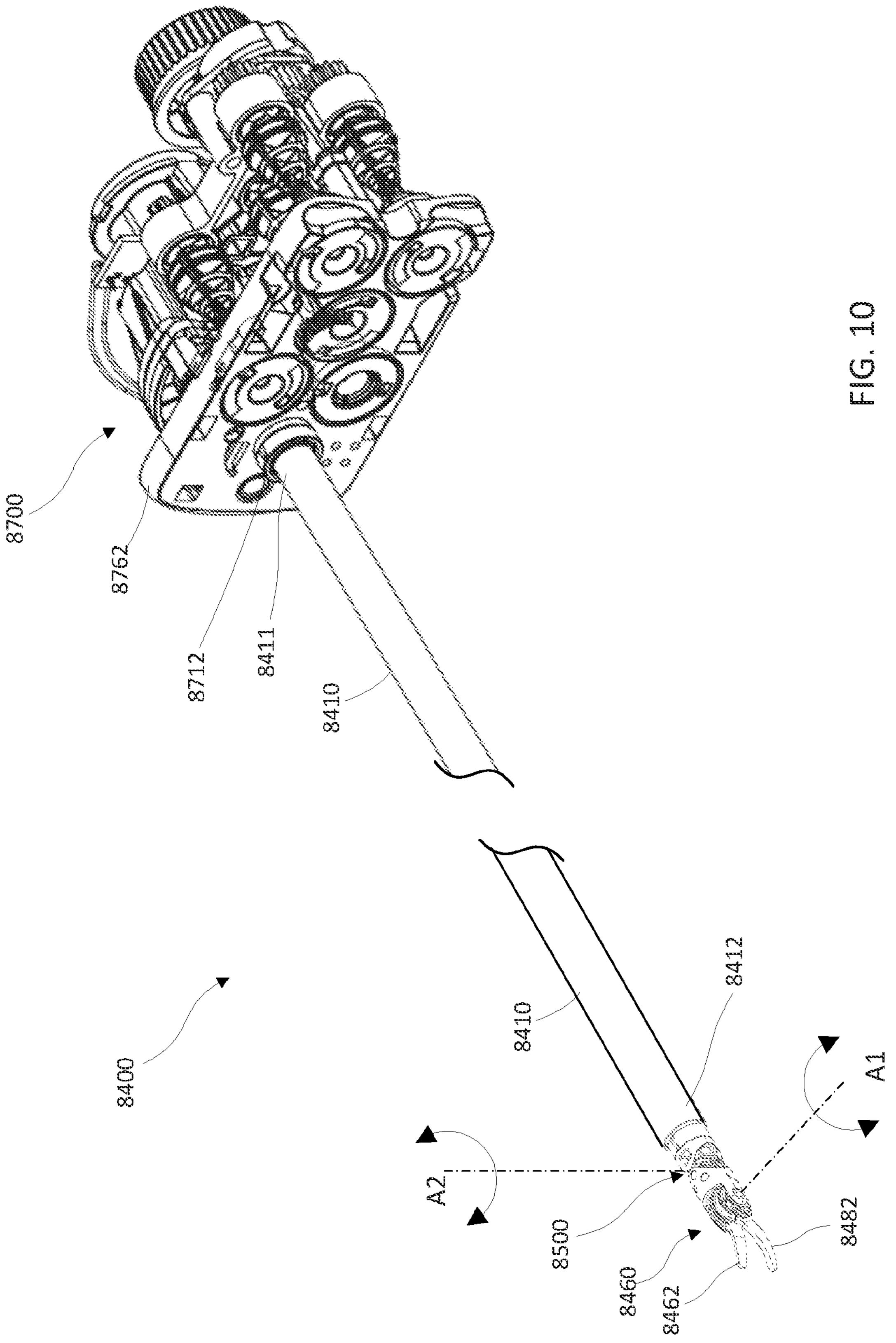
FIG. 10 is a perspective view of a portion of a medical device for manual tool adjustment according to an embodiment.

FIGS. 10-21B are various views of a medical device 8400, according to an embodiment. In some embodiments, the medical device 8400 or any of the components therein are optionally parts of a surgical system that performs surgical procedures, and which can include a manipulator unit, a series of kinematic linkages, a series of cannulas, or the like. The medical device 8400 (and any of the instruments described herein) can be used in any suitable surgical system, such as the MIRS system 1000 shown and described above. As shown in FIG. 10, the medical device 8400 includes a proximal mechanical structure 8700, a shaft 8410, a distal wrist assembly, and a distal end effector 8460).

The shaft 8410 can be any suitable elongated shaft that couples the wrist assembly to the mechanical structure 8700. Specifically, the shaft 8410 includes a proximal end 8411 that is coupled to the mechanical structure 8700, and a distal end 8412 that is coupled to the wrist assembly (e.g., a proximal link of the wrist assembly).

Figure 13:
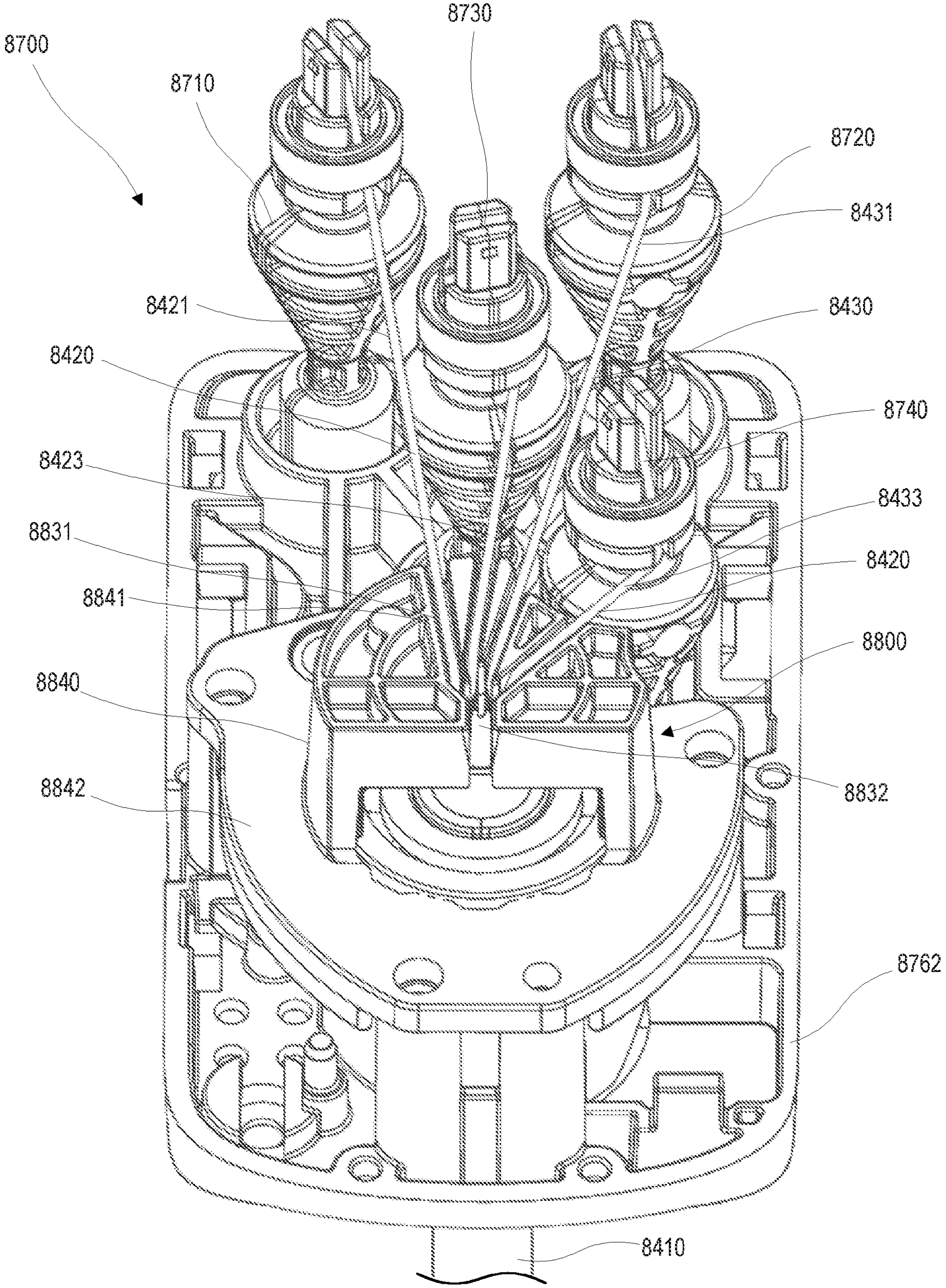
FIG. 13 is a top perspective view of cable routing of the medical device of FIG. 10.

As shown in FIG. 13, the medical device 8400 also includes a first cable 8420) and a second cable 8430) that couple the proximal mechanical structure 8700 to the distal wrist assembly and end effector 8460. The medical device 8400 is configured such that movement of the first cable 8420 and second cable 8430 produces rotation of the end effector 8460) about a first axis of rotation A1 (which functions as the yaw axis: the term yaw is arbitrary) of the wrist assembly about a second axis of rotation A2 (which functions as the pitch axis: the term pitch is arbitrary), a cutting rotation of the tool members of the end effector 8460 about the first axis of rotation, or any combination of these movements. Additional examples and disclosures of the actuation of the end effector with relevant axes, e.g., first axis A1 and second axis A2, are further disclosed in U.S. provisional application No. 63/233,904 entitled "SURGICAL INSTRUMENT CABLE CONTROL AND ROUTING STRUCTURES" filed on Aug. 17, 2021, which is incorporated herein by reference in its entirety. Changing the pitch or yaw of the medical device 8400 can be performed by manipulating the cables in a similar manner as that described above for the instruments 2400, 3400, 4400, and 5400. Thus, the specific movement of each of the cables to accomplish the desired motion is not described below.

The first cable 8420 includes a first proximal portion 8421, a second proximal portion 8423, and a distal portion (not shown). The second cable 8430 includes a first proximal portion 8431, a second proximal portion 8433, and a distal portion (not shown). As described in more detail below; the first proximal portion 8421 is coupled to a first capstan 8710 and the second proximal portion 8423 is coupled to a third capstan 8730. The distal portion of the first cable 8420 is coupled to a first tool member 8462. Thus, movement of the first capstan 8710 and the third capstan 8730 can move the proximal end portions of the first cable 8420 to move the first tool member 8462. The first proximal portion 8431 is coupled to a second capstan 8720 and the second proximal portion 8423 is coupled to a fourth capstan 8740. The distal portion of the second cable 8430 is coupled to a second tool member 8482. Thus, movement of the second capstan 8720 and the fourth capstan 8740 can move the proximal end portions of the second cable 8430 to move the second tool member 8482.

The end effector 8460 can be operatively coupled to the mechanical structure 8700 such that the tool members 8462 and 8482 rotate about the first axis of rotation A1. For example, a drive pulley (not shown) of the first tool member 8462 is coupled to the distal end of the first cable 8420 such that a tension force exerted by the first cable 8420 produces a rotation torque about the first axis A1. Similarly, a drive pulley (not shown) of the second tool member 8482 is coupled to the distal end of the second cable such that a tension force exerted by the second cable produces a rotation torque about the first rotation axis A1. In this manner, the tool member 8462 and the tool member 8482 can be actuated to engage or manipulate a target tissue during a surgical procedure.

Figure 11:
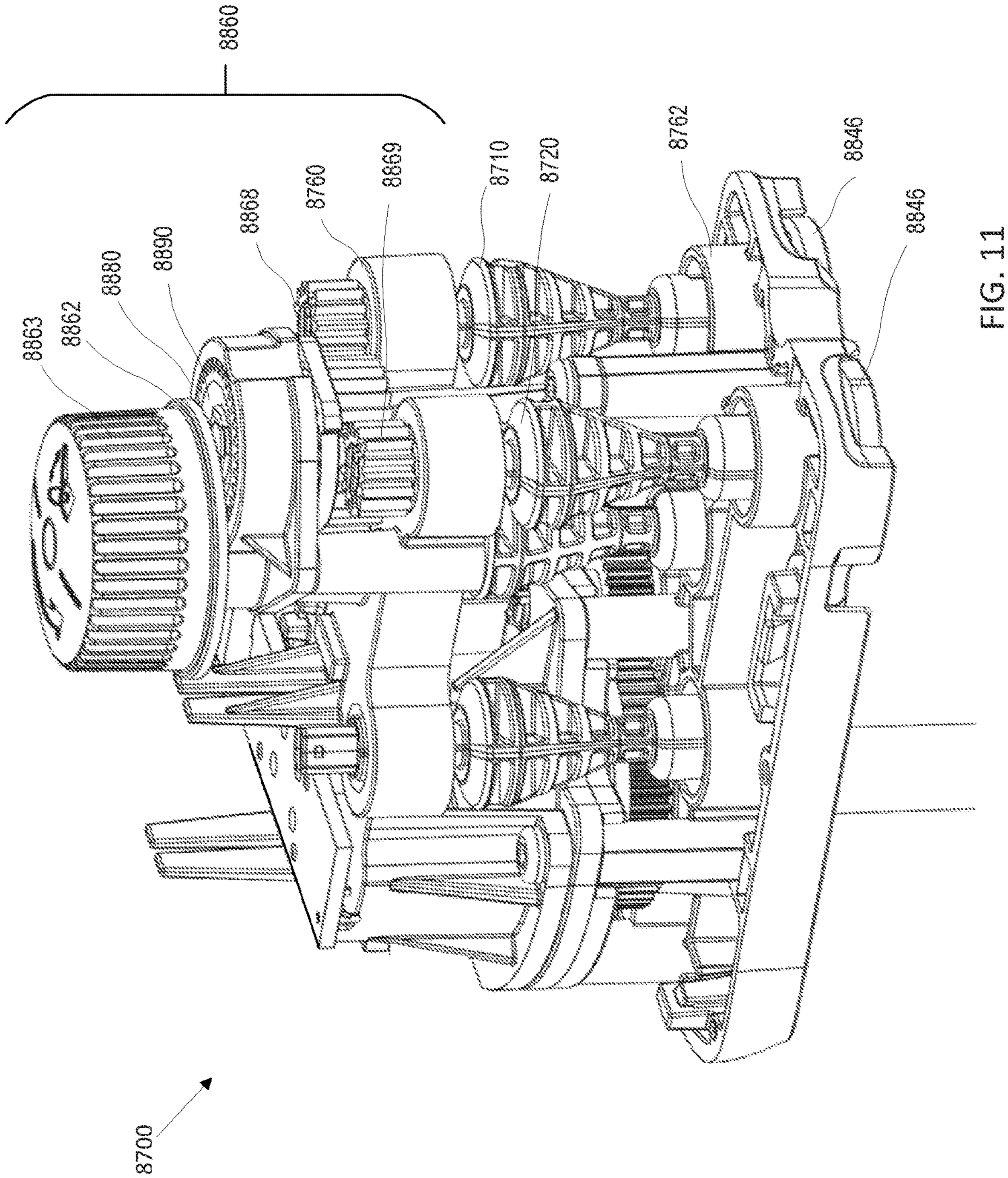
FIG. 11 is a perspective view of a mechanical structure of the medical device of FIG. 10.
Figure 12:
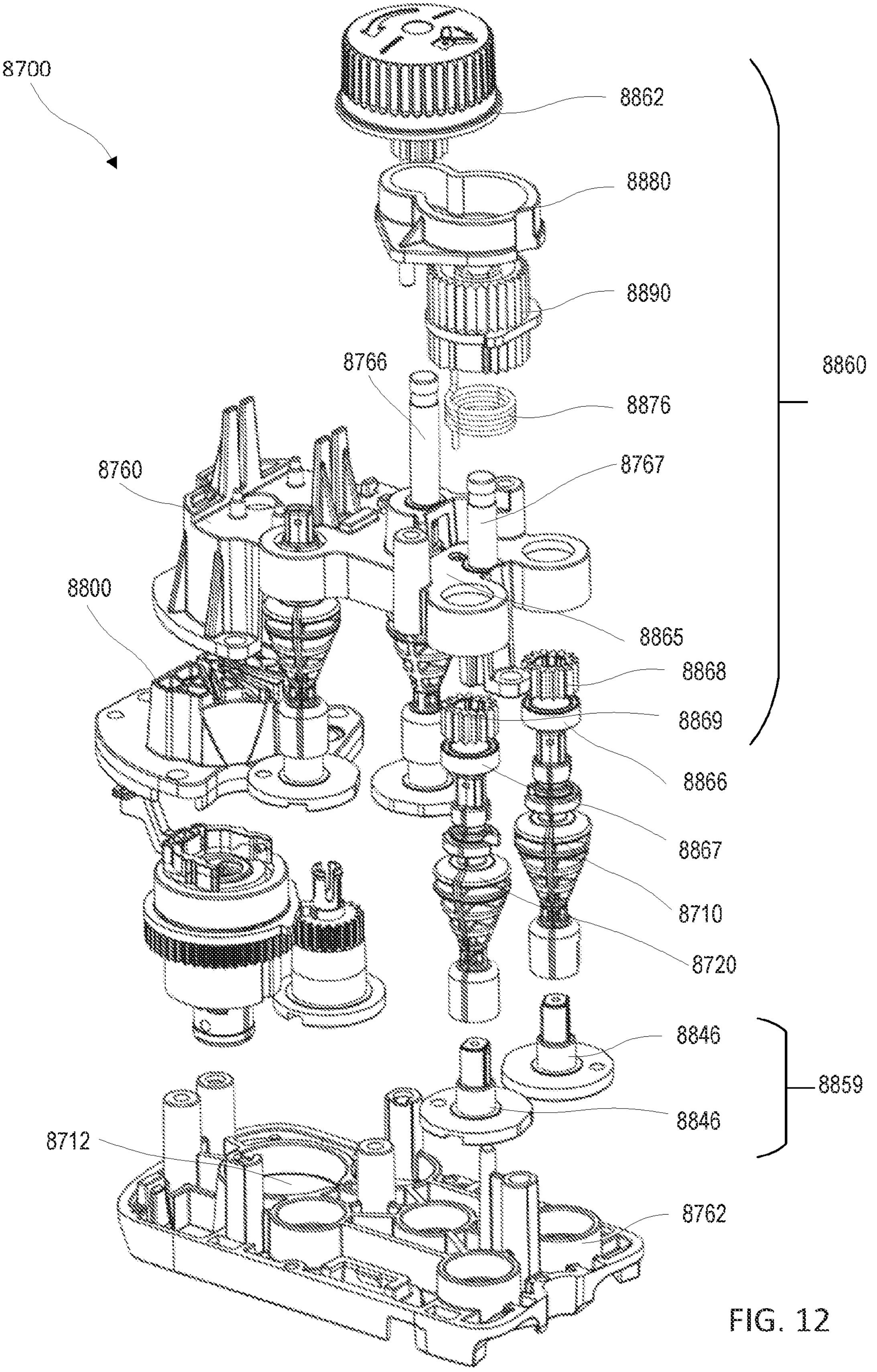
FIG. 12 is an exploded view of a portion of the medical device of FIG. 10.

For actuation of the end effector 8460, the proximal mechanical structure 8700 includes motor drive structure 8859 and a manual drive structure 8860 as shown in FIGS. 11 and 12. Additionally, the mechanical structure 8700, as shown in FIGS. 11-14, includes an upper chassis 8760, a lower chassis 8762, the first capstan 8710, the second capstan 8720, the third capstan 8730, the fourth capstan 8740, and a cable guide 8800. The manual drive structure 8860 includes a manual drive input member 8862, a manual drive coupler 8890, a first capstan gear 8868 (which functions as a first manual drive input), and a second capstan gear 8869 (which functions as a second manual drive input). Additionally, the manual drive structure 8860 can also include a biasing member 8876 and bracket 8880. Both the motor drive structure 8859 and the manual drive structure 8860 are connected to and drive the first capstan 8710 and the second capstan 8720. As discussed in more detail below, the capstans 8710, 8720, 8730, 8740 are connected to and actuate, via the motor drive structure 8859 or the manual drive structure 8860, the first cable 8420 and the second cable 8430).

Figure 14:
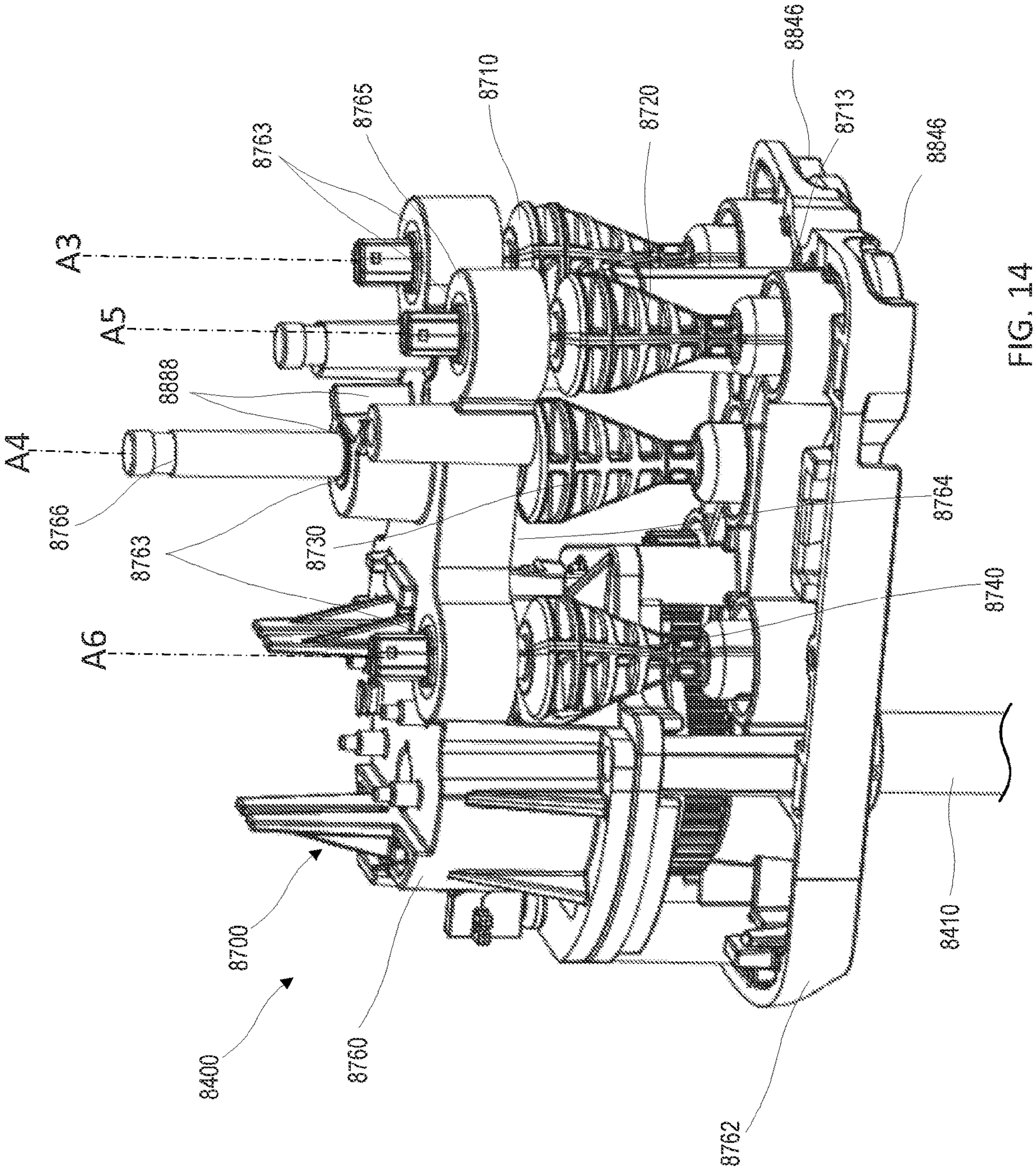
FIG. 14 is a perspective view of a tool drive structure of the medical device of FIG. 10.

In some embodiments, the upper chassis 8760 and the lower chassis 8762 may partially enclose or fully enclose other components of mechanical structure 8700. In some embodiments, a housing cover (not shown) encloses the mechanical structure 8700, including the upper chassis 8760 and the lower chassis 8762. The lower chassis 8762 and the upper chassis 8760 provide structural support for mounting and aligning components in the mechanical structure 8700. For example, the lower chassis 8762 includes a shaft opening 8712 (see FIGS. 10 and 12), within which the proximal end 8411 of the shaft 8410 is mounted. The lower chassis 8762 further includes one or more bearing surfaces or openings 8713, within which the capstans (e.g., the first capstan 8710 and the second capstan 8720) are mounted and rotatably supported. The upper chassis 8760 also includes openings 8763 in a bottom 8764, within which an upper portion of the capstans are mounted as described in more detail below. The openings 8763 of the upper chassis 8760 are axially aligned with the openings 8713 of the lower chassis 8762 to support the capstans. As shown in FIGS. 12 and 14, the upper chassis 8760 includes a first spindle 8766 and a second spindle 8767. The first spindle 8766 extends from the structure that includes the end stops 8888 (described in more detail below) and receives the manual drive input member 8862. Thus, in use, when the user rotates the manual drive input member 8862, the manual drive input gear 8864 rotates about the first spindle 8766. The second spindle 8767 extends from the top surface 8865 and receives the manual drive coupler 8890. Thus, in use when the manual drive input gear 8864 rotates about the first spindle 8766, its engagement with the manual drive coupler 8890 (described below) causes the manual drive coupler 8890 to rotate about the second spindle 8767.

In addition to providing mounting support for the internal components of the mechanical structure 8700, the lower chassis 8762 can include external features (e.g., recesses, clips, etc.) that interface with a docking port of a drive device (not shown). The drive device can be, for example, a handheld system or a computer-assisted teleoperated system that can receive the medical device 8400 and manipulate the medical device 8400 to perform various surgical operations. The drive device can include one or more motors to drive capstans of the mechanical structure 8700. In other embodiments, the drive device can be an assembly that can receive and manipulate the medical device 8400 to perform various operations.

Figure 15B:
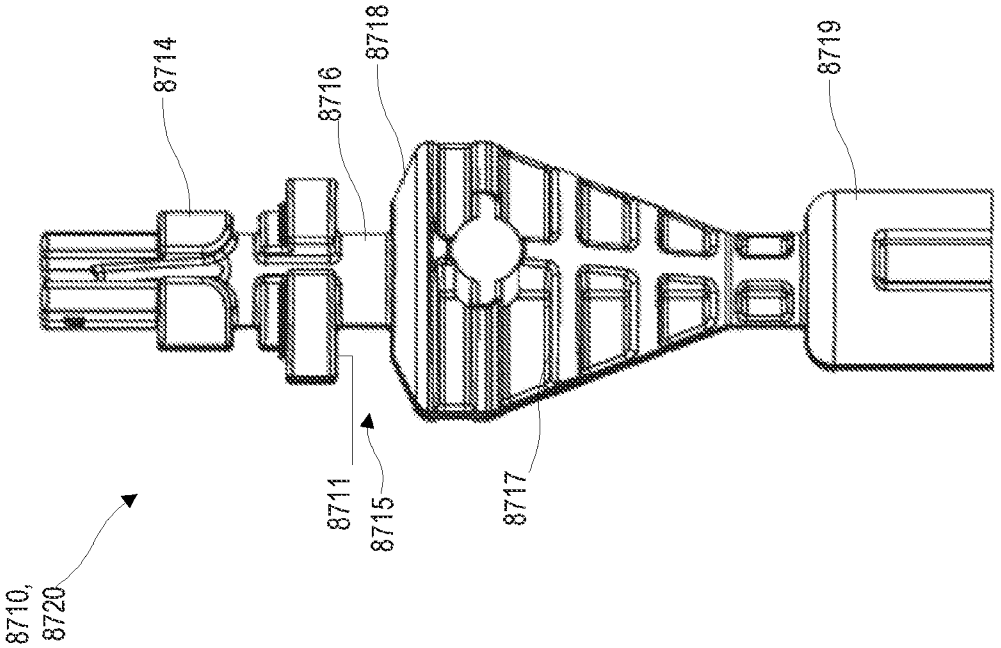
FIGS. 15A and 15B are views of a capstan of the medical device of FIG. 10, with FIG. 15A being a side view in a first state and FIG. 15B being a side view in a second state.
Figure 15A:
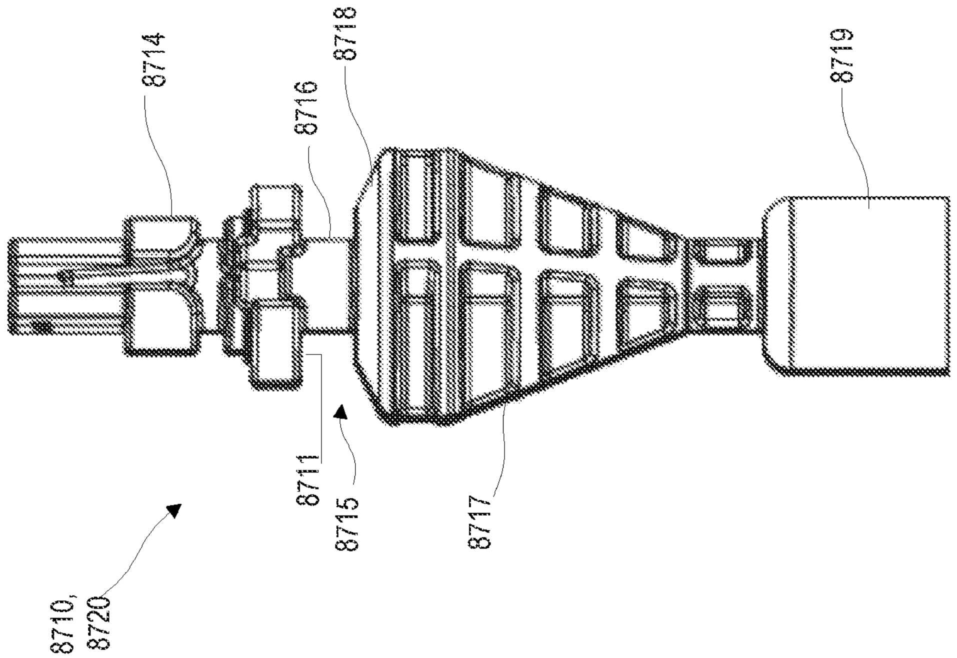

As shown in FIGS. 15A and 15B, the first capstan 8710 includes an upper portion 8714, a lower portion 8717, and a spool 8715 between the upper portion 8714 and the lower portion 8717. The upper portion 8714 functions as an anchor portion to secure the first cable 8420 to the capstan 8710. In some embodiments, the upper portion 8714 can include a specific configuration to allow for a cable to be coupled to the capstan without the use of external mechanisms (e.g., crimp joints, adhesive, knots) to maintain the coupling of the cable to the capstan 8710. Such configuration can include, for example, grooves and recesses within which the cable can be wrapped, as shown and described in U.S. provisional application No. 63/233,904 entitled "SURGICAL INSTRUMENT CABLE CONTROL AND ROUTING STRUCTURES" filed on Aug. 17, 2021, which is incorporated herein by reference in its entirety. In other embodiments, however, the upper portion can include recesses or channels that receive a crimp or know to secure the cable therein. The spool 8715 includes a cable wrap surface 8716 (which functions as a drive surface) and a side wall 8718. The first cable 8420 is coupled to the first capstan 8710 such that a proximal end portion of the first cable 8420 wraps about the cable wrap surface 8716 of the first capstan 8710. While other capstans are shown, they are not discussed in detail herein.

The lower portion 8717 of the first capstan 8710 is supported by the lower chassis 8762, and the upper portion 8714 of the first capstan 8710 is supported within the opening 8763 defined in the bottom 8764 of the upper chassis 8760) (see, e.g., FIG. 14). In some embodiments, the bottom 8764 of the upper chassis 8760 has a continuous planar surface in which the openings 8763 are defined. In some embodiments, the bottom 8764 of the upper chassis has portions with surfaces in which the openings 8763 are defined, such as by the bottom of a support web structure of bracing material in the upper chassis. In some embodiments, a bottom 8711 of the upper portion 8714 (see, e.g., FIGS. 15A and 15B) of the first capstan 8710 is within the opening 8763 such that it is between the bottom 8764 of the upper chassis 8760 and a top surface 8765 of the upper chassis 8760. In other words, the entire upper portion 8714 of the first capstan 8710 is within the opening 8763. In some embodiments, the bottom 8711 of the upper portion 8714 of the first capstan 8710 is positioned flush with the bottom 8764 of the upper chassis 8760. The side wall 8718 of the spool 8715 slopes away from the bottom 8764 of the upper chassis 8760. The second capstan 8720, along with other capstans, can be structured the same as the first capstan 8710 and can be supported by the lower chassis 8762 and the upper chassis 8760 in the same manner, and are therefore not described in detail here.

Figure 20B:
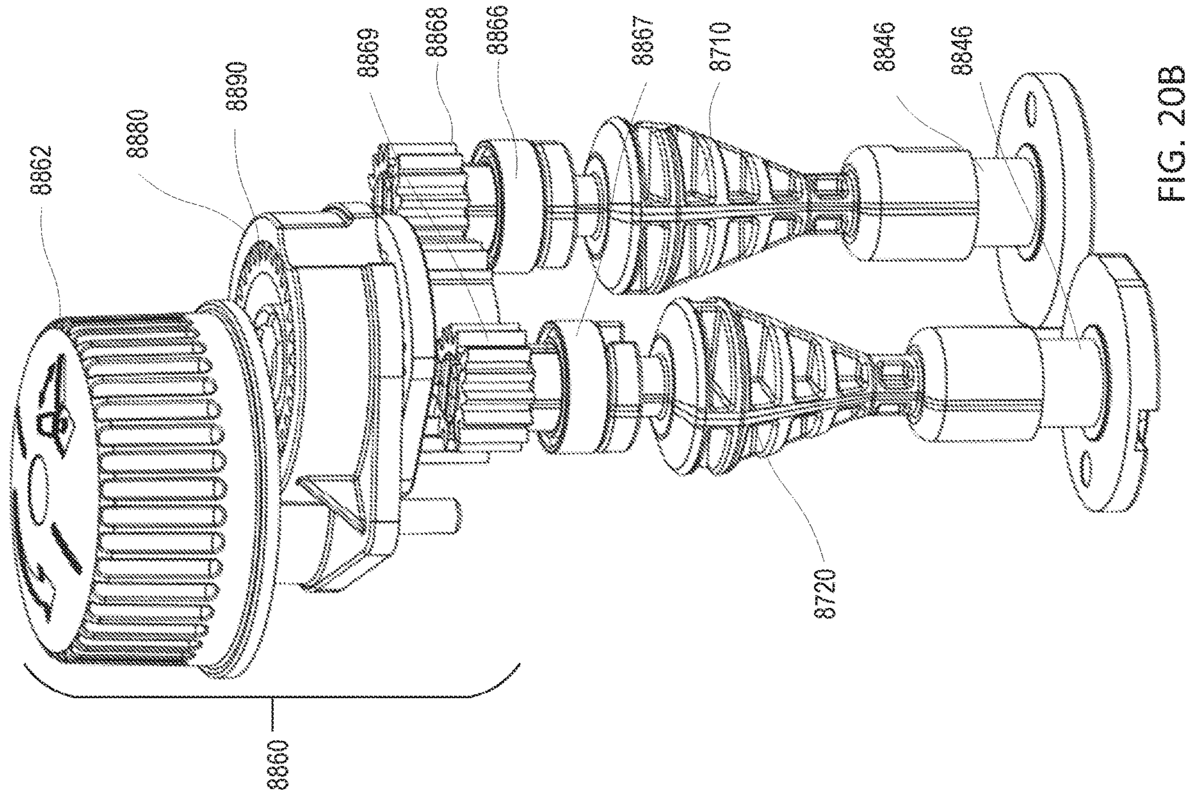
FIGS. 20A and 20B are perspective views of a manual drive structure of the medical device of FIG. 11 with components removed for simplicity, with FIG. 20A in a first state and FIG. 20B in a second state.
Figure 20A:
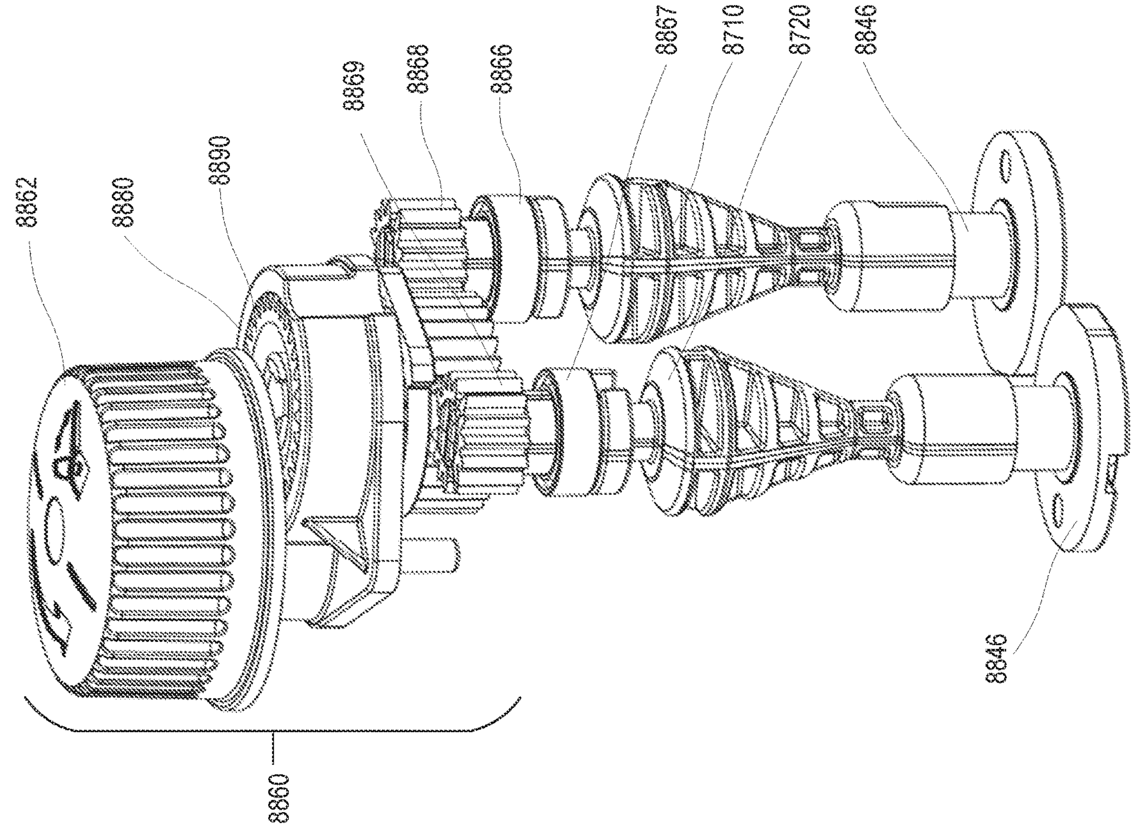
Figure 21A:
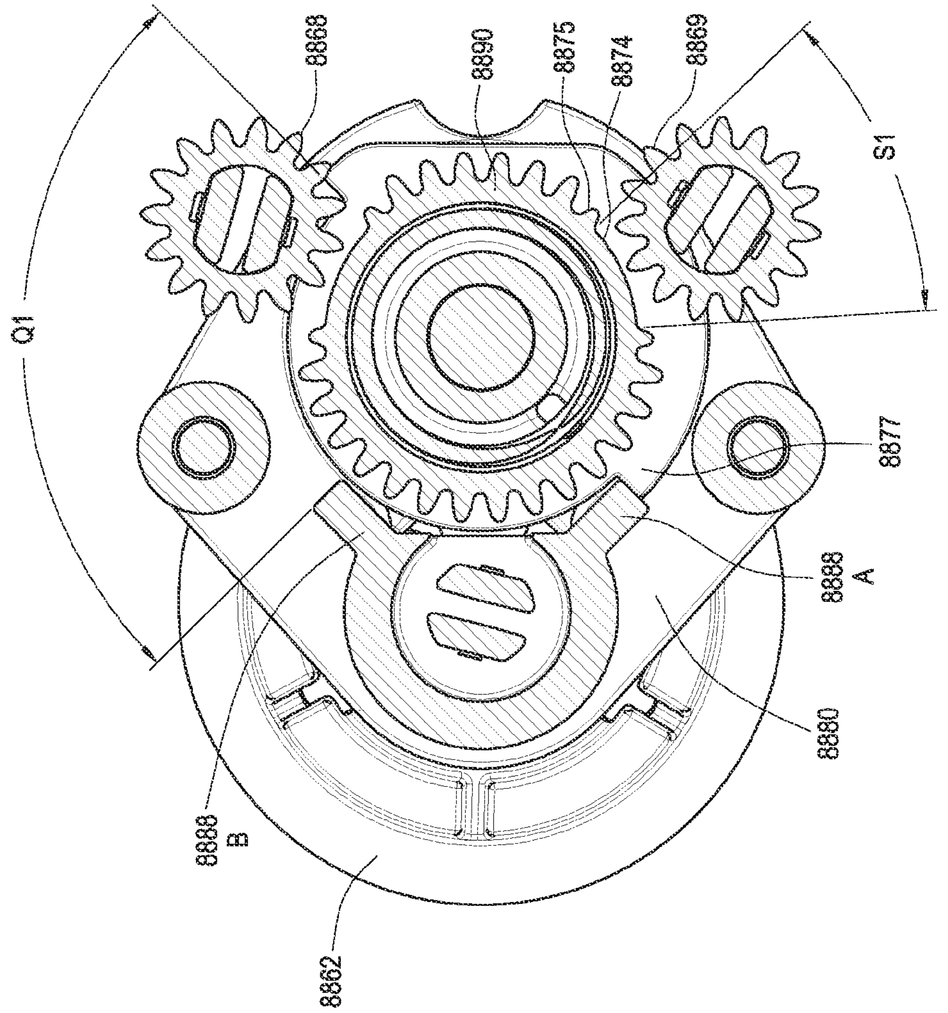
FIGS. 21A and 21B are bottom views of portions of the manual drive structure of the medical device of FIG. 11 with components removed for simplicity, with FIG. 21A in a first state and FIG. 21B in a second state.
Figure 21B:
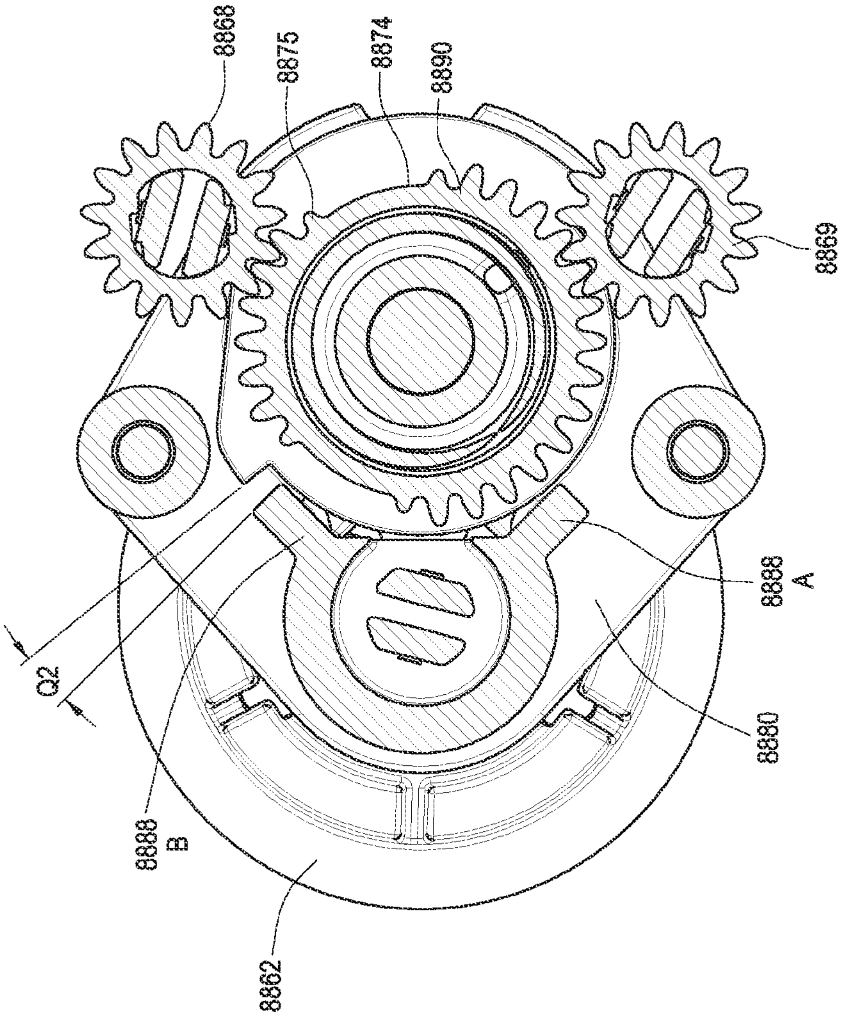

As described above, the upper portion 8714 of each of the capstans 8710, 8720 is rotatably supported within a corresponding opening 8763 (see FIG. 14) of the upper chassis 8760. More specifically, bearings 8866, 8867 are coupled to the upper portion 8714 of the capstans, and the bearings 8866, 8867 are supported within the opening 8763. The bearings 8866, 8867 can be, for example, a rolling-element bearing, such as a ball or needle bearing. As shown in FIGS. 20A and 20B, the upper portion 8714 also provides a protrusion about which the first capstan gear 8868 is coupled. Similarly the upper portion of the second capstan 8720 provides a protrusion about which the second capstan gear 8869 is coupled.

Figure 16B:
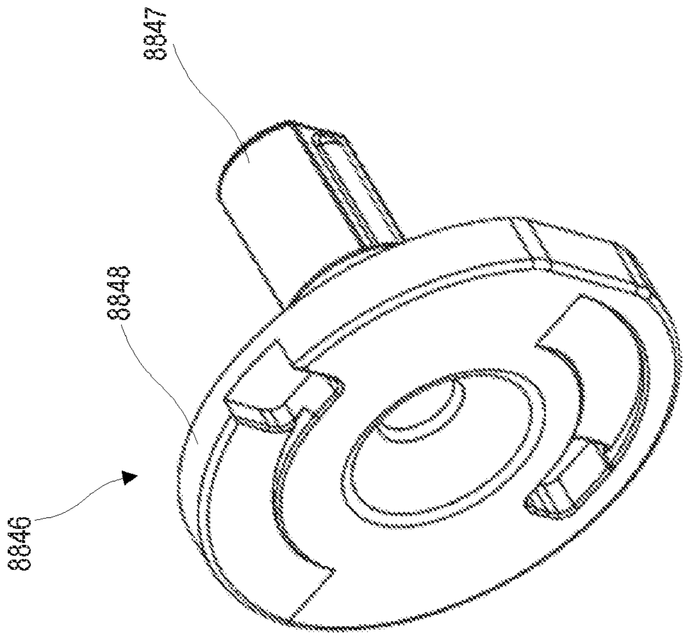
FIGS. 16A and 16B are views of a drive disc of the medical device of FIG. 10, with FIG. 16A being a side view and FIG. 16B being a perspective view.
Figure 16A:
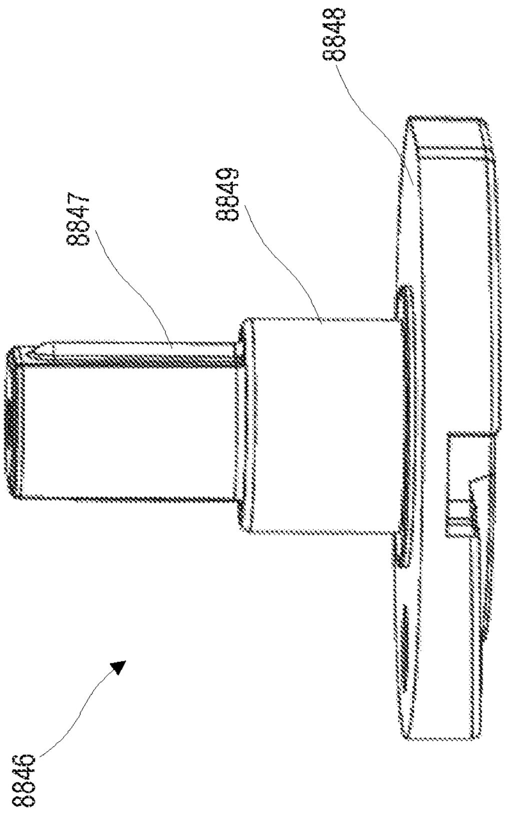

In addition, in this embodiment, the lower portion 8717 of each of the capstans 8710, 8720 is supported by the lower chassis 8762 via bearings. In some embodiments, the drive discs 8846 can include a bearing surface 8849 that interfaces with journal bearings (not shown) within the lower chassis 8762. As shown in FIGS. 16A and 16B, the drive discs 8846 include a neck 8847, a coupling portion 8848, and a bearing surface 8849. The neck 8847 is received within an opening (not shown) in the bottom end portion 8719 of the capstans 8710, 8720. The coupling portion 8848 can be coupled to the lower chassis 8762, for example, within the openings 8713. The end surface of the drive portion 8848 is exposed from under the mechanical structure 8700 and can be mated with a corresponding drive disc in a manipulator. Thus, motors can be operationally coupled to rotate the capstans via the drive discs 8846. The bearing surface 8849 interfaces with a journal bearing pressed within the lower chassis 8762. Any suitable drive disk can be used with the various embodiments disclosed herein. For example, U.S. Pat. No. 10,247, 911 entitled "Instrument Sterile Adapter Drive Features", issued on Apr. 30, 2021, which is hereby incorporated by reference in its entirety, discloses additional systems and features of drive disks that can be used with the embodiments herein.

Each of capstans 8710, 8720, 8730, 8740 can be driven by one or more corresponding motors (not shown) in the drive device (e.g., the manipulator unit 1200) via the motor drive structure 8859 (which includes the drive discs). For example, as shown in FIG. 14, the first capstan 8710 can be driven to rotate about a first capstan axis A3, the second capstan 8720) can be driven to rotate about a second capstan axis A5, the third capstan 8730 can be driven to rotate about a third capstan axis A4, and the fourth capstan 8740 can be driven to rotate about a fourth capstan axis A6.

As shown in FIG. 13, the first proximal portion 8421 of the first cable 8420) is coupled to the first capstan 8710 and extends to a cable guide 8800 within the mechanical structure 8700, where it is rerouted through an interior passageway of the shaft 8410 (not shown in FIG. 13), and extends to the wrist assembly 8500 (not shown in FIG. 13), and to the end effector 8460 (not shown in FIG. 13). A distal portion of the first cable 8420 is coupled to the end effector 8460 (i.e., the first tool member 8462), and then the first cable 8420 extends proximally back through the interior passageway of the shaft 8410, proximally back through the cable guide 8800 and to the third capstan 8730, where a second proximal portion 8423 of the first cable 8420 is coupled to the third capstan 8730. Similarly, the second cable 8430) is also routed between the mechanical structure 8700 and the end effector 8460. More specifically, the proximal end 8431 of the second cable 8430 is coupled to the third capstan 8730 and extends to the cable guide 8800, where it is rerouted through the interior passageway of the shaft 8410 and extends to the wrist assembly 8500 and to the end effector 8460. A distal portion of the second cable 8430 is coupled to the end effector 8460 (i.e., the second tool member 8482), and then the second cable 8430 extends back through the interior passageway of the shaft 8410, through the cable guide 8800, and to the fourth capstan 8740, where the second proximal portion 8433 of the second cable 8430 is coupled to the fourth capstan 8740. Thus, the two proximal end portions of the cable 8420 are coupled to and actuated by two separate capstans (capstans 8710) and 8730) of the mechanical structure 8700. Likewise, the two proximal end portions of the second cable 8430 are coupled to and actuated by two separate capstans (capstans 8720) and 8740).

More specifically, the two ends of the first cable 8420 that are associated with opposing directions of a single degree of freedom are connected to two independent drive capstans 8710 and 8730, and the two ends of the second cable 8430 that are associated with opposing directions of a single degree of freedom are connected to two independent drive capstans 8720 and 8740. This arrangement, which is generally referred to as an antagonist drive system (a different example of which is described above with reference to FIG. 5), allows for independent control of the movement of (e.g., pulling in or paying out) each of the ends of the cables. The mechanical structure 8700 produces movement of the first cable 8420 and the second cable 8430, which operates to produce the desired articulation movements (pitch, yaw, cutting or gripping) at the end effector 8460. Accordingly, as described herein, the mechanical structure 8700 includes components and controls to move a first portion 8421 of the first cable 8420 via the first capstan 8710 in a first direction (e.g., a proximal direction) and to move a second portion 8423 of the first cable 8420 via the third capstan 8730 in a second opposite direction (e.g., a distal direction). The mechanical structure 8700 can also move both the first portion 8421 of the first cable 8420 and the second portion 8423 of the first cable 8420 in the same direction. The mechanical structure 8700 also includes components and controls to move a first portion 8431 of the second cable 8430 via the second capstan 8720 in a first direction (e.g., a proximal direction) and to move a second portion 8433 of the second cable via the fourth capstan 8740) in a second opposite direction (e.g., a distal direction). The mechanical structure 8700 can also move both the first portion of the second cable and the second portion of the second cable in the same direction. In this manner, the mechanical structure 8700 can maintain the desired tension within the cables to produce the desired movements at the end effector 8460.

As shown in FIG. 13, the cable guide 8800 includes an upper portion 8840 and a lower portion 8842. The lower portion 8842 is mounted to a component within the mechanical structure 8700, such as the lower chassis 8762. The upper portion 8840 includes multiple guide grooves 8831 on a top guide surface 8841. The guide grooves 8831 extend along the top guide surface 8841 to openings 8832 that are defined in the top surface 8841. As shown in FIG. 13, the cables 8420, 8430 are routed along the top surface 8841 within the guide grooves 8831 and through the openings 8832 to be routed to the interior passageway of the shaft 8410.

Figure 17B:
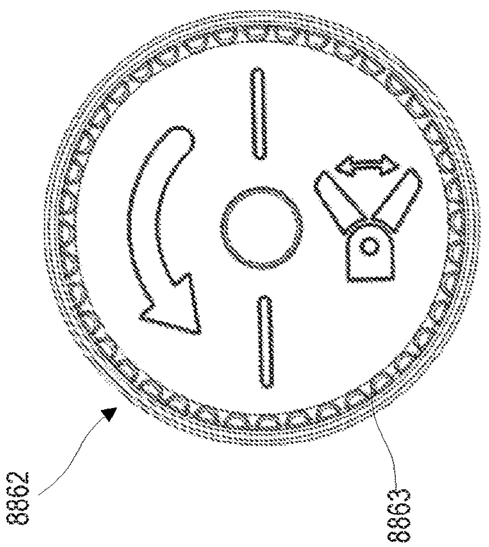
FIGS. 17A-C are views of a manual drive input member of the manual drive structure of FIG. 10, with FIG. 17A being a side view, FIG. 17B being a top view and FIG. 17C being a perspective view.
Figure 17C:
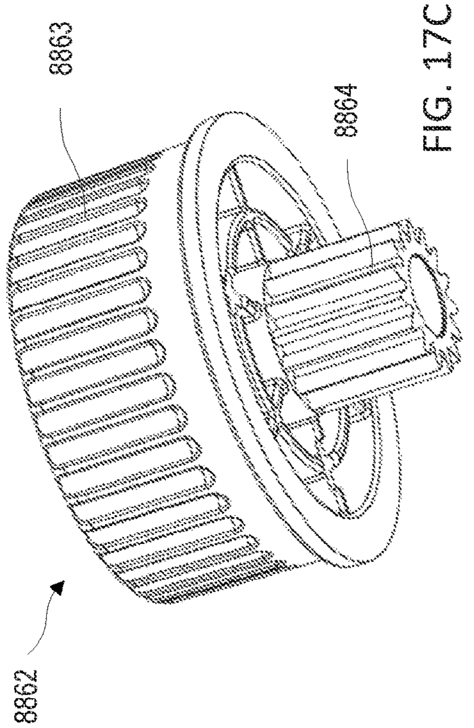
Figure 17A:
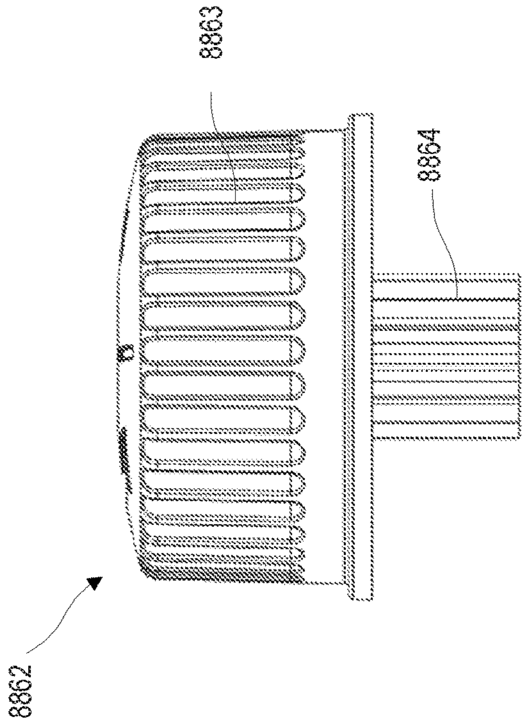

The manual drive structure 8860 includes a manual drive input member 8862, a manual drive coupler 8890, the first capstan gear 8868, the second capstan gear 8869, a biasing member 8876 and a support bracket 8880. As shown in FIGS. 17A-C, the manual drive input member 8862 includes a manual interface 8863 and a manual drive input gear 8864. The manual interface 8863 includes a surface that is exposed to the exterior of the medical device 8400. The user can engage the manual interface 8863 and manipulate the manual drive structure 8860, thereby manipulating the end effector 8460. The exposed portion of the manual interface 8863 can include knurls, ridges, or other traction features on the surfaces suitable for the user to apply a torque to the manual drive input member 8862 via the manual interface 8863. As shown in FIGS. 17A-C, the manual interface 8863 includes a rotatable knob that receives the user's input force and allows the manual drive structure 8860 to convert the user's input force to a torque on the first capstan 8710 and the second capstan 8720 and thereby manipulate the end effector 8460 via cables 8420 and 8430. Specifically, as described herein, the input force can be converted by the manual drive structure to open the jaws of the end effector in the event of a fault, loss of power, or other instance where manual control is desired. As shown in FIG. 17B, the manual interface 8863 also includes indicia (i.e., the arrow and the depiction of jaws opening) to guide the user in the operation of the manual drive structure 8860. The manual drive input gear 8864 is connected to and receives any torque applied to the manual interface 8863. The manual drive input gear 8864 includes gear teeth suitable to engage with an adjacent gear (specifically, the manual-drive-side coupling gear 8872).

Figure 18B:
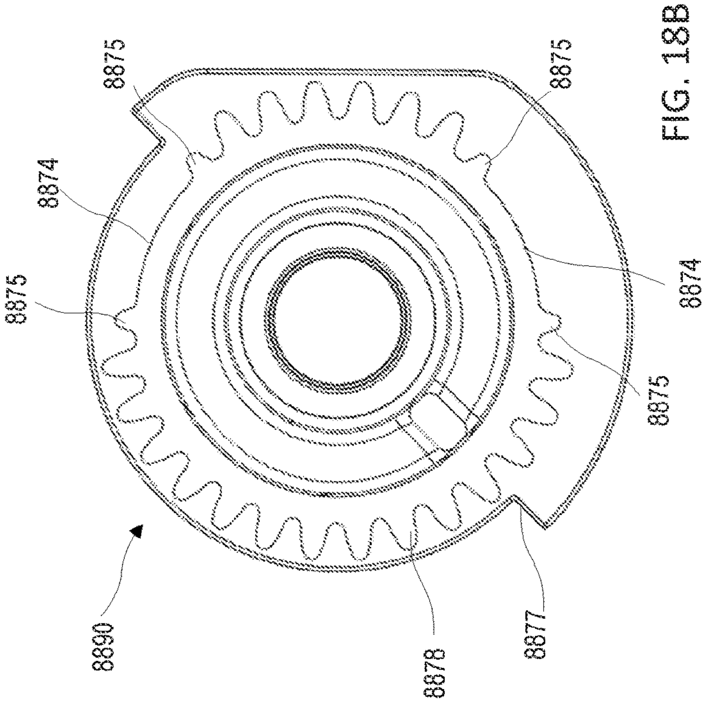
FIGS. 18A-C are views of a manual drive coupling member of the manual drive structure of FIG. 10, with FIG. 18A being a side view, FIG. 18B being a top view in a first state and FIG. 18C being a top view in a second state.
Figure 18A:
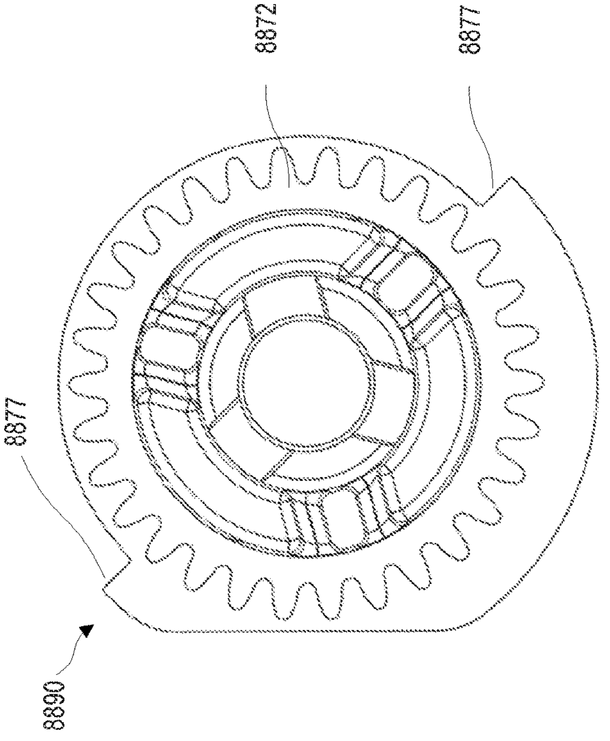
Figure 18C:
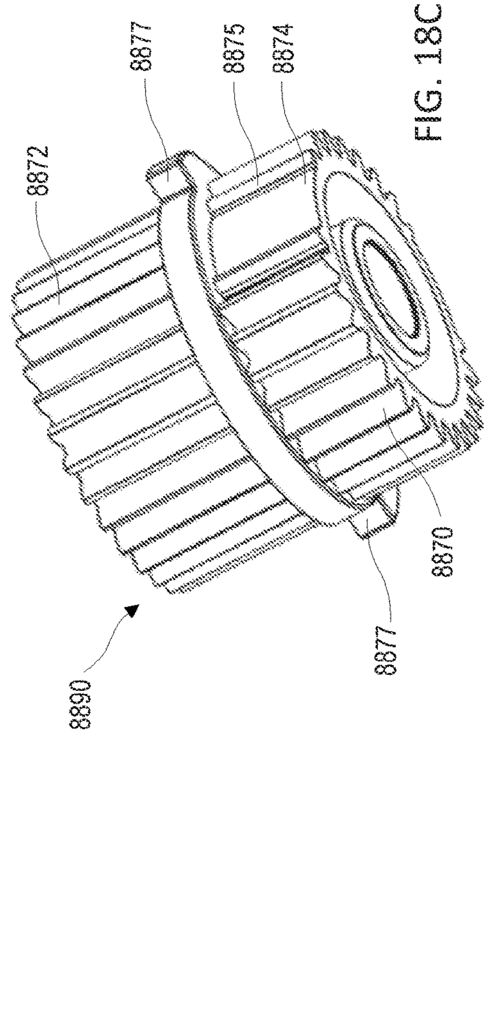

The manual drive coupling member 8890 allows for selective engageability between the manual drive input member 8862 and the capstans 8710, 8720. As shown in FIGS. 18A-C, the manual drive coupling member 8890 includes a tool-drive-side coupling gear 8870, a manual-drive-side coupling gear 8872, and a central portion therebetween that includes two end stops 8877. The tool-drive-side coupling gear 8870 is a gear having teeth suitable to engage the first capstan gear 8868 and the second capstan gear 8869. The tool-drive-side coupling gear 8870 includes two non-engagement portions 8874, two engagement portions 8878, and a gear tooth gradient portion 8875. The non-engagement portions 8874 are portions of the tool-drive-side coupling gear 8870 without engagement teeth. Thus, when the non-engagement portions 8874 of the tool-drive-side coupling gear 8870 is positioned adjacent to (i.e., aligned with) the teeth of the first capstan gear 8868 or the second capstan gear 8869, no torque is transferred between the gears. The engagement portions 8878 are portions of the tool-drive-side coupling gear 8870 with engagement teeth. Thus, when the engagement portions 8878 of the tool-drive-side coupling gear 8870 are positioned adjacent to (i.e., meshed with) the teeth of the first capstan gear 8868 or the second capstan gear 8869, torque is transferred between the gears. The gear tooth gradient portions 8875 is the portion of the gear between the non-engagement portion 8874 and the engagement portion 8878. In this section of the gear, the teeth are smaller than the teeth in the engagement portion 8878 and configured to form a lead-in, allowing for gear engagement as the tool-drive-side coupling gear 8870) transitions from the non-engagement portion 8874 to the engagement portion 8878.

The manual-drive-side coupling gear 8872 is a gear positioned along the same axis as the tool-drive-side coupling gear 8870. The manual-drive-side coupling gear 8872 includes engagement members (e.g., teeth) suitable to engage the manual drive input gear 8864. While FIGS. 18A-C show the tool-drive-side coupling gear 8870 as having the non-engagement portions 8874, in some embodiments the manual-drive-side coupling gear 8872 could alternatively include one or more non-engagement portions 8874. The end stops 8877 are configured to limit the range of rotation of the manual drive coupling member 8890. As shown in FIGS. 18A-C, the manual drive coupling member 8890 includes opposing end stops 8877. Each end stop 8877 can include a contact surface suitable to engage a separate structure (e.g., the end stop 8888 of the upper chassis 8760), thereby limiting the range of rotation of the manual drive coupling member 8890.

Figure 19B:
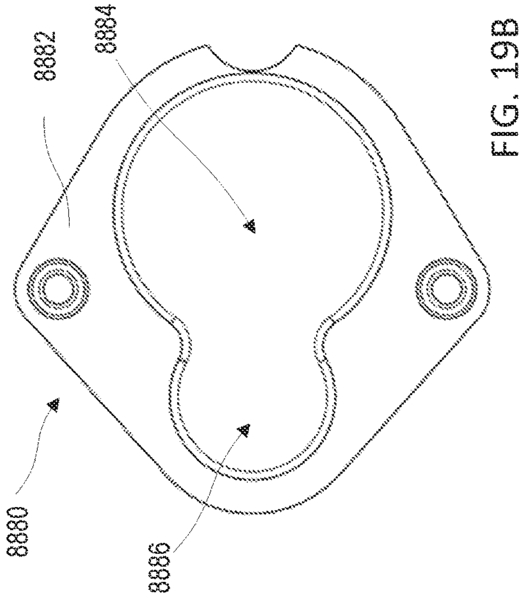
FIGS. 19A-C are views of a support bracket of the manual drive structure of FIGS. 15A-15B, with FIG. 19A being a top view, FIG. 19B being a bottom view and FIG. 19C being a perspective view.
Figure 19C:
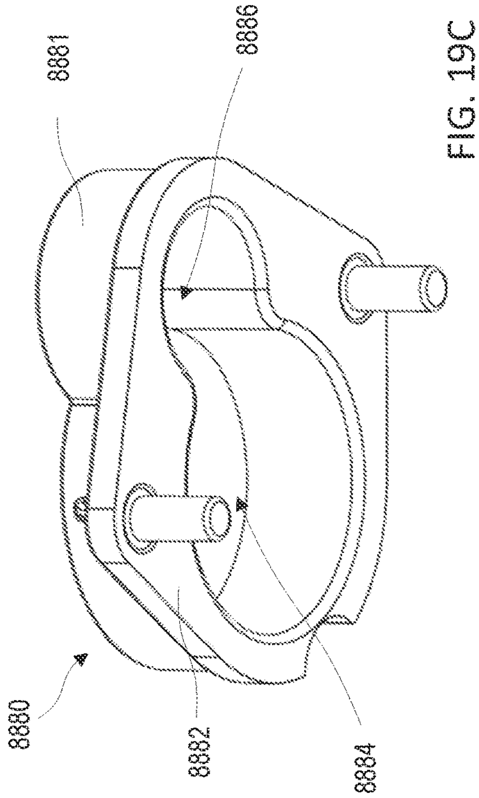
Figure 19A:
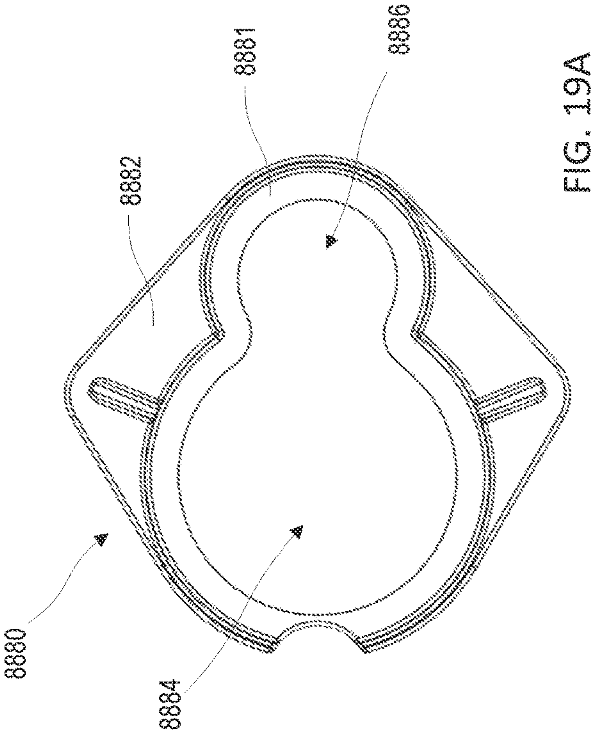

As shown in FIGS. 19A-C, the support bracket 8880 of the manual drive structure 8860 includes a wall 8881 and a mounting flange 8882. The wall 8881 defines a first aperture 8884 and a second aperture 8886. The support bracket is configured to locate or shield the engagement between the manual-drive-side coupling gear 8872 and the manual drive input gear member 8864. The first aperture 8884 is sized to receive the manual-drive-side coupling gear 8872. The second aperture 8886 is sized to receive the manual drive input gear member 8864. The two apertures merge together where the manual-drive-side coupling gear 8872 and the manual drive input gear member 8864 engage with one another. The mounting flange 8882 is configured to mount to the surface of upper chassis 8760. The upper chassis includes end stops 8888. The end stops 8888 protrude from the upper surface 8765 of the upper chassis 8760 (see e.g., FIG. 14). The end stops 8888 are located such that end stops 8877 contact the end stops 8888 when the manual drive coupling member 8890 is rotated sufficiently far in each direction.

The manual drive coupling member 8890 is connected to the manual drive input member 8862 via engagement between the manual-drive-side coupling gear 8872 and the manual drive input gear 8864. As shown in FIGS. 20A-B, this engagement occurs within the support bracket 8880. Rotation of the manual interface member 8863 (about the first spindle 8766) causes rotation of the manual-drive-side coupling gear 8872 (about the second spindle 8767). The manual drive coupling member 8890 is selectably connected to the first capstan gear 8868 and the second capstan gear 8869. In a first state, the non-engagement portions 8874 of the manual drive coupling member 8890 are rotationally aligned with the teeth of the first capstan gear 8868 and the second capstan gear 8869 (see e.g., FIGS. 20A and 21A). In the first state, the manual drive coupling member 8890 is disengaged from the capstan gears. Thus, rotation of the first capstan gear 8868 or the second capstan gear 8869 does not result in any movement of the manual drive coupling member 8890 (or the manual drive input member 8862). In a second state, the engagement portion 8878 (e.g., teeth) of the manual drive coupling member 8890 are meshed with the teeth of the first capstan gear 8868 and the second capstan gear 8869. In this position, the teeth of the manual drive coupling member 8890 and the teeth of the capstan gears engage with one another, transferring torque therebetween (see e.g., FIGS. 20B and 21B). The manual drive coupling member 8890 transmits the input force from the manual drive input member 8862 to both the first capstan 8710 and the second capstan 8720. Specifically, the first capstan gear 8868 is coupled to the first capstan 8710 and the second capstan gear 8869 is coupled to the second capstan 8720, causing torque from the manual drive structure 8860 to be directed into the first capstan 8710 and the second capstan 8720. This allows the capstans to direct the force via the cables 8420 and 8430 to the end effector 8460 to open the jaws, as discussed in more detail above.

As shown in FIGS. 20A-21B, the different states in which the manual drive structure 8860 operates is based on the rotation of the manual drive coupling member 8890. FIG. 21A shows the total angular range of rotation of the manual drive coupling member 8890 as Q1. This range is the range from end stop 8888A to end stop 8888B. In some embodiments, this range can include rotation from 15 degrees to 350 degrees. In some embodiments, this range can include rotation from 45 degrees to 270 degrees. In some embodiments, this range can include rotation from 60 degrees to 120 degrees. In some embodiments, this range can be about 90 degrees (see e.g., FIG. 21A). The first state can be a sub-range within the total range. As shown, the manual drive structure operates in the first state in any rotational range where the first capstan gear 8868 and the second capstan gear 8869 are located adjacent (i.e., rotationally aligned with) the non-engagement portions 8874 of the manual drive coupling member 8890. In some embodiments, this non-engagement range can include rotation from 5 degrees to 60 degrees. In some embodiments, this non-engagement range can include rotation from 15 degrees to 45 degrees. In some embodiments, this range can be about 30 degrees. Thus, within the non-engagement range (the first state shown in FIGS. 20A and 21A), rotation of the manual drive coupling member 8890 does not cause rotation of the capstans. Likewise, rotation of the capstans does not cause rotation of the manual drive input 8862. Outside of the non-engagement range (the second state shown in FIGS. 20B and 21B), the manual drive structure 8860 operates in the second state in which rotation of the manual drive coupling member 8890 causes rotation of the capstans. Likewise, rotation of the capstans causes rotation of the manual drive input 8862.

The manual drive structure 8860 also includes a biasing member 8876 that is configured to bias the manual drive coupling member 8890 back to the first state. As shown in FIG. 12, the biasing member 8876 is a spring positioned between the manual drive coupling member 8890 and the upper chassis 8760. The spring places a torque on the manual drive coupling member 8890 to urge rotation of the manual drive member 8890 back towards the first state, with the end stop 8877 positioned against the end stop 8888.

Because the manual drive coupling member 8890 is disengaged from the first capstan gear 8868 and the second capstan gear 8869 in the first state, the manual drive coupling member 8890 limits interference (e.g., back drive) from the first capstan 8710 and the second capstan 8720 to the manual drive input member 8862. This also allows the first capstan 8710 and the second capstan 8720 to operate independently of one another (e.g., they can rotate independently, sometimes in the same direction, sometimes in opposite directions of one another, and sometimes one can be stationary while the other rotates).

As discussed above, articulation of the end effector relies on cable 8420 extending between capstans 8710 and 8730. Each capstan can be rotated to place the cable 8420 in tension and cause the cable 8420 to move. The non-driving capstan is also under load to keep the cable in tension. Because in this embodiment the manual drive structure 8860 drives the capstans 8710 and 8720, the cables 8420 and 8430, respectively, can only be placed in tension in one direction. When the biasing member causes the manual drive structure 8860 to return to the first state, capstans 8710 and 8720 may rotate, but they would rotate in the opposite direction of tension on the cables 8420 and 8430, potentially causing slack to form in the cables. It is appreciated that in other embodiments, the cables can extend between two capstans that are both driven by the manual drive structure 8860 such as the examples discussed above in FIGS. 5-9.

Selective engageability of the manual control of the surgical device 8400 allows for simplicity in operation of the device while providing redundancy of tool opening operation. By providing the manual interface 8863 and selective engageability as described above, the manual drive structure can be controlled and operated while the instrument is mounted on an associated teleoperated manipulator without the need for using a separate tool, instead being accessible and engaged by the hands of the user. Having the manual interface engage when desired removes undesirable distractions due to movement of the exterior features of the medical device 8400, thereby improving the usability of the medical device 8400 in a clinical setting.

In another embodiment, as shown in FIGS. 22-25, the manual drive structure 9860 includes a structure that slides (i.e., moves linearly) between a first state and a second state in contrast to FIGS. 10-21B, which shows a structure that rotates between a first state and a second state. FIGS. 22-25 illustrate a portion of a proximal mechanical structure 9700. Other portions of the medical device are omitted for clarity, but it is understood that the mechanical structure 9700 can be incorporated with any of the medical devices described herein. As such, it is understood that the mechanical structure 9700 can be coupled to and used with any end effectors (e.g., the end effector 8460), shafts (e.g., the shaft 8410), or any other components from the various embodiments discussed and detailed herein.

The proximal mechanical structure 9700 includes a chassis 9760, a first capstan 9710, a second capstan 9720, and a manual drive structure 9860. The mechanical structure 9700 includes other components and structure not shown or identified in FIG. 22 but which are similar to components and structure described with reference to the proximal mechanical structure 8700. For example, the proximal mechanical structure 9700 includes a lower chassis similar to the lower chassis 8762 described above.

The manual drive structure 9860 includes a manual drive input member 9862, a manual drive coupler 9890, a biasing mechanism 9876, a guide 9894, and one or more capstan manual drive inputs 9868, 9869. As shown in FIGS. 22-25, the manual drive input member 9862 includes a manual interface 9863 and a manual drive engagement member 9864. The manual interface 9863 includes a surface that is exposed to the exterior of the medical device. The user can engage the manual interface 9863 and manipulate the manual drive structure 9860, thereby manipulating the end effector. The exposed portion of the manual interface 9863 can include knurls, ridges, or other traction features on the surfaces suitable for the user to apply a torque to the manual drive input member 9862 via the manual interface 9863. The manual interface is defined by a rotatable knob that receives the user's input force and allows the manual drive structure 9860 to convert the user's input force to a torque on the capstans 9710, 9720 and thereby manipulate the end effector via cables (e.g., similar to the cables 8420 and 8430 described above). The manual drive engagement member 9864 is connected to and receives the torque applied to the manual interface 9863. The manual drive engagement member 9864 can include a ramped protrusion extending from the manual interface 9863 knob such that it is suitable to engage with the manual drive coupler 9890.

Figure 23:
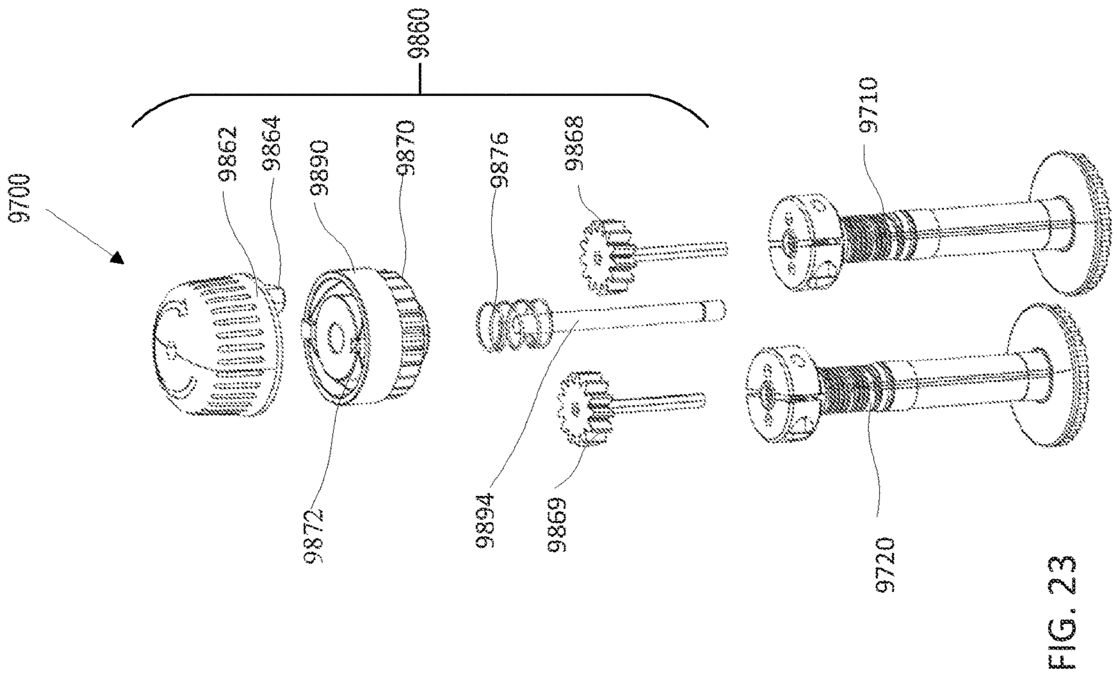
FIG. 23 an exploded view of a portion of the medical device of FIG. 22.

The manual drive coupling member 9890 allows for selective engageability between the manual drive input member 9862 and the capstans 9710, 9720. The manual drive coupling member 9890 includes a tool-drive-side coupling gear 9870 and a manual-drive-side coupling member 9872. The tool-drive-side coupling gear 9870 is a gear having teeth suitable of engaging an adjacent gear (i.e. the first capstan gear 9868 and the second capstan gear 9869). The manual-drive-side coupling member 9872 includes one or more protrusions configured to engage with the manual drive engagement member 9864. As shown in FIG. 23, the manual-drive-side coupling member 9872 can include a ramped receptacle configured to engage with the ramped protrusion of the manual drive engagement member 9864.

Figure 22:
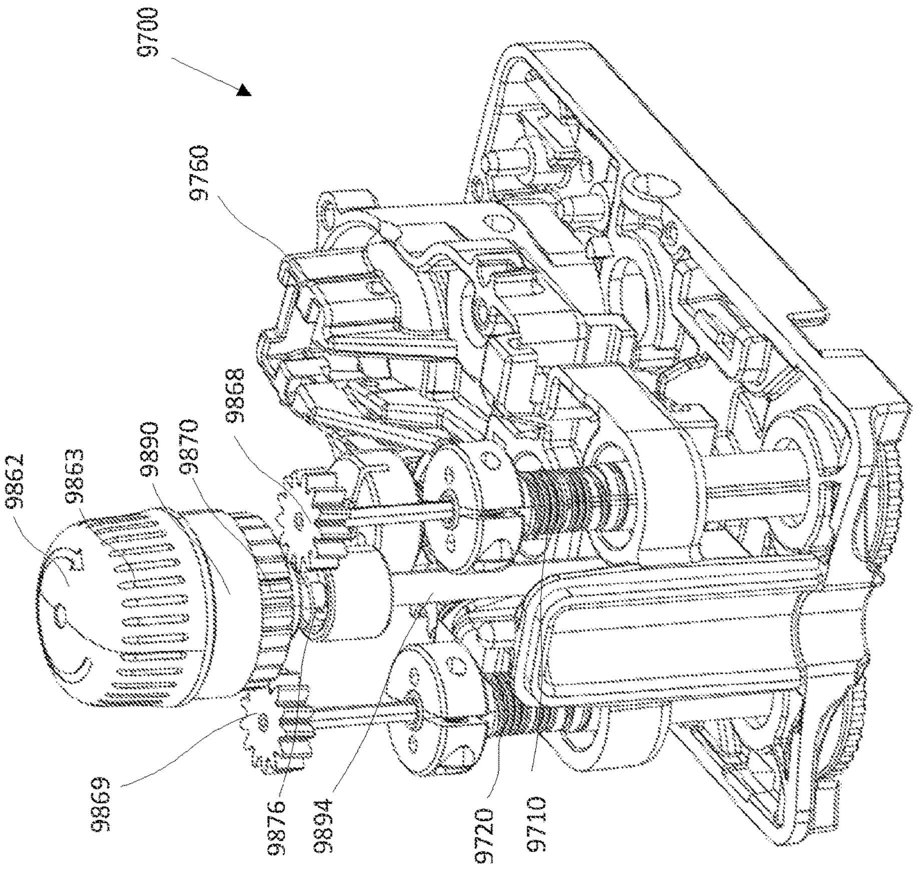
FIG. 22 is a perspective view of a portion of a medical device for manual tool adjustment according to an embodiment.

The manual drive coupling member 9890 is connected to the manual drive input member 9862 via engagement between the manual-drive-side coupling member 9872 and the manual drive input member 9864. As shown in FIGS. 22-23, rotation of the manual interface member 9863 causes rotation of the manual-drive-side coupling member 9872. The guide 9894 defines an axis of rotation and also allows for translation of the manual drive coupling member 9890 and the manual drive input member 9862 along the axis. Similarly stated, the guide 9894 provides a surface along which the manual drive coupling member 9890 can translate, and about which the manual drive coupling member 98900 can rotate. As shown, the axis is coaxial with the axis about which the knob defined by manual interface 9863 rotates.

The manual drive coupling member 9890 is selectably connected to the capstan manual drive inputs 9868, 9869. In a first state, the manual drive coupling member 9890 is biased away from the first capstan gear 9868 and the second capstan gear 9869 by the biasing member 9876 (see e.g., FIG. 24). In the first state, the manual drive coupling member 9890 is disengaged from the capstan gears. Thus, rotation of the first capstan gear 9868 or the second capstan gear 9869 does not result in any movement of the manual drive coupling member 9890 (or the manual drive input member 9862). In a second state, the manual drive coupling member 9890 is positioned adjacent to the first capstan gear 9868 and the second capstan gear 9869 such that the tool-drive-side coupling gear 9870 engages with each of the capstan gears 9868, 9869. In this position, the teeth of the tool-drive-side coupling gear 9870 and the teeth of the first capstan gear 9868 and the second capstan gear 9869 engage with one another, transferring torque therebetween (see e.g., FIG. 25). The first capstan gear 9868 is coupled to the first capstan 9710 and the second capstan gear 9869 is coupled to the second capstan 9720, causing torque from the manual drive structure 9860 to be directed into the capstans 9710 and 9720. Thus, the manual drive coupling member 9890 transmits the user's force from the manual drive input member 9862 to both the capstan 9710 and the capstan 9720. This allows the capstans to direct the force via the cables to the end effector.

Figure 25:
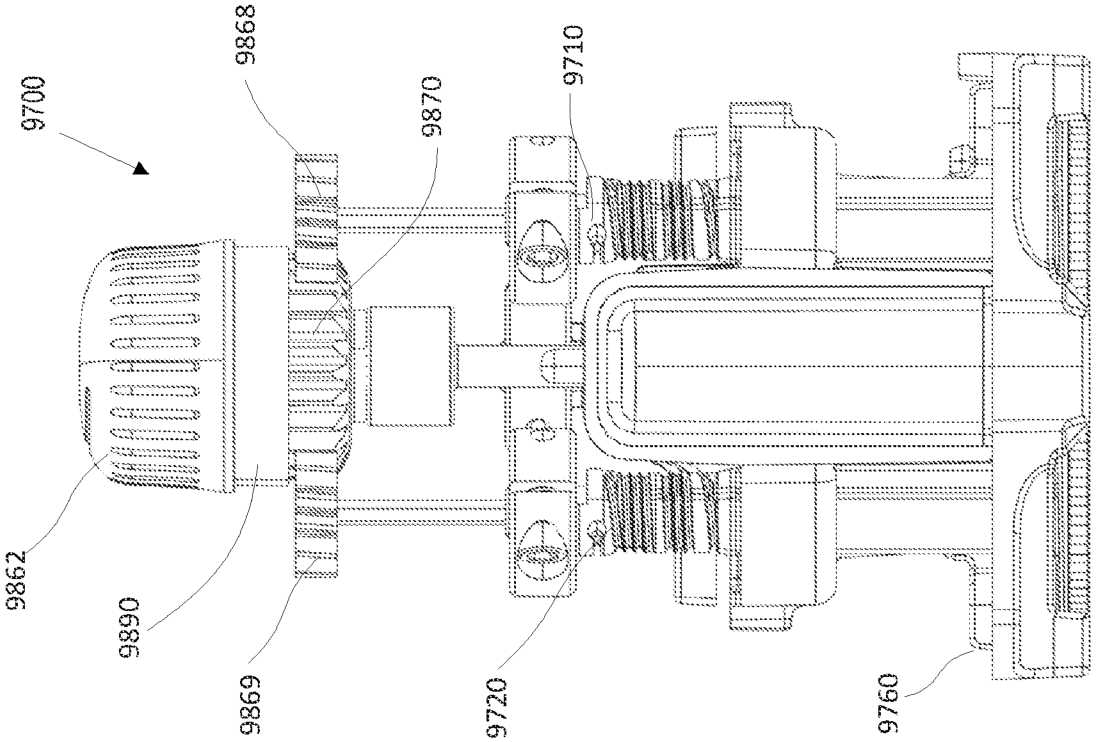
FIGS. 24-25 are back views of the medical device of FIG. 22, with FIG. 24 in a first state and FIG. 25 in a second state.
Figure 24:
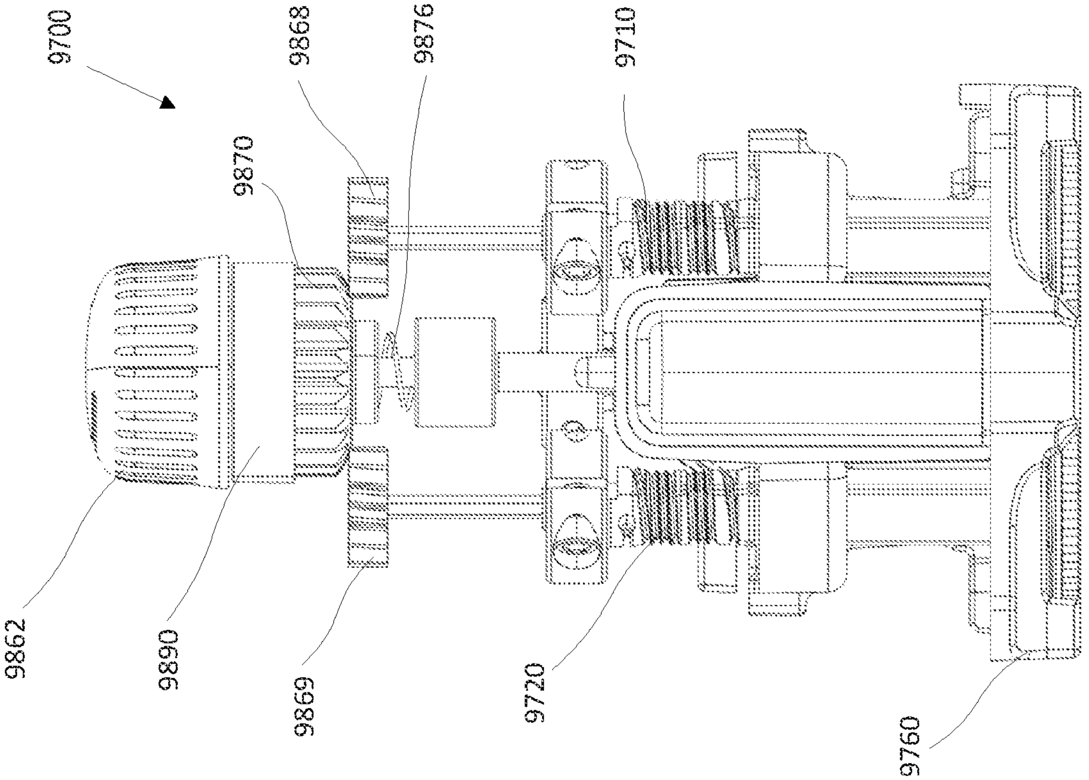
Figure 26:
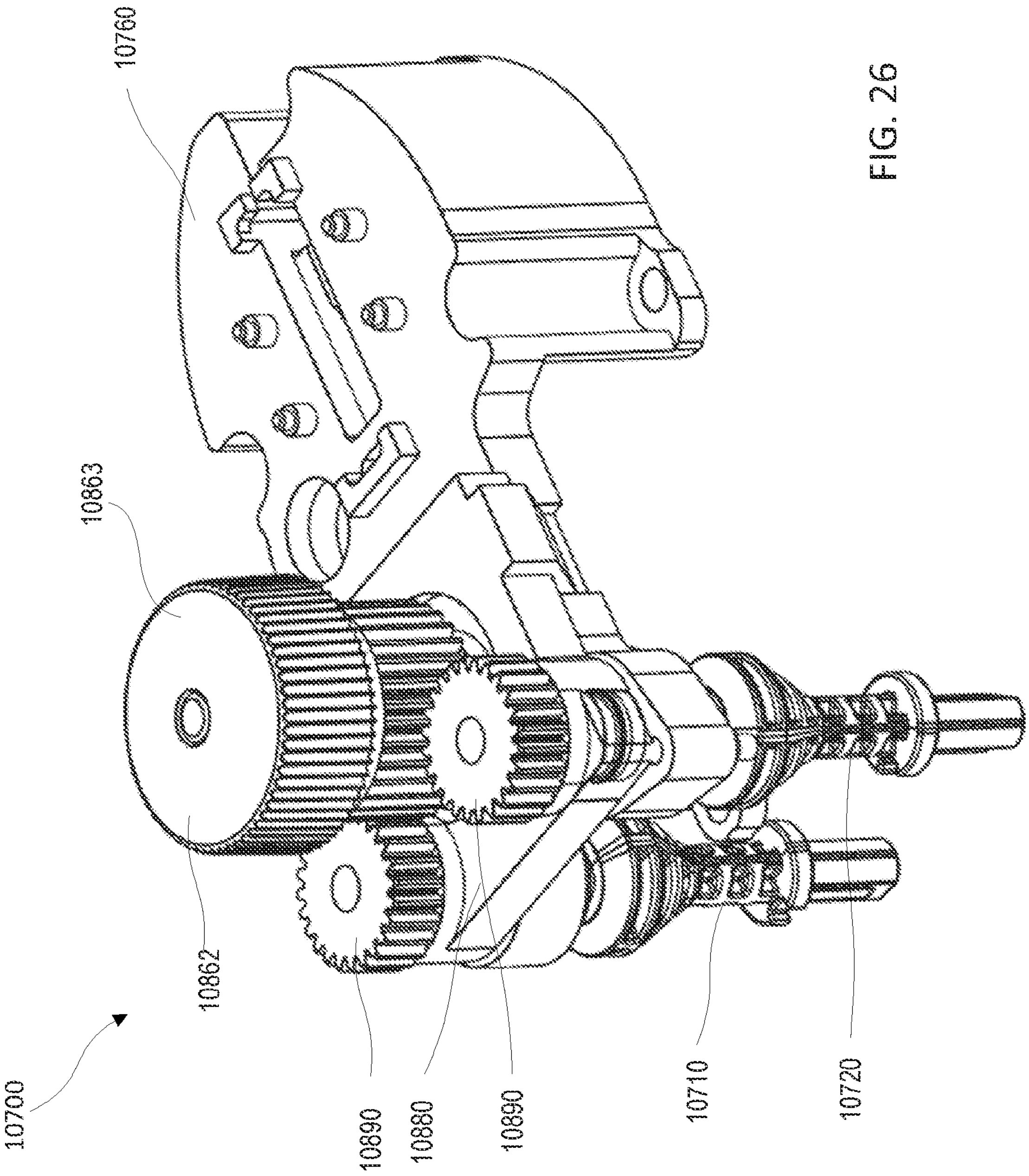
FIG. 26 is a perspective view of a portion of a medical device for manual tool adjustment according to an embodiment.

The different states in which the manual drive structure 9860 operates is based on the translation of the manual drive coupling member 9890 along the guide 9894. FIG. 24 shows the manual drive structure 9860 in the first state without engagement between the manual drive input 9862 and the capstans 9710, 9720. FIG. 25 shows the manual drive structure 9860 in the second state with engagement between the manual drive input 9862 and the capstans 9710, 9720. Thus, when in the first state rotation of the manual drive coupling member 9890 does not cause rotation of the capstans 9710, 9720. Likewise, torque on the capstans does not cause torque on the manual drive input 9862. When in the second state, rotation of the manual drive coupling member 9890 causes rotation of the capstans 9710, 9720. Likewise, a torque on the capstans results in a torque on the manual drive input 9862.

The manual drive structure 9860 also includes a biasing member. The biasing member 9876 is configured to bias the manual drive coupling member 9890 back to the first state. As shown in FIG. 23, the biasing member 9876 is a spring positioned against the manual drive coupling member 9890 and against a separate stop or the upper chassis. The spring places a linear force on the manual drive coupling member 9890 to bias it to the first state.

Because the manual drive coupling member 9890 is disengaged from the first capstan gear 9868 and the second capstan gear 9869 in the first state, the manual drive coupling member 9890 limits interference (e.g., back drive) from the first capstan 9710 and the second capstan 9720 to the manual drive input member 9862. This also allows the first capstan 9710 and the second capstan 9720 to operate independently of one another (e.g., they can rotate independently, sometimes in the same direction, sometimes in opposite directions of one another, and sometimes one can be stationary while the other rotates).

Selective engageability of the manual control of the surgical device allows for simplicity in operation of the device while providing redundancy of tool opening operation. By providing the manual interface 9863 and selective engageability as described above, the manual drive structure can be controlled and operated while the instrument is mounted on an associated teleoperated manipulator without the need for using a separate tool, instead being accessible and engaged by the hands of the user. Having the manual interface engage when desired removes undesirable distractions due to movement of the exterior features of the medical device, thereby improving the usability of the medical device in a clinical setting.

In another embodiment, as shown in FIGS. 26-32C, the manual drive structure 10860 includes a structure that also slides (i.e., translates) between a first state and a second state. FIGS. 26-32C illustrate a portion of a proximal mechanical structure 10700. Other portions of the medical device are omitted for clarity, but it is understood that the mechanical structure 10700 can be incorporated with any of the medical devices described herein. As such, it is understood that the mechanical structure 10700 can be coupled to and used with any end effectors (e.g., the end effector 8460), shafts (e.g., the shaft 8410), or any other components from the various embodiments discussed and detailed herein.

The proximal mechanical structure 10700 includes a chassis 10760, a first capstan 10710, a second capstan 10720, and a manual drive structure 10860. The mechanical structure 10700 includes other components and structure not shown or identified but which are similar to components and structure described with reference to the proximal mechanical structure 8700. For example, the proximal mechanical structure 10700 can include a lower chassis similar to the lower chassis 8762 described above.

Figure 29:
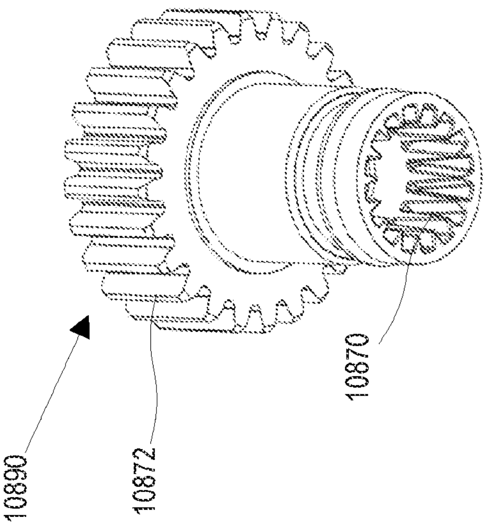
FIG. 29 a perspective view of a manual drive coupling of the medical device of FIG. 26.
Figure 28:
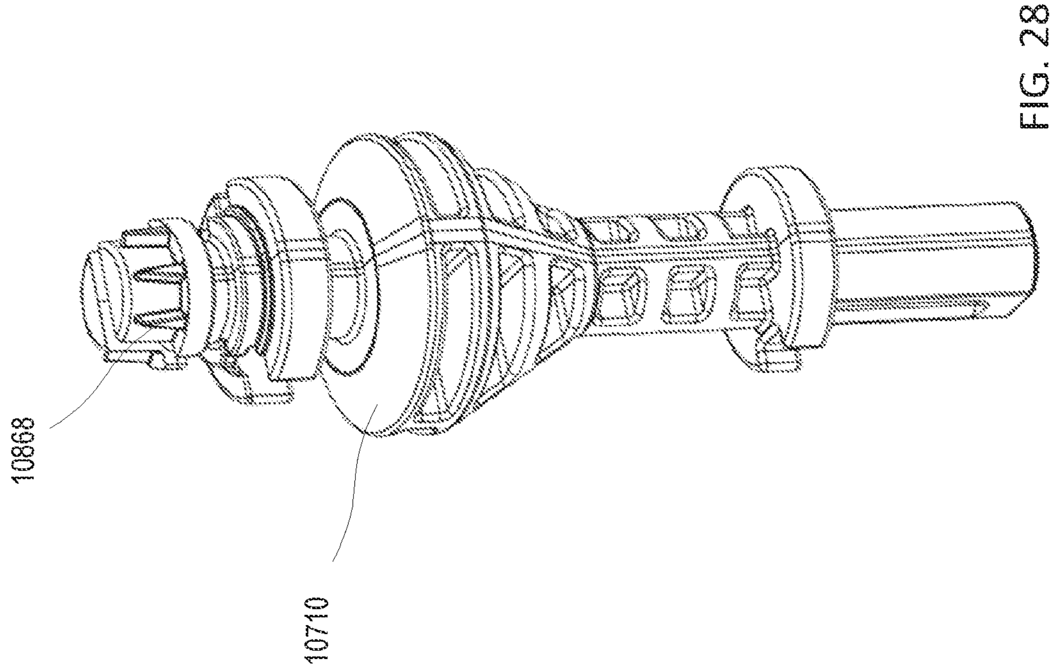
FIG. 28 a perspective view of a capstan of the medical of the medical device of FIG. 26.
Figure 30:
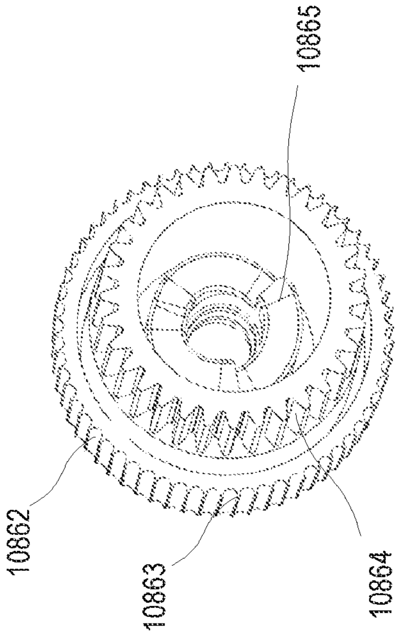
FIG. 30 a perspective view of a manual drive input member of the medical device of FIG. 26.

The manual drive structure 10860 includes a manual drive input member 10862, a manual drive coupler 10890, a biasing mechanism 10876, a guide 10894A, a first capstan manual drive input 10868 and a second capstan manual drive input 10869. As shown in FIGS. 26-32C, the manual drive input member 10862 includes a manual interface 10863, a manual drive engagement member 10864, and manual drive coupling path 10865. The manual interface 10863 includes a surface that is exposed to the exterior of the medical device. The user can engage the manual interface 10863 and manipulate the manual drive structure 10860, thereby manipulating the end effector. The exposed portion of the manual interface 10863 can include knurls, ridges, or other traction features on the surfaces suitable for the user to apply a torque to the manual drive input member 10862 via the manual interface 10863. The manual interface is defined by a rotatable knob that receives the user's input force and allows the manual drive structure 10860 to convert the user's input force to a torque on the first capstan 10710 and the second capstan 10720 and thereby manipulate the end effector via cables (not shown, but which are similar to the cables 8420 and 8430 described above). The manual drive engagement member 10864 is connected to and receives the torque applied to the manual interface 10863. As shown in FIG. 30, the manual drive coupling path 10865 includes a series of ramped surfaces within the manual interface 10863 knob that are suitable to engage with a portion of the bracket 10880. This interface can produce translation of the bracket 10880 and the manual drive couplers 10890, as described below.

Figure 27:
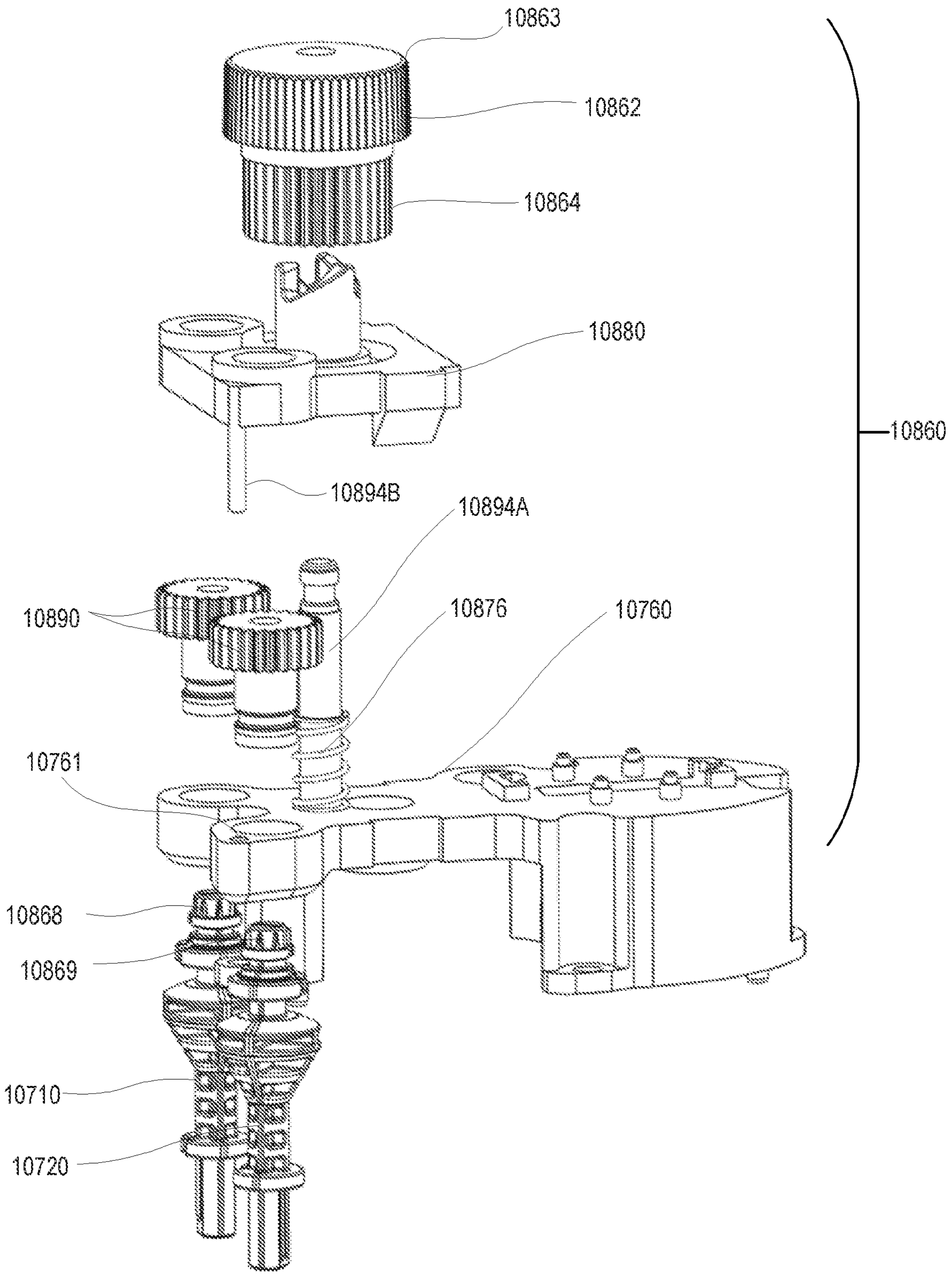
FIG. 27 an exploded view of a portion of the medical device of FIG. 26.

The manual drive couplers 10890 allow for selective engageability between the manual drive input member 10862 and the capstans 10710, 10720. The manual drive couplers 10890 include a tool-drive-side coupler 10870, a manual-drive-side coupling gear 10872, and are coupled to the movable bracket 10880. As shown in FIG. 29, the tool-drive-side coupler 10870 is a socket formed within a protrusion from the manual-drive-side coupling gear 10872. The socket can include internal teeth suitable to engage the exterior of an opposing protrusion having external teeth. Specifically, the internal teeth can engage the first capstan manual drive input 10868 and the second capstan manual drive input 10869. The manual-drive-side coupling gear 10872 includes teeth configured to engage with the teeth of the manual drive input member 10862. The bracket 10880 is configured to receive one or more of the manual drive couplers 10890. As shown in FIG. 27, the bracket 10880 can support two manual drive couplers 10890. Thus, as described below movement of the bracket 10880 produces movement of the manual drive couplers 10890.

Figure 31:
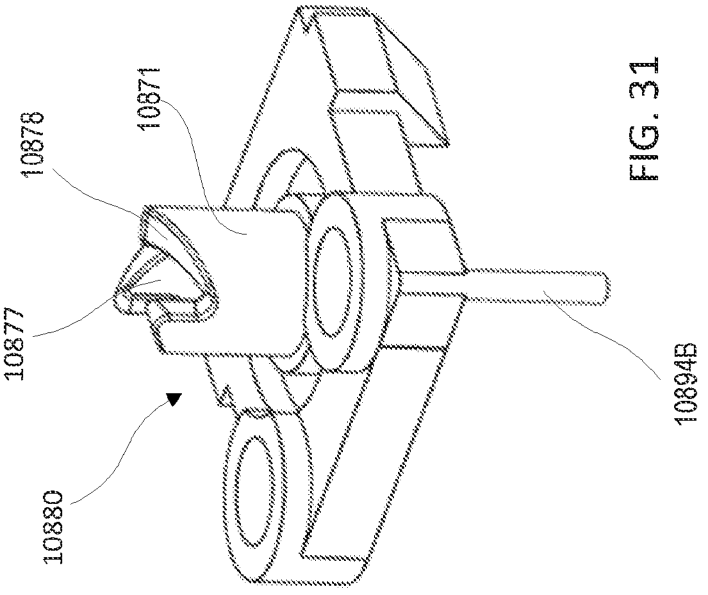
FIG. 31 a perspective view of a mounting bracket of the medical device of FIG. 26.

As shown in FIG. 31, the bracket 10880 includes a protrusion 10871 defining a guide surface that includes a series of ramped surfaces 10865 that correspond with and are configured to engage with the ramped surfaces of the manual drive coupling path 10865. The protrusion 10871 defines an aperture 10877 configured to receive the guide 10894A. In this manner, the bracket 10880 can slide about guide 10894A, thus ensuring linear motion along the desired axis. The bracket 10880 also includes a coupling guide 10894B which allows for translation of and limitation of rotation of the manual drive couplers 10890 and the manual drive input member 10862. The coupling guide 10894B can be parallel to the aperture 10877 and is received into an aperture in the chassis 10760. Thus, the bracket 10880 is constrained to translational movement along the guide 10894A without a rotational degree of freedom.

The manual drive couplers 10890 are connected to the manual drive input member 10862 via engagement between the manual-drive-side coupling gear 10872 and the manual drive input gear member 10864. Rotation of the manual interface member 10863 causes rotation of the manual-drive-side coupling gear 10872. The manual drive coupler 10890 is selectably connected to the capstan manual drive inputs 10868, 10869. The capstan drive inputs include the protrusion with exterior teeth that correspond to the socket of the tool-drive-side coupler 10870. As shown, the teeth of the capstan manual drive inputs 10868, 10869 are tapered, having a smaller width at the side facing the manual drive couplers 10890 and a larger width towards the base of the protrusion. The tapered teeth allow for the socket 10870 to engage over the teeth is the drive couplers 10890 rotate and move downward over the teeth.

Figure 32C:
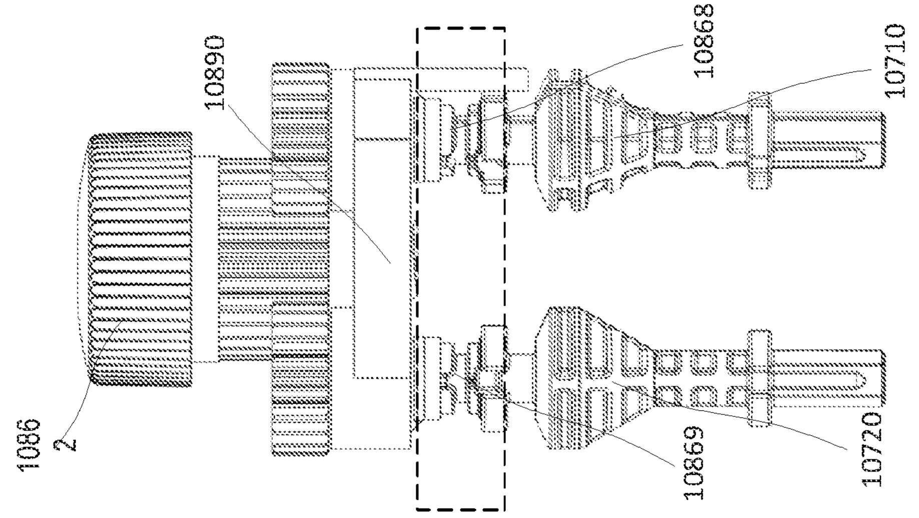
FIGS. 32A-C are front cross-sectional views of the medical device of FIG. 26, with FIG. 32A in a first state, FIG. 32B in a second state, and FIG. 32C in a third state.
Figure 32B:
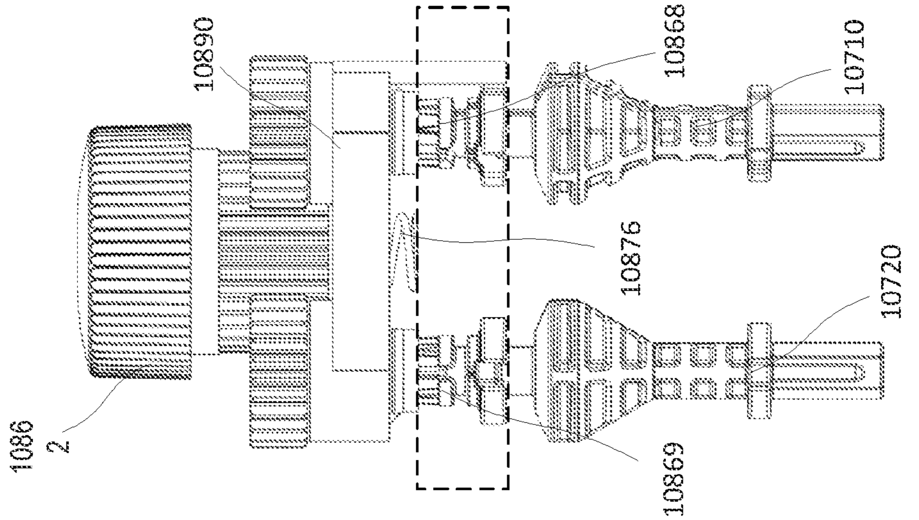
Figure 32A:
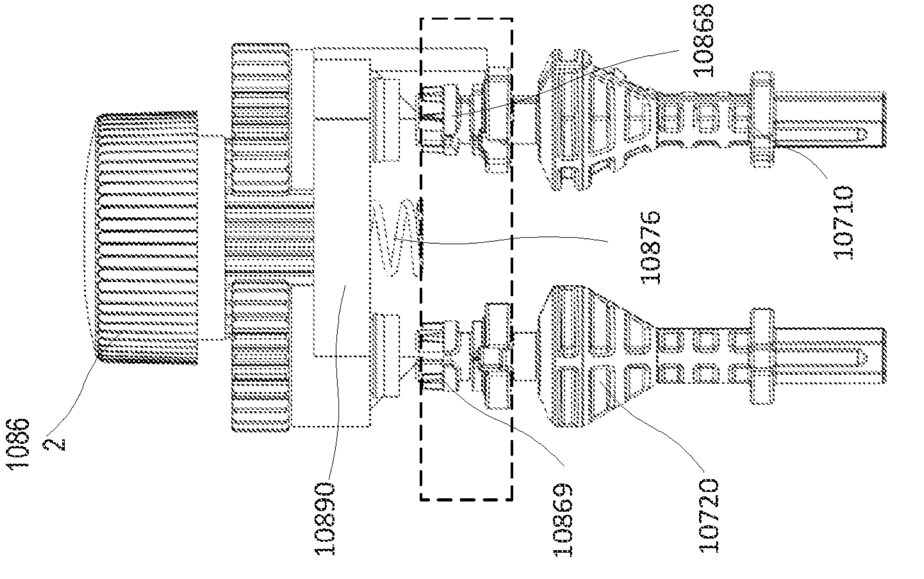

In a first state, the manual drive coupler 10890 is biased away from the capstan manual drive inputs 10868, 10869 (see e.g., FIG. 32A). As the manual drive input member 10862 is rotated, the ramps 10865 on protrusion 10871 and the manual drive coupling path 10865 engage one another. The manual drive input member 10862 is secured in place along the length of the guide 10894A. Thus, the manual drive coupling path 10865 forces the guide surfaces on protrusion 10871 to follow the series of ramped surfaces, thereby forcing the bracket 10880 away from the manual drive input member 10862 as it rotates. This occurs until the manual drive structure 10860 achieves a second state in which the manual drive structure engages with the capstan manual drive inputs 10868, 10869. Continued rotation of the manual drive input member 10862 causes rotation of the first capstan 10710 and the second capstan 10720 (i.e., to open the jaw, not shown). However, after a predetermined amount of rotation, the biasing member 10876 (e.g., coil spring) forces the manual drive input member 10862 and the bracket 10880 back together due to the profile of the series of ramped surfaces. The amount of rotation is related to the ramps 10865 around the protrusions 10871 and 10865. As shown in FIGS. 30-31, there is a series of three ramped surfaces 10865, which allow for rotation of about 120 degrees before the end of one ramp transitions back to the beginning of the second ramp. During this transition to the beginning of another ramp, the biasing member 10876 causes the bracket 10880 (and the manual drive couplers 10890) to move upwards towards the manual drive input member 10862 (i.e., towards the first state). Similarly stated, with a series of three ramped surfaces, the separation between the bracket 10880 and the manual drive input member 10862 is reset about every third of a full rotation because of the equal spacing of the ramped surfaces as shown in FIGS. 30-31. However, in other embodiments, there can be one, two, four, or five or more.

The two manual-drive-side coupling gears 10872 are positioned relative to the bracket 10880 (while allowing for rotational freedom). Thus, as the bracket 10880 translates along the guide 10984A, the two manual-drive-side coupling gears 10872 also translate along the guide. In the second state, the tool-drive-side coupling gear 10870 of the manual drive coupler 10890 is engaged with the capstan manual drive inputs 10868, 10869. In this position, the internal teeth of the socket 10870 and the teeth of the capstan manual drive inputs 10868, 10869 engage with one another, transferring torque therebetween. The capstan manual drive inputs 10868, 10869 are formed as a portion of the capstans 10710 and 10720, causing torque from the manual drive structure 10860 to be directed into the capstans 10710 and 10720. Thus, the manual drive coupler 10890 transmits the user's force from the manual drive input member 10862 to both the first capstan 10710 and the second capstan 10720. This allows the capstans to direct the force via the cables to the end effector.

The different states in which the manual drive structure 10860 operates is based on the translation of the manual drive coupler 10890. FIGS. 32A-32C show the progression of the manual drive structure 10860 from the first state without engagement between the manual drive input 10862 and the capstans 10710, 10720 to the second state with engagement between the manual drive input 10862 and the capstans 10710, 10720. Thus, in the first state, rotation of the manual drive coupler 10890 does not cause rotation of the capstans 10710, 10720. Likewise, torque on the capstans does not cause torque on the manual drive input 10862. Similarly stated, the manual drive coupler 10890 is isolated from the first capstan 10710 and the second capstan 10720. In the second state, rotation of the manual drive coupler 10890 causes rotation of the capstans 10710, 10720. Likewise, a torque on the capstans results in a torque on the manual drive input 10862.

Because the manual drive couplers 10890 are disengaged from the capstan manual drive inputs 10868, 10869 in the first state, the manual drive couplers 10890 limit interference (e.g., back drive) from the first capstan 10710 and the second capstan 10720 to the manual drive input member 10862. This also allows the first capstan 10710 and the second capstan 10720 to operate independently of one another (e.g., they can rotate independently, sometimes in the same direction, sometimes in opposite directions of one another, and sometimes one can be stationary while the other rotates).

Selective engageability of the manual control of the surgical device allows for simplicity in operation of the device while providing redundancy of tool opening operation. By providing the manual interface 10863 and selective engageability as described above, the manual drive structure can be controlled and operated while the instrument is mounted on an associated teleoperated manipulator without the need for using a separate tool, instead being accessible and engaged by the hands of the user. Having the manual interface engage when desired removes undesirable distractions due to movement of the exterior features of the medical device, thereby improving the usability of the medical device in a clinical setting.

Figure 34:
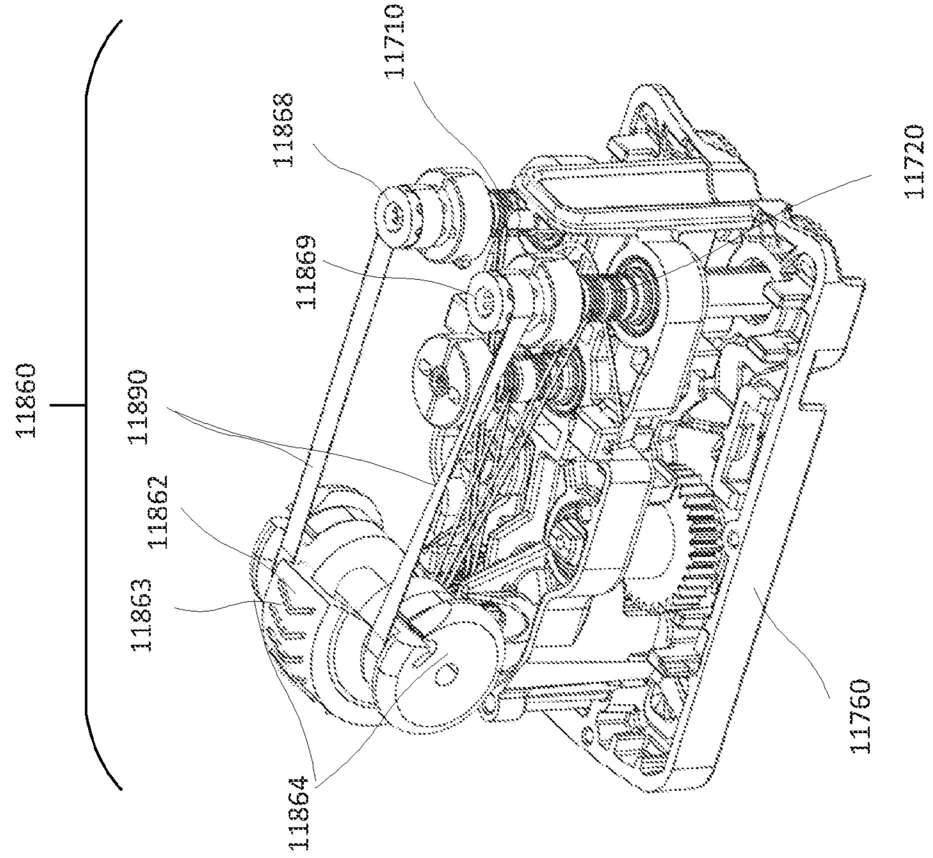
FIG. 34 is a perspective view of a portion of the medical device of FIG. 33 with the top cover removed to show the internal components.
Figure 33:
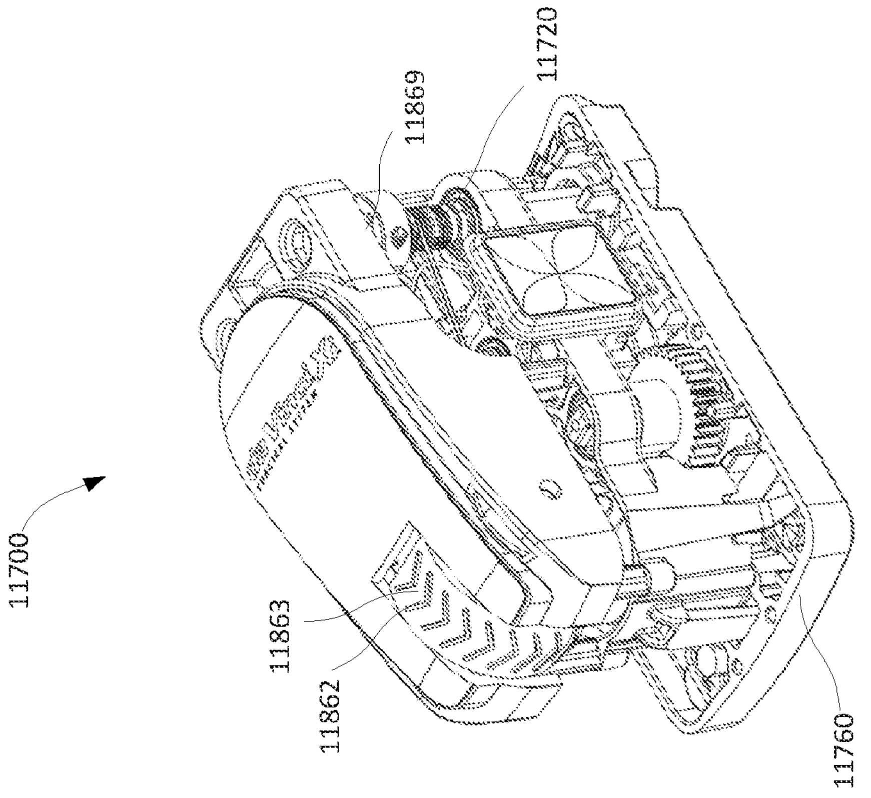
FIG. 33 is a perspective view of a portion of a medical device for manual tool adjustment according to an embodiment.
Figure 35:
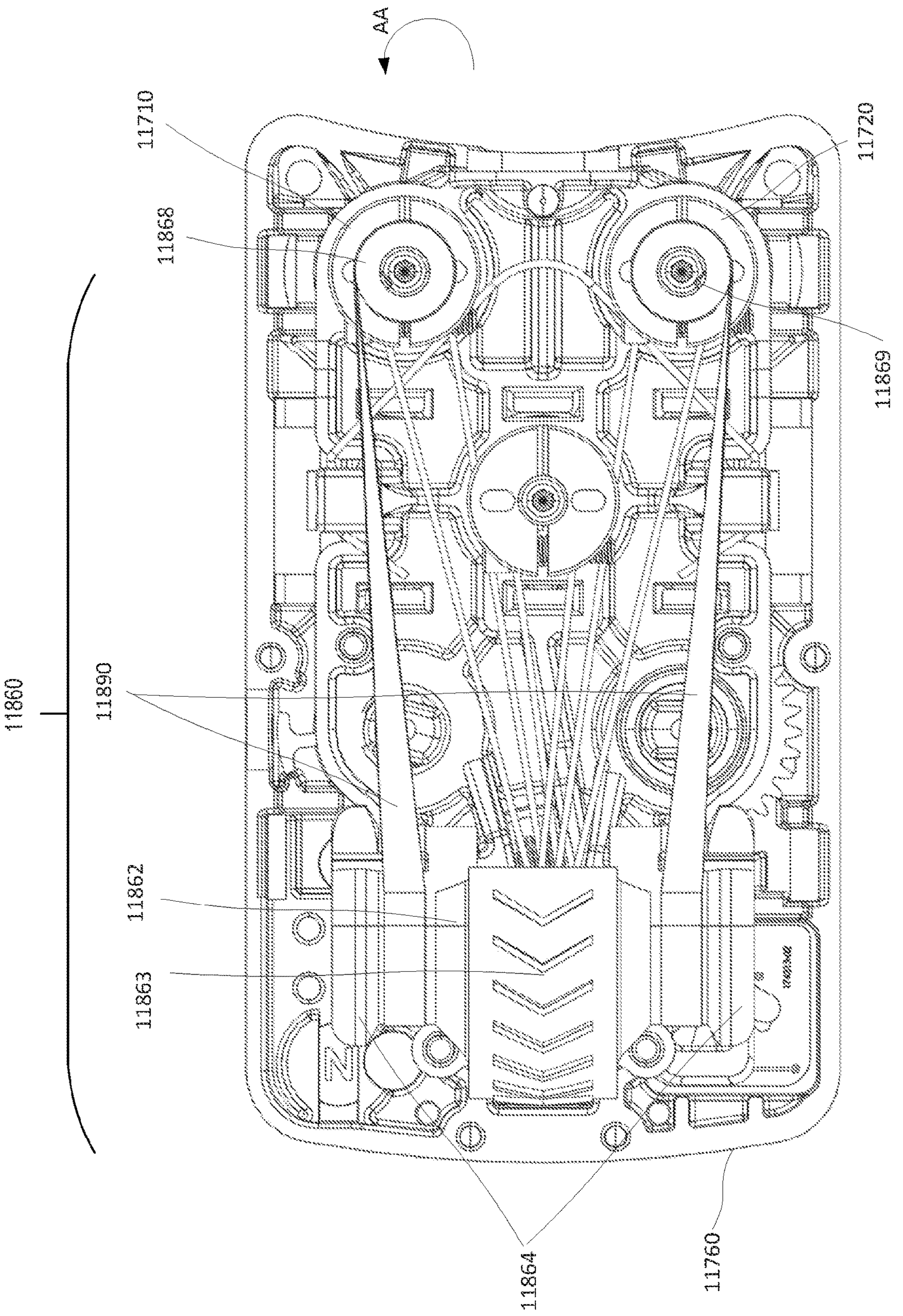
FIG. 35 a top view of a portion of the medical device of FIG. 33.

In another embodiment, as shown in FIGS. 33-35, the manual drive structure 11860 provides a continuous engagement between the manual drive structure 11860 and the capstans 11710 and 11720 in contrast to FIGS. 10-21B, which showed a structure that operated between a first state (with no engagement) and a second state (with an active engagement). Other portions of the medical device are omitted for clarity, but it is understood that the manual drive structure 11860 can be coupled to and used with any end effectors (e.g., the end effector 8460)), shafts (e.g., the shaft 8410), or any other components from the various embodiments discussed and detailed herein.

The proximal mechanical structure 11700 includes a chassis 11760, a first capstan 11710, a second capstan 11720, and the manual drive structure 11860. The mechanical structure 11700 includes other components and structure not shown or identified in FIGS. 33-35 but which are similar to components and structure described with reference to the proximal mechanical structure 8700. For example, the proximal mechanical structure 11700 includes a lower chassis similar to the lower chassis 8762 described above.

The manual drive structure 11860 includes a manual drive input member 11862, two tension members 11890 (which function as manual drive couplers), and two capstan manual drive inputs 11868, 11869. As shown in FIGS. 33-35, the manual drive input member 11862 includes a manual interface 11863 and two manual drive engagement members 11864. The manual interface 11863 includes a surface that is exposed to the exterior of the medical device. The user can engage the manual interface 11863 and manipulate the manual drive structure 11860, thereby manipulating the end effector. The exposed portion of the manual interface 11863 can include knurls, ridges, or other traction features on the surfaces suitable for the user to apply a torque to the manual drive input member 11862 via the manual interface 11863. As shown in FIGS. 33-35, the manual interface 11863 functions as a rotatable thumb wheel that receives the user's input force and allows the manual drive structure 11860 to convert the user's input force to a torque on the first capstan 11710 and the second capstan 11720 and thereby manipulate the end effector via cables. The manual drive engagement members 11864 are connected to and receive the torque applied to the manual interface 11863. As shown in FIG. 35, the manual drive engagement members 11864 includes one or more protrusions defining cylindrical surfaces that extend along the axis of the manual interface 11863 outwardly. The cylindrical surfaces are coupled to and form a wrapping surface for a corresponding tension member 11890.

Each tension member 11890 extends between the manual drive input member 11862 and one of the capstans 11710, 11720. As shown in FIGS. 33-35, each tension member 11890 includes a pair of flexible ends (i.e., straps) wrapped around one of the manual drive engagement members 11864 on one end and around one of the capstan manual drive inputs 11868, 11869 on the other end. The tension members 11890 can be connected to the manual drive engagement members 11864 in any suitable manner including clamping, a slotted fit, adhesive, etc. As shown in FIG. 34, rotation of the manual interface member 11863 causes rotation of the manual drive engagement members 11864. The tension members 11890 are directly connected to the capstan manual drive inputs 11868, 11869 from the manual drive engagement members 11864. The tension member 11890 is wrapped around the outer circumference of the capstan manual drive inputs 11868, 11869 such that pulling on the tension member 11890 will impart a torque on the capstan manual drive inputs 11868, 11869. Thus, as the manual interface thumb wheel 11863 is turned such that tension is placed on the tension member 11890, the tension member 11890 pulls on the outer circumference of the capstan manual drive inputs 11868, 11869, imparting a torque thereon. This causes the capstans 11710 and 11720 to direct the force via the cables to the end effector. While tension on the tension member 11890 causes a torque to be imparted to the capstan manual drive inputs 11868, 11869, in certain operational configurations, the opposite is not true. For example, a torque on the capstan manual drive input 11868 (e.g., produced by a motor input to the first capstan 11710 or a force applied to the end effector) in the direction that the tension member 11890 pulls (shown in FIG. 35) will cause the tension member 11890 to go slack instead of imparting a torque on the manual drive input member 11862. Tensioning the tension member 11890 at one extreme rotation of the capstans (i.e., the position of the capstans when the end effector is in a closed position) also reduces the ability of the capstans to impart a torque to the manual drive input member 11862. In this way, the tension members 11890 limit the ability of the capstans to back drive the manual drive input member 11862. Additionally, in some embodiments, the amount of torque transferred from the tension members 11890 to the capstans will vary as a function of the rotational position of the capstan. As shown in FIG. 35, when the capstan 11710 is at a rotational position at which the tension member 11890 exits the capstan 11710 tangent to the cylindrical surface of the capstan 11710, the moment distance from the axis of rotation is equal to the diameter of the capstan 11710. This is a configuration where the maximum torque can be applied by the tension member 11890 to the capstan 11710. As the tension members 11890 pull the capstan 11710 around (i.e. in the direction shown by the arrow AA), depending on the number of wraps that the end of the tension member 11890 makes about the capstan 11710, the tension member 11890 may no longer exit the capstan 11710 tangent to the cylindrical surface of the capstan 11710. Similarly stated, the capstan 11710 may rotate to the point where the tension members 11890 extends directly away from the capstan 11710. At such an orientation, the moment distance through which the force applied by the tension member 11890 about the axis of rotation decreases (i.e., it is less than the diameter of the capstan 11710). At some rotational positions, the moment distance can by substantially zero and the tension member 11890 does not apply any torque to rotate the capstan 11710. Said another way, the tension members 11890 lose their ability to apply a torque to the capstan because the line of force from the tension member passes directly through the axis of rotation of the capstans 11710 and 11720. This limits the tension member from over torquing the capstans 11710 and 11720 and the end effector as a result.

Limited back drive of the manual control of the surgical device allows for simplicity in operation of the device while providing redundancy of tool opening operation. By providing the manual interface 11863 with a limited back drive as described above, the manual drive structure can be controlled and operated while the instrument is mounted on an associated teleoperated manipulator without the need for using a separate tool, instead being accessible and engaged by the hands of the user. Having the manual interface engage when desired removes undesirable distractions due to movement of the exterior features of the medical device thereby improving the usability of the medical device in a clinical setting.

In another embodiment, as shown in FIGS. 36-39, the manual drive structure 12860) includes a structure with an automatic engagement between the manual drive structure 12860) and the capstans 12710 and 12720 on condition that the manual input member 12862 is rotated in an engagement direction, but the manual drive structure has no connection with the capstans on condition that the manual input member is rotated in a non-engagement direction. Other portions of the medical device are omitted for clarity, but it is understood that the mechanical structure 12700 can be incorporated with any of the medical devices described herein. As such, it is understood that the mechanical structure 12700 can be coupled to and used with any end effectors (e.g., the end effector 8460), shafts (e.g., the shaft 8410), or any other components from the various embodiments discussed and detailed herein.

The proximal mechanical structure 12700 includes a chassis 12760, a first capstan 12710, a second capstan 12720, and the manual drive structure 12860. The mechanical structure 12700 includes other components and structure not shown or identified in FIGS. 36-39 but which are similar to components and structure described with reference to the proximal mechanical structure 8700. For example, the proximal mechanical structure 12700 includes a lower chassis similar to the lower chassis 8762 described above.

Figure 37:
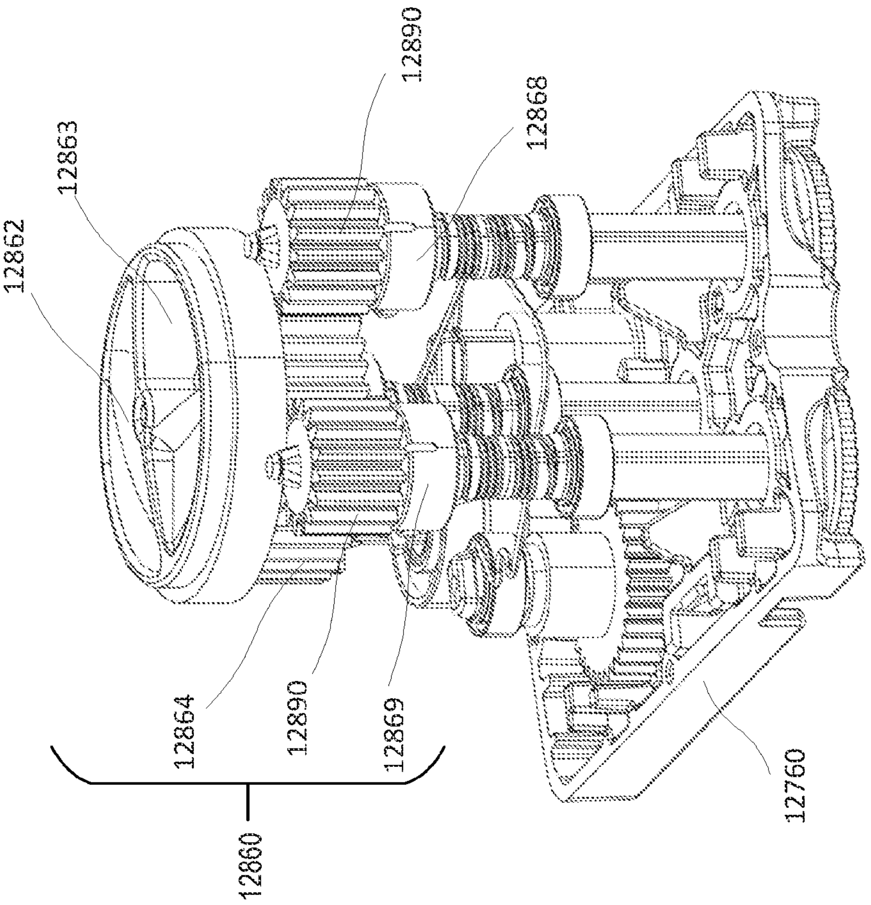
FIG. 37 a perspective view of a portion of the medical device of FIG. 36 with the cover removed to show the internal components.
Figure 36:
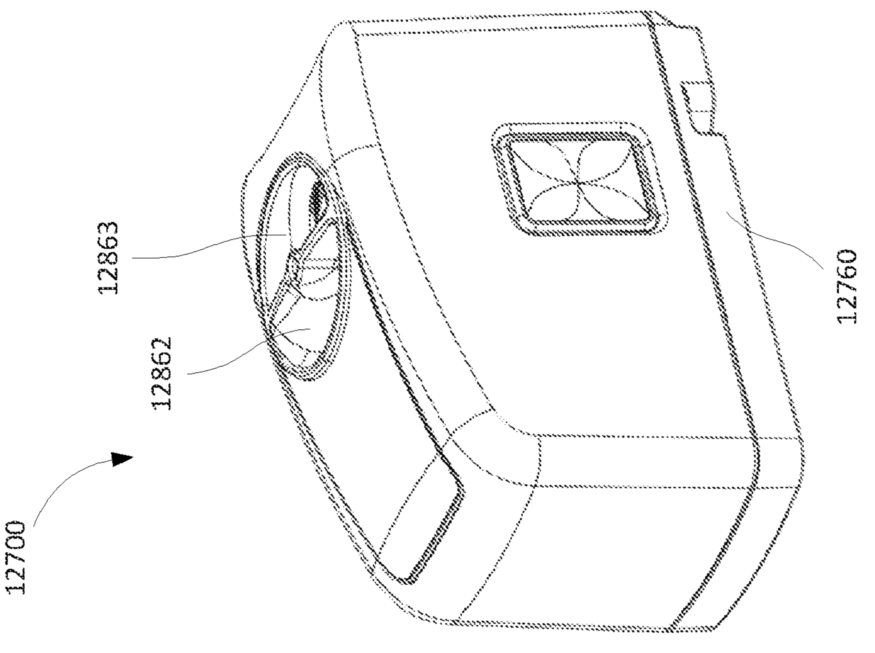
FIG. 36 is a side perspective view of a portion of a medical device or manual tool adjustment according to an embodiment.
Figure 38:
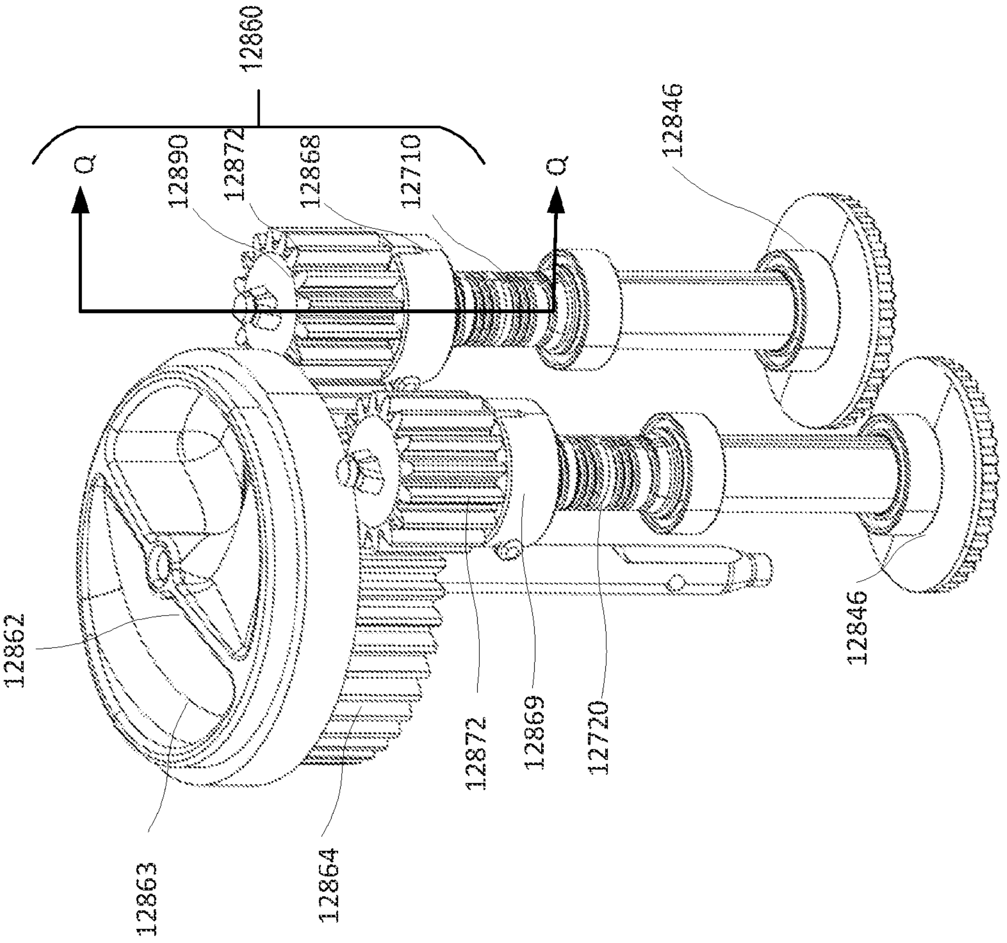
FIG. 38 a perspective view of a portion of the medical device of FIG. 36.

The manual drive structure 12860 includes a manual drive input member 12862, a manual drive coupler 12890, and one or more capstan manual drive inputs 12868, 12869. As shown in FIGS. 37-38, the manual drive input member 12862 includes a manual interface 12863 and a manual drive gear 12864. The manual interface 12863 includes a surface that is exposed to the exterior of the medical device. The user can engage the manual interface 12863 and manipulate the manual drive structure 12860, thereby manipulating the end effector. The exposed portion of the manual interface 12863 can include knurls, ridges, or other traction features on the surfaces suitable for the user to apply a torque to the manual drive input member 12862 via the manual interface 12863. As shown in FIGS. 37-38, the manual interface 12863 is defined by a rotatable dial that receives the user's input force and allows the manual drive structure 12860 to convert the user's input force to a torque on the capstans 12710, 12720 and thereby manipulate the end effector via cables. The manual drive gear 12864 is connected to and receives the torque applied to the manual interface 12863.

Figure 39:
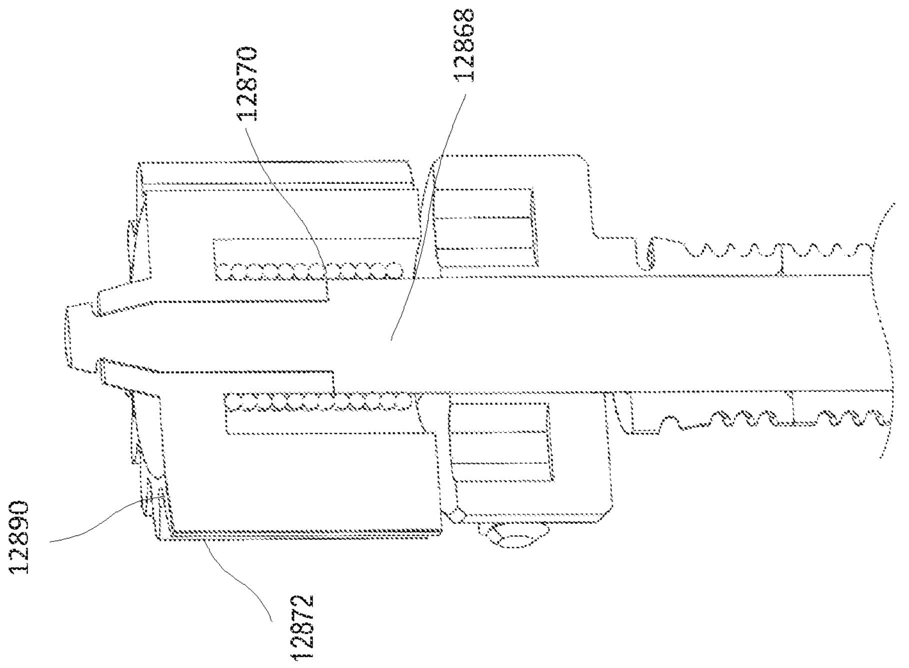
FIG. 39 a cross-sectional view of a portion of the manual coupling element of FIG. 38 taken along section line Q-Q.

The manual drive coupler 12890 includes a one-way clutch that is positioned between the manual drive input member 12862 and the capstans 12710, 12720. The one-way clutch transmits torque on condition that it is rotated in one direction but does not transmit torque on the condition that it is rotated in the opposite direction. As shown in FIG. 39, the manual drive coupler 12890 includes a pair of one-way clutches. Each clutch drives a separate capstan 12710 and 12720. The manual drive couplers 12890 each include a tool-drive-side clutch 12870 and a manual-drive-side coupling gear 12872. The manual-drive-side coupling gear 12872 is a gear having teeth suitable of engaging the manual drive gear 12864. The tool-drive-side clutch 12870 can include any suitable one-way clutch mechanism. As shown in FIG. 39, the one-way clutch mechanism is a spring clutch. Each of the capstans 12710, 12720 includes a shaft 12868, 12869 that extends inside the manual drive coupler 12890. The manual-drive-side clutch 12872 includes a spring that wraps around the internal shaft (e.g., 12868, 12869) and engages the inner portion of the manual-drive-side coupling gear 12872. As the manual-drive-side coupling gear 12872 rotates in one direction, the spring is tightened around the internal shaft (e.g., 12868, 12869) transferring torque to it. As the manual-drive-side coupling gear 12872 rotates in the opposite direction, the spring is loosened around the internal shaft (e.g., 12868, 12869) limiting or preventing torque transfer.

Rotation of the manual interface member 12863 causes rotation of the manual drive engagement members 12864. The pair of one-way clutches included in the manual drive coupler 12890 are directly connected to the capstan manual drive inputs 12868, 12869 and between the capstan manual drive inputs 12868, 12869 and the manual drive gear 12864. Rotation of the manual interface member 12963 in a first direction will impart a torque on the capstan manual drive inputs 12868, 12869. This causes the capstans 12710 and 12720 to direct the force via the cables to the end effector. Rotation of the manual interface member 12963 in the opposite direction will release the one-way clutch on the capstan manual drive inputs 12868, 12869. This limits any torque transfer to the capstans 12710 and 12720.

The embodiment disclosed in FIGS. 36-39 is an example of the more general schematic disclosed in FIGS. 7A-7G. As such, FIGS. 7B-7G describes the various combinations of characteristics of the one-way clutch coupling of the manual drive structure 12860 disclosed in FIGS. 36-39.

Driving multiple capstans with a manual interface on a surgical device allows for simplicity in operation of the device while providing redundancy of tool opening operation. By providing the manual interface 12863 as described above, the manual drive structure can be controlled and operated while the instrument is mounted on an associated teleoperated manipulator without the need for using a separate tool, instead being accessible and engaged by the hands of the user, thereby improving the usability of the medical device in a clinical setting.

In another embodiment, as shown in FIGS. 40-43B, the manual drive structure 13860 of the proximal mechanical structure 13700 includes a chassis, a first capstan 13710, a second capstan 13720, a manual drive input member 13862, a manual drive coupler 13890, two capstan manual drive inputs 13868, 13869, a mechanical motor disconnect 13896, and motor coupling 13899. Other portions of the medical device are omitted for clarity, but it is understood that the mechanical structure 13700 can be incorporated with any of the medical devices described herein. As such, it is understood that the mechanical structure 13700 can be coupled to and used with any end effectors (e.g., the end effector 8460), shafts (e.g., the shaft 8410), or any other components from the various embodiments discussed and detailed herein.

Figure 41:
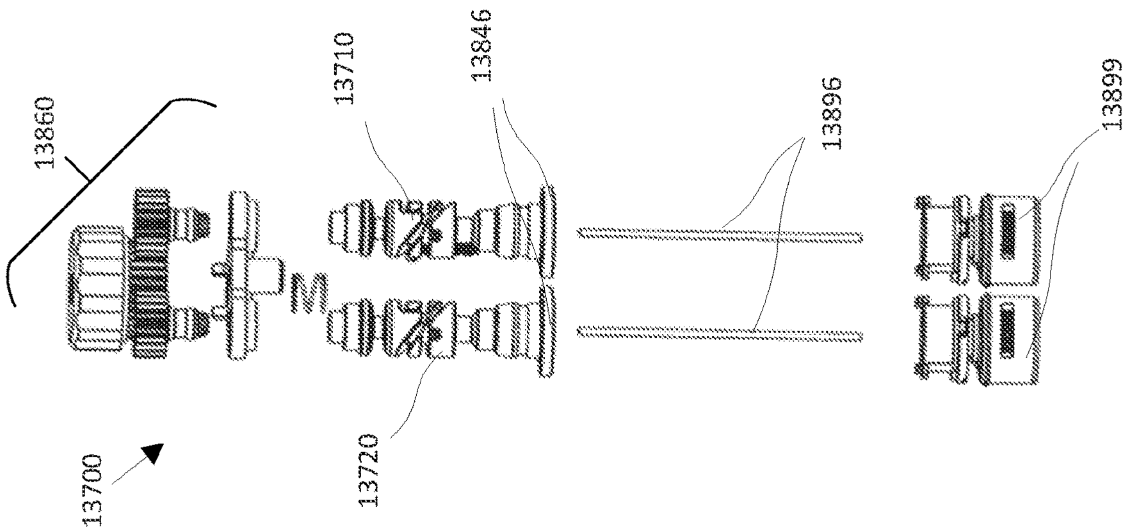
FIG. 41 an exploded view of a portion of the medical device of FIG. 40.
Figure 40:
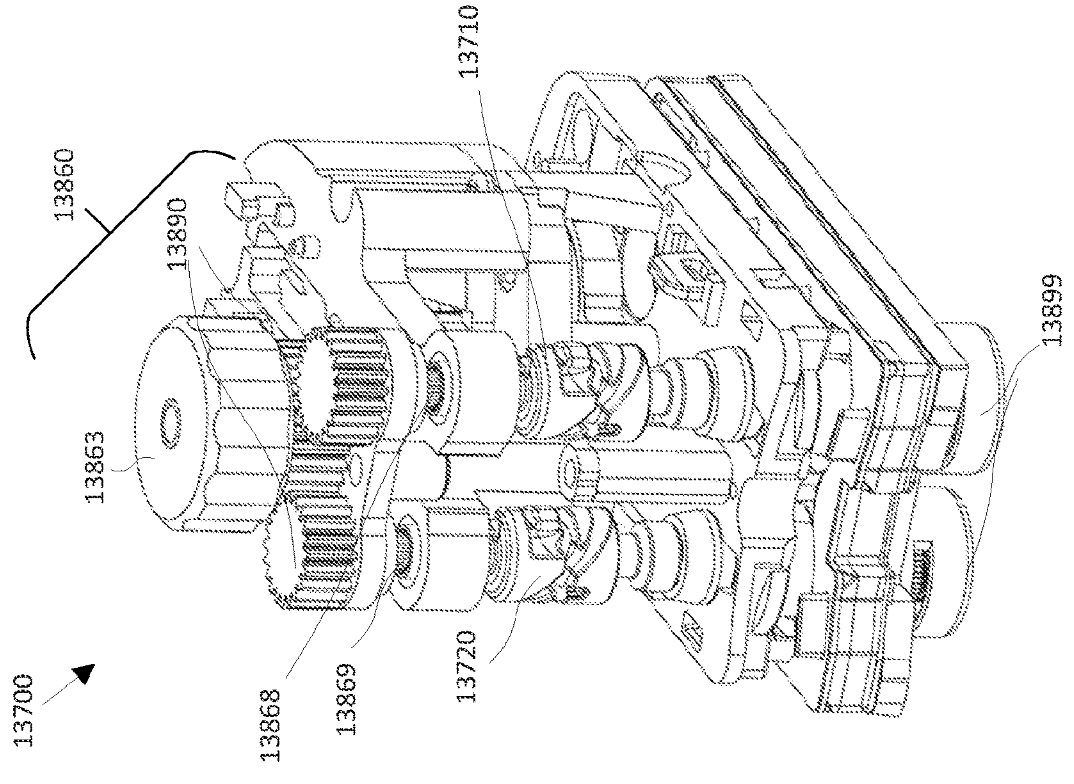
FIG. 40 is a perspective view of a portion of a medical device for manual tool adjustment and motor release according to an embodiment.
Figure 42A:
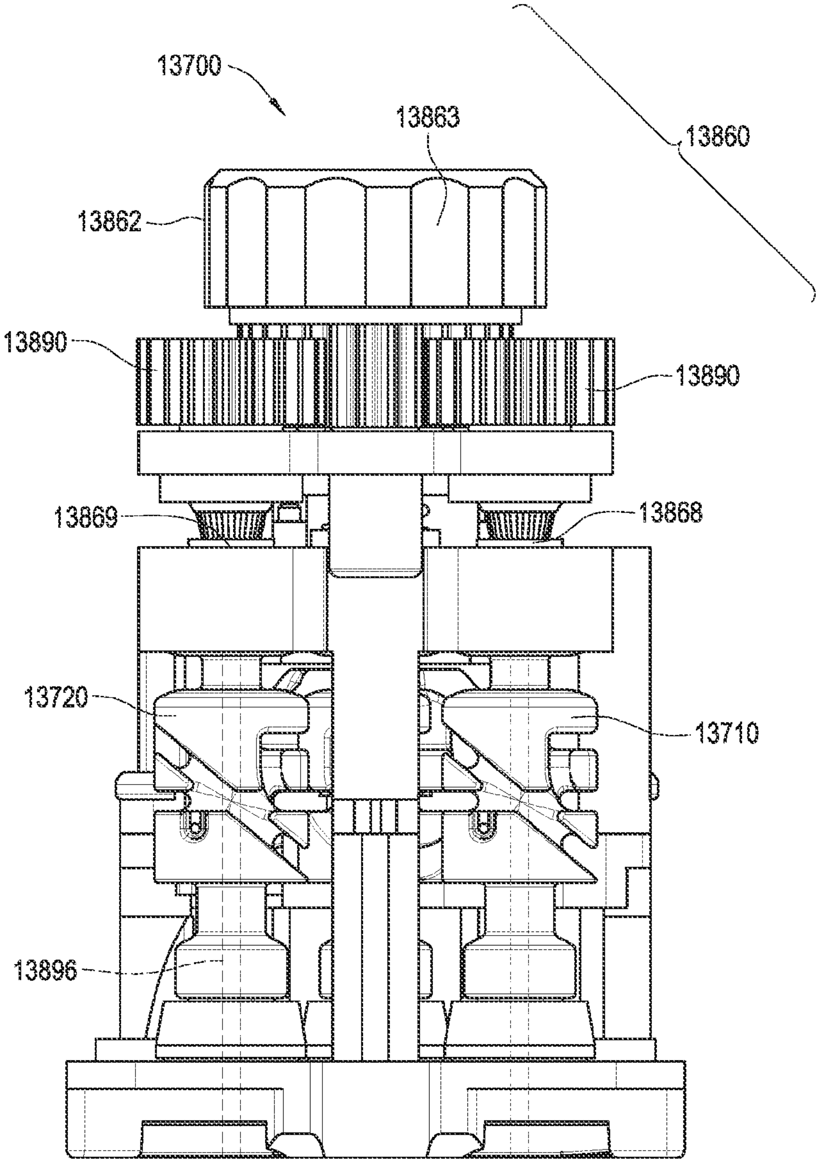
FIG. 42A-C are front views of a portion of the medical device of FIG. 40 showing a portion of the medical device in a first operation state (FIG. 40A), a second operation state (FIG. 40B), and a third operation state (FIG. 40C), the capstans are shown transparent.
Figure 42B:
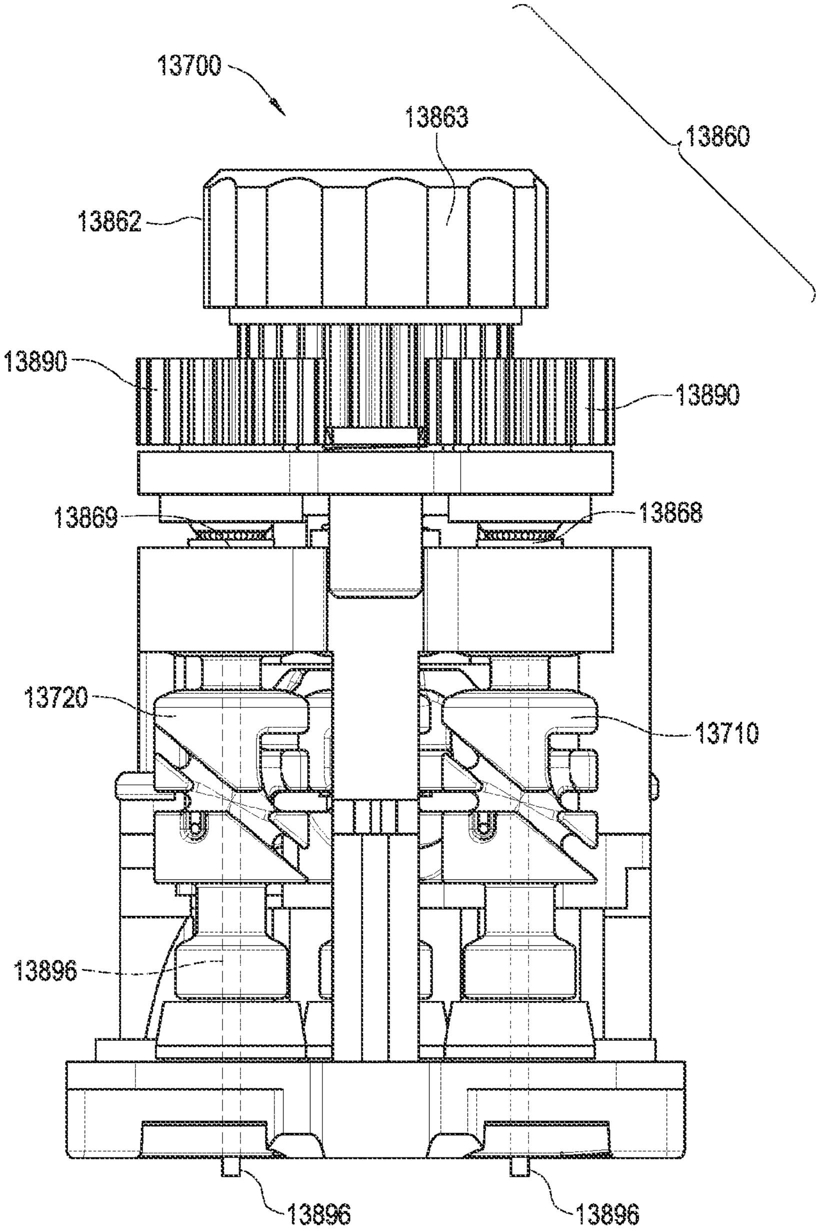
Figure 42C:
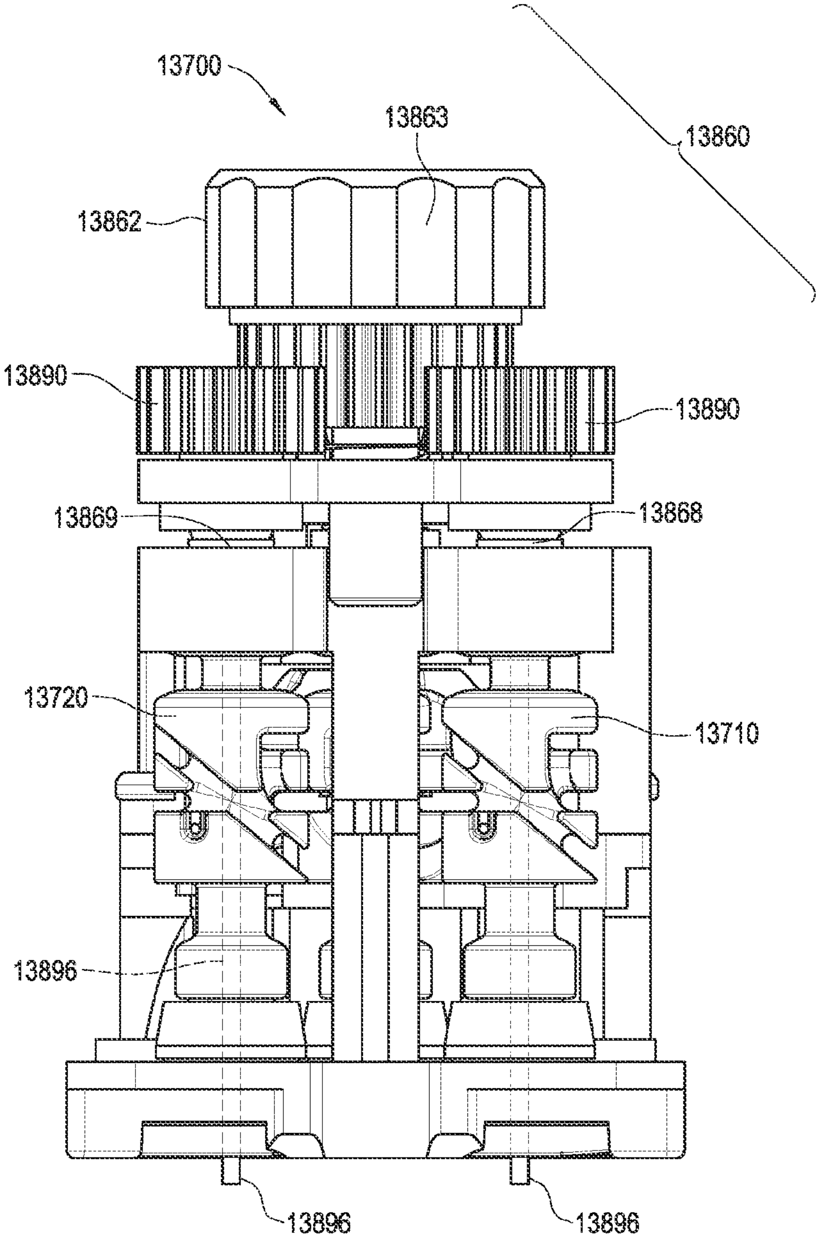

As shown in FIG. 41 the mechanical motor disconnect 13896 extend through the capstans 13720 and 13710 and extend down to the motor coupling 13899. As shown in FIGS. 42A-C, the mechanical motor disconnect 13896 is a rod that extends from the manual drive structure 13860 down through the proximal mechanical structure 13700 from the manual input member 13862 to the base of the structure 13700 where the drive disks 13846 are located. As the user engages the manual interface 13863, the mechanical motor disconnect 13896 is likewise actuated sliding down and extending out of the base at the drive disks 13846. Any suitable drive disk is usable in this arrangement such as those disclosed in U.S. Pat. No. 10,247,911 entitled "Instrument Sterile Adapter Drive Features," which is hereby incorporated by reference in its entirety.

Figure 43A:
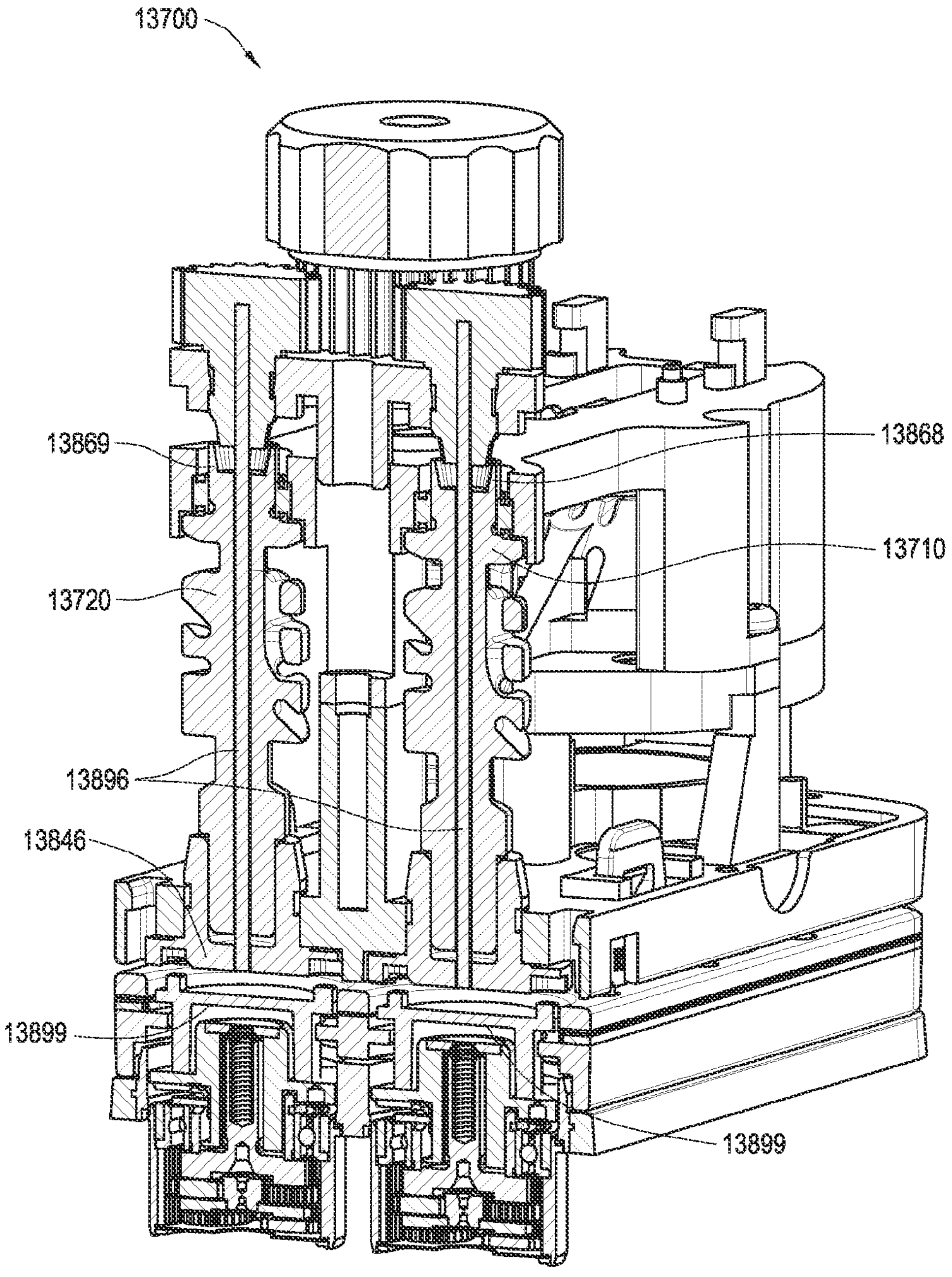
FIG. 43A-B are perspective cross-sectional views of a portion of the medical device of FIG. 40 showing a portion of the medical device in a first operation state (FIG. 43A) and a second operation state (FIG. 43B).
Figure 43B:
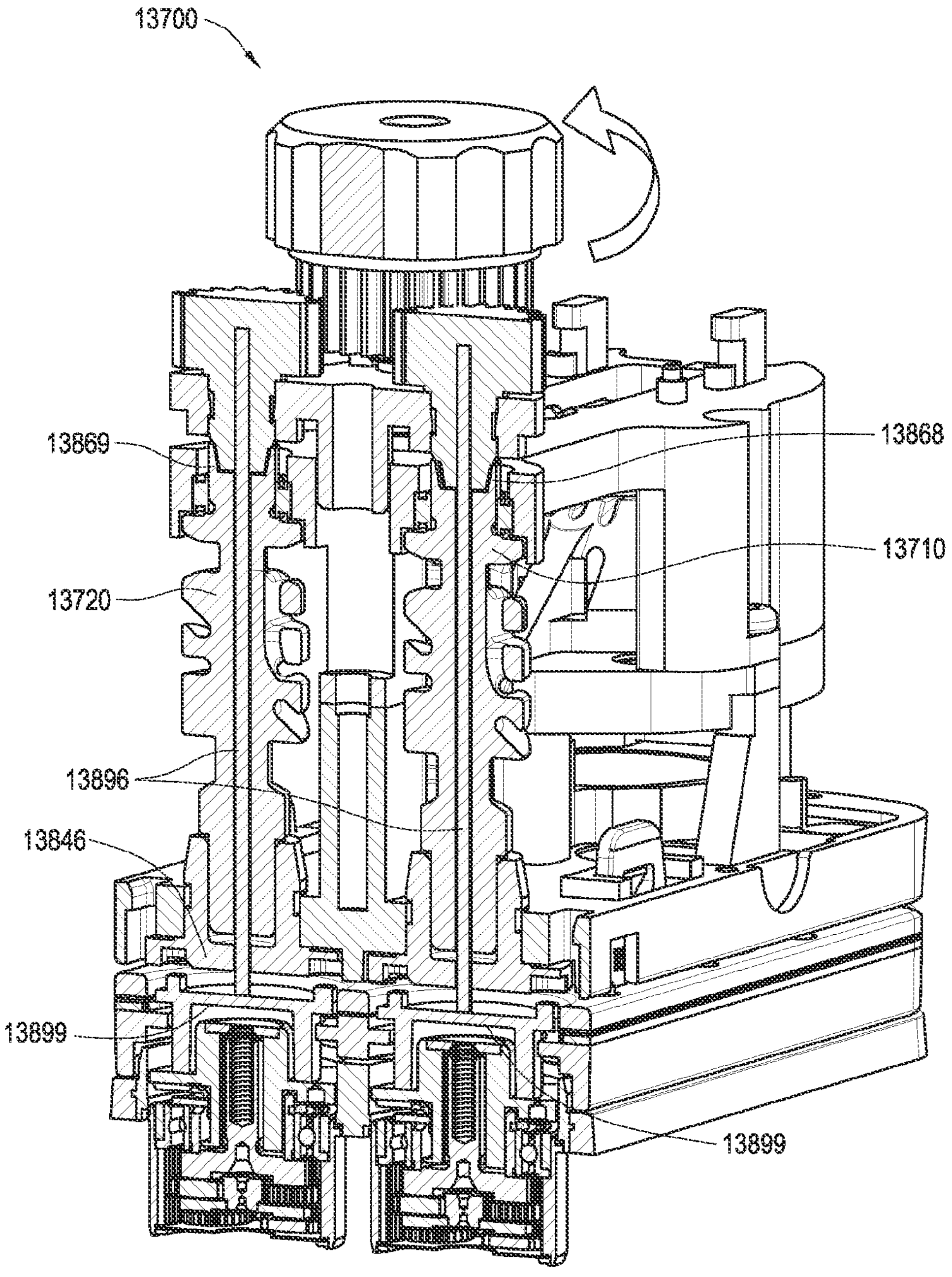

The mechanical motor disconnect 13896 protrudes from the base as shown in FIGS. 42B and 42C. In this way, the mechanical motor disconnects can contact and press a portion of the motor coupling 13899 away from their engagement with the proximal mechanical structure 13700 drive disks 13846 thereby removing automated power from the mechanical structure 13700 while the manual drive structure 13860 is use. The motor coupling 13899 includes a disk that engages the drive disk 13899 that is spring loaded to flex towards or away from the drive disks 13846. This coupler is actively driven by the motor. In response to pressure from the mechanical motor disconnect 13896, the motor coupler disk is moved out of engagement with the drive disk 13746. FIGS. 43A and B illustrates a cross section progression from engagement between motor coupling 13899 and drive disk 13846 (FIG. 43A) to disengagement (FIG. 43A).

As shown in FIGS. 42A-C the manual drive structure 13860 is a plunging style selectively engageable system. As the manual drive structure 13860 translates downwardly, the mechanical motor disconnect 13896 translates downwardly with the manual drive structure 13860. In this way, the disconnect removes the automated power as the manual drive structure 13860 selectively engages the capstans 13710 and 13720.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys or the like. Further, any of the links, tool members, tension members, or components described herein can be constructed from multiple pieces that are later joined together. For example, in some embodiments, a link can be constructed by joining together separately constructed components. In other embodiments however, any of the links, tool members, tension members, or components described herein can be monolithically constructed.

Although the instruments are generally shown as having an axis of rotation of the tool members (e.g., axis A1) that is normal to an axis of rotation of the wrist member (e.g., axis A2), in other embodiments any of the instruments described herein can include a tool member axis of rotation that is offset from the axis of rotation of the wrist assembly by any suitable angle.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. A medical device, comprising:

a manual drive structure including a manual drive input member, a manual drive input gear extending distally from the manual drive input member, and a manual drive coupling member; and a tool drive member including a motor drive input member, wherein:

the manual drive coupling member is selectively adjustable between a first state that is substantially free of engagement between the manual drive input member and the tool drive member and a second state in which the manual drive input member and the tool drive member are operably coupled, and the manual drive input gear is meshed with a manual-drive-side coupling gear portion of the manual drive coupling member in both the first state and the second state.

2. The medical device of claim 1, wherein:

the manual drive input member is rotatably movable with the movement resulting in adjustment between the first state and the second state.

3. The medical device of claim 2, wherein:

the manual drive coupling member includes a tool-drive-side coupling gear portion;

in the second state, the tool-drive-side coupling gear portion is engaged with the tool drive member; and in the first state, the tool-drive-side coupling gear portion is dis-engaged from the tool drive member.

4. The medical device of claim 3, wherein:

the tool-drive-side coupling gear portion includes an engagement portion and a non-engagement portion; and the tool drive member is engaged with the engagement portion in the second state and positioned adjacent to the non-engagement portion in the first state.

5. The medical device of claim 4, wherein:

the tool-drive-side coupling gear portion includes teeth along the engagement portion and no teeth along the non-engagement portion; and the manual-drive-side coupling gear portion includes a plurality of teeth distributed equidistantly along a circumference of the manual-drive-side coupling gear portion.

6. The medical device of claim 4, wherein:

the non-engagement portion extends along an arc in a range of 15 degrees to 45 degrees.

7. The medical device of claim 4, wherein:

the tool drive member is a first tool drive member;

the non-engagement portion is a first non-engagement portion;

the engagement portion is a first engagement portion;

the tool-drive-side coupling gear portion includes a second engagement portion positioned circumferentially between the first non-engagement portion and a second non-engagement portion; and a second tool drive member is engaged with the second engagement portion in the second state and positioned adjacent to the second non-engagement portion in the first state.

8. The medical device of claim 1, wherein:

the manual drive coupling member is biased to return to the first state on a condition that a user is not applying a manual force to the manual drive input member.

9. The medical device of claim 8, wherein:

the medical device further comprises a chassis and a housing;

the manual drive input member, the manual drive coupling member, the tool drive member, and the housing are supported by the chassis; and the manual drive input member extends external to the housing such that the manual drive input member provides a manual interface allowing a user to actuate the tool drive member on a condition that the manual drive coupling member is rotated to the second state.

10. The medical device of claim 1, wherein:

the medical device further comprises a chassis;

the chassis includes a first end stop and a second end stop;

the manual drive coupling member includes a first stop protrusion and a second stop protrusion;

the first stop protrusion is positioned to contact the first end stop;

the second stop protrusion is positioned to contact the second end stop; and a circumferential distance between the first stop protrusion and the second stop protrusion and the positioning of the first end stop and the second end stop defines an angular range of motion of the manual drive coupling member.

11. The medical device of claim 10, wherein:

the first stop protrusion is in contact with the first end stop on a condition that the manual drive coupling member is at a first rotational position corresponding to the first state; and the first stop protrusion is separated from the first end stop on a condition that the manual drive coupling member is at a second rotational position corresponding to the second state.

12. The medical device of claim 10, wherein:

the angular range of motion of the manual drive coupling member has a magnitude in a range of 60 degrees to 120 degrees.

13. A medical device, comprising:

a manual drive input member including a manual interface and an output gear extending in a distal direction, the manual drive input member being rotatable about a first rotational axis; and a manual drive coupling member rotatable between a first rotational position corresponding to a first state and a second rotational position corresponding to a second state about a second rotational axis, the second rotational axis being parallel to and offset from the first rotational axis, wherein:

the manual drive input member is operably coupled to a capstan of the medical device in the second state and operably decoupled from the capstan in the first state, the manual drive coupling member includes a manual-drive-side coupling gear portion and a tool-drive-side coupling gear portion, the manual-drive-side coupling gear portion is meshed with the output gear in both the first state and the second state, the tool-drive-side coupling gear portion includes a non-engagement portion, and the non-engagement portion is positioned adjacent to the capstan on a condition that the manual drive coupling member is at the first rotational position.

14. The medical device of claim 13, further comprising:

a chassis including a first spindle and a second spindle separated from the first spindle, wherein:

the first spindle supports the manual drive input member and defines the first rotational axis, and the second spindle supports the manual drive coupling member and defines the second rotational axis.

15. The medical device of claim 14, wherein:

the chassis includes a first end stop and a second end stop;

the manual drive coupling member includes a first stop protrusion and a second stop protrusion;

the first stop protrusion is positioned to contact the first end stop;

the second stop protrusion is positioned to contact the second end stop; and a circumferential distance between the first stop protrusion and the second stop protrusion and the positioning of the first end stop and the second end stop defines an angular range of motion of the manual drive coupling member.

16. The medical device of claim 15, wherein:

the first stop protrusion is in contact with the first end stop on a condition that the manual drive coupling member is at the first rotational position; and the first stop protrusion is separated from the first end stop on a condition that the manual drive coupling member is at the second rotational position.

17. The medical device of claim 13, wherein:

the tool-drive-side coupling gear portion includes an engagement portion and a non-engagement portion;

the engagement portion has a plurality of gear teeth;

the non-engagement portion has an absence of gear teeth; and the capstan is meshed with the plurality of gear teeth of the engagement portion on a condition that the manual drive coupling member is at the second rotational position.

18. The medical device of claim 17, wherein:

the tool-drive-side coupling gear portion includes a gear tooth gradient portion positioned between the engagement portion and the non-engagement portion; and the gear tooth gradient portion includes at least one gear tooth that is smaller than the gear teeth of the plurality of gear teeth of the engagement portion.

19. The medical device of claim 17, wherein:

the non-engagement portion extends along an arc in a range of 15 degrees to 45 degrees.

20. The medical device of claim 13, wherein:

the manual drive input member is a monolithic structure.

* * * * *